US011541104B2

(12) United States Patent
Minamida et al.

(10) Patent No.: US 11,541,104 B2
(45) Date of Patent: Jan. 3, 2023

(54) METHOD FOR PREVENTING OR TREATING OSTEOPOROSIS, CHARACTERIZED BY ADMINISTERING TERIPARATIDE OR SALT THEREOF AT A FREQUENCY OF TWICE A WEEK

(71) Applicant: ASAHI KASEI PHARMA CORPORATION, Tokyo (JP)

(72) Inventors: Takeshi Minamida, Tokyo (JP); Ryo Kato, Tokyo (JP); Akira Koike, Tokyo (JP); Atsushi Ose, Tokyo (JP); Akihiro Kitami, Tokyo (JP); Takashi Makiyama, Tokyo (JP); Hikaru Yamamoto, Tokyo (JP); Kazuhiko Kitagawa, Tokyo (JP); Ryoko Takao, Tokyo (JP)

(73) Assignee: ASAHI KASEI PHARMA CORPORATION, Tokyo (JP)

( * ) Notice: Subject to any disclaimer, the term of this patent is extended or adjusted under 35 U.S.C. 154(b) by 0 days.

(21) Appl. No.: 17/315,020

(22) Filed: May 7, 2021

(65) Prior Publication Data
US 2021/0260166 A1 Aug. 26, 2021

Related U.S. Application Data

(60) Division of application No. 17/104,734, filed on Nov. 25, 2020, now abandoned, which is a continuation of application No. PCT/JP2019/030099, filed on Jul. 31, 2019.

(30) Foreign Application Priority Data

Oct. 29, 2018 (JP) .............................. JP2018-203235

(51) Int. Cl.
*A61K 38/29* (2006.01)
*A61K 9/00* (2006.01)

(52) U.S. Cl.
CPC ............ *A61K 38/29* (2013.01); *A61K 9/0019* (2013.01)

(58) Field of Classification Search
None
See application file for complete search history.

(56) References Cited

U.S. PATENT DOCUMENTS

| 5,407,911 | A | * | 4/1995 | Yamamoto | ........... | A61K 9/0043 |
| | | | | | | 514/11.8 |
| 5,616,560 | A | | 4/1997 | Geddes et al. | | |
| 5,662,604 | A | * | 9/1997 | Ogata | ..................... | C12Q 1/34 |
| | | | | | | 604/28 |
| 2002/0007140 | A1 | | 1/2002 | Iga et al. | | |
| 2002/0107200 | A1 | * | 8/2002 | Chang | ..................... | A61K 47/26 |
| | | | | | | 514/11.8 |
| 2007/0173447 | A1 | * | 7/2007 | Quay | ..................... | A61K 38/29 |
| | | | | | | 514/11.8 |
| 2012/0262729 | A1 | | 10/2012 | Shirae et al. | | |
| 2020/0289622 | A1 | * | 9/2020 | Miyabe | .................. | A61K 47/26 |

FOREIGN PATENT DOCUMENTS

| JP | 8-73376 A | | 3/1996 |
| WO | WO 00/10596 A1 | | 3/2000 |
| WO | WO 2018189674 | * | 10/2008 |
| WO | WO 2011/930774 A1 | | 3/2011 |

OTHER PUBLICATIONS

Blick, S.K.A., Dhillon, S. & Keam, S.J. Teriparatide—A Review of Its Use in Osteoporosis. Drugs 68, 2709-2737 (2008). https://doi.org/10.2165/0003495-200868180-00012.*
Fujita et al., Calcif Tissue Int., 94, pp. 170-175, 2014.*
"Yakuzai Netsu Nitsuite (Drug Fever)," Kagoshima-shi iho (Journal of the Kagoshima City Medical Association), 2006, vol. 45, No. 9, 3 pages, with English translation.
Fujita et al., "Effect of an intermittent weekly dose of human parathyroid hormone (1-34) on osteoporosis: a randomized double-masked prospective study using three dose levels," Osteoporosis International, Vo. 9, 1999, pp. 296-306.
Fujita et al., "Once-weekly injection of low-dose teriparatide (28.2 µg) reduced the risk of vertebral fracture in patients with primary osteoporosis," Calcified Tissue International, vol. 94, 2014, pp. 170-175.
Fukunaga et al., "Absolute height reduction and percent height ratio of the vertebral body in incident fracture in Japanese women," Journal of Bone and Mineral Metabolism, vol. 22, 2004, pp. 104-110.
Fukunaga, "Twenty-five years of methods for quantifying bone mineral density—from development to use in osteoporosis," Kawasaki Medical Journal, 2010, vol. 36, No. 2, pp. 153-157 (14 pages total), with English translation.
Genant et al., "Vertebral fracture assessment using a semiquantitative technique," Journal of Bone and Mineral Research, vol. 8, No. 9, 1993, pp. 1137-1148.
Glover et al., "Rapid and robust response of biochemical markers of bone formation to teriparatide therapy," Bone, vol. 45, 2009, pp. 1053-1058.
Hagino, "Uses of New Osteoporosis Therapeutic Agent" Teriparatide Preparation of Once-Weekly Administration"(Teribone® Subcutaneous Injectable 56.5 µg) to Elderly Individuals," Progress in Medicine, 2012, vol. 32, pp. 373-378. (19 pages total), with English translation.
International Search Report (PCT,ISA/210) issued in PCT/JP2019/030099 dated Oct. 8, 2019.

(Continued)

*Primary Examiner* — Maury A Audet
(74) *Attorney, Agent, or Firm* — Birch, Stewart, Kolasch & Birch, LLP

(57) ABSTRACT

[Problems] To provide a method for treating and/or preventing osteoporosis with teriparatide or a salt thereof, the method having excellent safety and/or efficacies.
[Solving Means] A method for treating and/or preventing osteoporosis in which teriparatide or a salt thereof is an active ingredient, including administering teriparatide or a salt thereof in a unit dose of 28.2 µg at a frequency of twice a week.

2 Claims, 29 Drawing Sheets

(56) References Cited

OTHER PUBLICATIONS

Iyakuhin Intabyu Fohm Nihon Hyojun Shohin Bunrul Bango (Pharmaceutical Interview Form Japan Standard Goods Classification No. 872439, Aug. 2018, 110 pages, with partial English transiation.
Kato et al., "Toxicity and safety of Drugs," Kagaku Kyoiku (Chemical Education), vol. 31, No. 2, 1983, pp. 97-101 (19 pages total), with English translation.
Kumagai et al., "Safety Profiles, Pharmacokinetics, and Changes in Bone Turnover Markers After Twice-Weekly Subcutaneous Administration of Teriparatide in Healthy Japanese Postmenopausal Women: a Single-Blind Randomized Study," Clinical Pharmacology in Drug Development, 2019, pp. 1-10 / 11 pages total).
Lips et al., "Vitamin D supplements with or without calcium to prevent fractures," BoneKEy Reports 3, Article No. 512, 2014, pp. 1-6.
Miki et al., "Effect and safety of intermittent weekly administration of human parathyroid hormone 1-34 in patients with primary osteoporosis evaluated by histomorphometry and microstructural analysis of iliac trabecular bone before and after 1 year of treatment," Journal of Bone and Mineral Metabolism, vol. 22, 2004, pp. 569-576.
Miyauchi et al., "Effect of teriparatide on bone mineral density and biochemical markers in Japanese women with postmenopausal osteoporosis: a 6-month dose-response study," Journal of Bone and Mineral Metabolism, vol. 26, 2008, pp. 624-634.
Mok et al., "Parathyroid hormone as a smooth muscle relaxant," Endocrine Reviews, vol. 10, No. 4, 1989, pp. 420-436.
Nakamura et al., "Randomized Teriparatide [human parathyroid hormone (PTH) 1-34] Once-Weekly Efficacy Research (TOWER) trial for examining the reduction in new vertebral fractures in subjects with primary osteoporosis and high fracture risk," The Journal of Clinical Endocrinology & Metabolism, vol. 97, No. 9, 2012, pp. 3097-3106.
Neer et al., "Effect of parathyroid hormone (1-34) on fractures and bone mineral density in postmenopausal women with osteoporosis," New England Journal of Medicine, vol. 344, No. 19, 2001, pp. 1434-1441.
NIH Consensus Development Panel on Osteoporosis Prevention, Diagnosis, and Therapy, "Osteoporosis prevention, diagnosis, and therapy," JAMA, vol. 285, No. 6, 2001, pp. 785-795.
Package Insert of Forteo® Subcutaneous Injection Kit 690 μg, revised Jan. 2018, 22 pages, with English transiation.
Package Insert of Teribone® for Subcutaneous Injection 56.5 μg, revised Jan. 2018, 22 pages, with English translation.
Sethi et al., "Efficacy of teriparatide in increasing bone mineral density in postmenopausal women with osteoporosis—an Indian experience," JAPI, vol. 56, 2008, pp. 418-424.
Sugimoto et al., "24-month open-label teriparatide once-weekly efficacy research trial examining bone mineral density in subjects with primary osteoporosis and high fracture risk," Advances in Therapy, vol. 34, 2017, pp. 1727-1740.
Takakura et al., "Administration frequency as well as dosage of PTH are associated with development of cortical porosity in ovariectomized rats," Bone Research, 2017, vol. 5, 17002, DOI:10.1038/boneres.2017.2, pp. 1-14.
Takakura et al., "High Administration Frequency of Teriparatide Induces Formation of Cortical Porosity," Journal of Japanese Society for Bone Morphometry, vol. 28, 2018, pp. 31-37 (23 pages total), with English translation.
Takeuchi, "Endocrinal Diseases: Progress in Diagnosis and Treatment," The Journal of the Japanese Society of Internal Medicine, 2012, vol. 101, No. 4, pp. 1007-1014 (22 pages total), with English translation.
Usui et al., "Persistence of and switches from teriparatide treatment among women and men with osteoporpsis in the real world: a claims database analysis," Archives of Osteoporosis, vol. 13:54, 2018, pp. 1-8.
Written Opinion (PCT/ISA/237) issued in PCT/JP2019/030099 dated Oct. 8, 2019.
Wu et al., "Comparison of semiquantitative and quantitative techniques for the assessment of prevalent and incident vertebral fractures," Osteoporosis International, vol. 5, 1995, pp. 354-370.
Yamane et al., "Acute development of cortical porosity and endosteal naive bone formation from the daily but not weekly short-term administration of PTH in rabbit," PloS one, 2017, e0175329, 26 pages.
Blick, S.K.A., Dhillon, S. & Kearn, S.J. Teriparatide—A Review of Its Use in Osteoporosis. Drugs 68, 2709-2737 (2008). https://doi.org/10.2165/0003495-200868180-00012.
Tanaka, "Osteoporosis—what you can do to prevent bone fractures in elderly individuals," Geriatric Medicine, vol. 56, No. 12, 2018, pp. 1225-1230 (17 pages total), with English translation.
International Preliminary Report on Patentability dated Apr. 27, 2021 in PCT/JP2019/030099.
Office Action dated Feb. 2, 2022 for Canadian Patent Application No. 3,101,326.
Extended European Search Report for corresponding European Application No. 19879778.9, dated May 31, 2022.
Japanese Office Action for Japanese Application No. 2021-094917, dated Mar. 28, 2022, with English translation.

\* cited by examiner

FIG. 1

| Administration intervals | First Day of Administration | Week 1 | | | | | | | Week 2 | | | | | | |
|---|---|---|---|---|---|---|---|---|---|---|---|---|---|---|---|
| | | Day 2 | Day 3 | Day 4 | Day 5 | Day 6 | Day 7 | Day 8 | Day 9 | Day 10 | Day 11 | Day 12 | Day 13 | Day 14 |
| Example of 1-day and 6-day intervals (0-day and 5-day intervals, not including the days of administration) | Administered | ←Five days→ | | | | | Administered | | | | | | | Administered |
| Example of 2-day and 5-day intervals (1-day and 4-day intervals, not including the days of administration) | Administered | ←Four days→ | | | | Administered | ←One day→ | Administered | | | | | Administered | ←One day→ |
| Example of 3-day and 4-day intervals (2-day and 3-day intervals, not including the days of administration) | Administered | ←Three days→ | | | Administered | ←Two days→ | | Administered | ←Three days→ | | | Administered | ←Two days→ | |

FIG. 2

| First Day of Administration | Week 1 | | | | | | Week 2 | | | | | | |
|---|---|---|---|---|---|---|---|---|---|---|---|---|---|
| | Day 2 | Day 3 | Day 4 | Day 5 | Day 6 | Day 7 | Day 8 | Day 9 | Day 10 | Day 11 | Day 12 | Day 13 | Day 14 |
| Administered | | | Administered | | | | | | | | | | |
| Administered | | | Administered | | | | Administered | | | | | | |
| Administered | | | | Administered | | | Administered | | | Administered | | | |
| Administered | | | | Administered | | | Administered | | | | Administered | | |
| Administered | | | | | | | Administered | | | | Administered | | |

FIG. 29

Basic Administration Schedule of Both Groups

| | Week 1 | | | | | | | Week 2 | | |
|---|---|---|---|---|---|---|---|---|---|---|
| | Day 1 | Day 2 | Day 3 | Day 4 | Day 5 | Day 6 | Day 7 | Day 8 | ... | ... |
| Test Drug Group | ● △ | | | ● | | | | ● △ | ... | ... |
| Control Drug Group | ○ ▲ | | | ○ | | | | ○ ▲ | | |

● : Actual Drug of Test Drug (MN-10-T AI)
○ : Placebo of Test Drug (MN-10-T AI Placebo)
▲ : Actual Drug of Control Drug (MN-10-T)
△ : Placebo of Control Drug (MN-10-T Placebo)

METHOD FOR PREVENTING OR TREATING OSTEOPOROSIS, CHARACTERIZED BY ADMINISTERING TERIPARATIDE OR SALT THEREOF AT A FREQUENCY OF TWICE A WEEK

CROSS REFERENCE TO RELATED APPLICATIONS

This application is a Divisional of U.S. application Ser. No. 17/104,734 filed on Nov. 25, 2020, which is a Continuation of PCT International Application No. PCT/JP2019/030099, filed on Jul. 31, 2019, which claims priority under 35 U.S.C. 119(a) to Patent Application No. 2018-203235, filed in Japan on Oct. 29, 2018, all of which are hereby expressly incorporated by reference into the present application.

TECHNICAL FIELD

The present invention relates to a method for preventing or treating osteoporosis, characterized by administering teriparatide or a salt thereof at a frequency of twice a week.

BACKGROUND ART

Osteoporosis is defined as "a skeletal disease characterized by compromised bone strength predisposing a person to an increased risk of fracture" (Non-Patent Publication 1), and this definition has been generally used.

It has been said that main purposes of prevention and treatment of osteoporosis are to prevent or inhibit bone fractures, maintain the life functions and the QOL (Quality of Life), and the like. Pains caused by bone fractures and decrease in physical support functions, and subsequent life functional disorders caused by motor functional disorders are serious problems, so that it is said to particularly have a high clinical significance in the prevention and treatment of osteoporosis with a high risk of bone fractures.

Under the background described above, as a drug having the efficacies and effects for osteoporosis with a high risk of bone fractures, a daily administered preparation or a once-weekly administered preparation, each containing teriparatide or a salt thereof as an active ingredient, has been developed. After being approved for sales thereof, the preparation has been actually used in clinical situations (Non-Patent Publications 4 and 8).

However, it is said that a daily administered preparation or a once-weekly administered preparation, each containing teriparatide or a salt thereof as an active ingredient, is not necessarily satisfactorily excellent from the viewpoint of safety.

PTH has been known to have a relaxation action of vascular smooth muscles (Non-Patent Publication 21). In clinical tests using a daily administered preparation, it has been reported that dizziness is significantly high as compared to that of a placebo group (Non-Patent Publication 9). In addition, it has also been known to show shocks, or unconsciousness accompanying a transient drastic blood pressure drop, convulsion, or fall, from immediately after to several hours after the administration of a daily administered preparation or a once-weekly administered preparation (Non-Patent Publications 4 and 8).

Alternatively, it has been reported that nausea, vomiting, headaches, or the like is often observed by the administration of teriparatide acetate (Non-Patent Publication 9). For example, it has been reported that in clinical tests using a once-weekly administered preparation, the nauseation frequency is significantly high, as compared to that of a placebo group, and the numerical value also exceeded 20% of the entire group of the once-weekly administered preparations, and that the administration discontinuation rate due to adverse events also showed a high numerical value of about 20% (Non-Patent Publication 5).

Further, it has been reported that in clinical tests using a daily administered preparation, the incidence rate of a mid-level hypercalcemia (exceeding 10.6 mg/dl) was 11% (2% in a placebo group) (Non-Patent Publication 7).

Besides, in tests using a once-weekly administered preparation or a daily administered preparation, fervescence has been observed as an adverse event (Non-Patent Publications 6 and 21).

In general, it has been reported that the drug ingestion situations in drug therapies for osteoporosis are such that 52.1% of the individuals undesirably drop out from the ingestion within 5 years after the beginning of the treatment, and there are some disadvantages addressed to the lowering in the inhibition of bone fractures, the increased needs of use of facilities, and stagnancy in medical cost reductions, due to unsatisfactory compliance to drug ingestions (Non-Patent Publication 9). Factors associated with the failure to the compliance to the drug ingestions are exemplified by the presence of pains, side effects, drugs ingested for gastrointestinal disorders, and the like (Non-Patent Publication 9).

On the other hand, it has been pointed out that a preparation containing teriparatide or a salt thereof as an active ingredient has the lowness of the continuation rate of treatment, and it has been reported that the continuation rate of treatment over a period of 12 months is 34.9% (Non-Patent Publication 22). As to safety, it has been known to have the concern of the lowering in the drug ingestion adherence due to side reactions. It has been reported that in tests using a once-weekly administered preparation, adverse events that lead to the discontinuation of administration of the investigational products other than the serious cases are as high as 14.1% in the present preparation group (Non-Patent Publication 23).

As described above, a daily administered preparation or a once-weekly administered preparation, each containing teriparatide or a salt thereof as an active ingredient, shows many disadvantages in the aspects of safety, and it is also not necessarily said to provide sufficient benefits from the aspects of efficacies.

For example, it has been reported that in clinical tests having an administration period of 72 weeks in which a once-weekly administered preparation is used in osteoporosis patients with high risks of bone fractures, the bone mineral density of lumbar vertebrae at a time point of 48 weeks after the beginning of administration is elevated by 4.9 to 6.0% or so (Patent Publication 1 (Table 26), Non-Patent Publication 5 (FIG. 3)). In addition, it has been reported that in clinical tests having an administration period of 24 months in which a once-weekly preparation is used to osteoporosis patients with high risks of bone fractures, the bone mineral density of lumbar vertebrae at the time point of 48 weeks after the beginning of administration is elevated by about 6.9% (Non-Patent Publication 6).

As to the efficacies regarding both the preparations, not only the effects of increasing bone mineral density but also the effects of inhibiting bone fractures have been known. For example, it has been reported that in clinical tests using a daily administered preparation, the risks of bone fractures of lumbar vertebrae are lowered by 65% (Non-Patent Publication 7).

In addition, it has been reported in recent year animal experiments and investigational studies that the daily administration of teriparatide shows strong bone formation-accelerating action at sites with abundant trebeculae such as centra, but on the other hand, the administration increases voids in cortical bones such as quadrupedal bones, that a possibility of having a different action to the cortical bones according to the administration frequencies has been considered even in the intermittent administration of PTH, or the like (Non-Patent Publication 14). Further, it has been reported that CTX, which is one of bone resorption markers, is found to have a tendency of elevating in a dose-dependent manner, as compared to that at the beginning of administration, at 24 weeks after the beginning of the daily administration of teriparatide.

It has been reported from the studies in ovary-excised rats which have been widely used as osteoporosis models that bone mineral density and bone strength are increased in accordance with a weekly dosage of teriparatide (Non-Patent Publication 14).

PRIOR ART REFERENCES

Patent Publications

Patent Publication 1: WO 2011/030774
Patent Publication 2: Japanese Patent Laid-Open No. Hei-8-73376
Patent Publication 3: WO 2000/10596

Non-Patent Publications

Non-Patent Publication 1: *JAMA*, (2001), 285(6), 785-795
Non-Patent Publication 2: *Osteoporos Int*, (1999), 9, 296-306
Non-Patent Publication 3: *J Bone Miner Metab* (2004), 22, 569-576
Non-Patent Publication 4: *Package Insert of Teribone* (Registered Trademark) *Subcutaneous Injection* 56.5 µg (revised August, 2018)
Non-Patent Publication 5: *J Clin Endocrinol Metab* (2012), 97(9), 3097-3106
Non-Patent Publication 6: *Adv Ther* (2017), 34, 1727-1740
Non-Patent Publication 7: *N Engl J Med* (2001), 344(19), 1434-1441
Non-Patent Publication 8: *Package Insert of Forteo* (Registered Trademark) *Subcutaneous Injection Kit* 600 µg (revised January, 2018)
Non-Patent Publication 9: *Kotsusoshoshou no Yobo to Chiryo Gaidorain* (*Guidelines for Osteoporosis Prevention and Treatment*) 2015 Edition
Non-Patent Publication 10: *Genpatsusei Kotsusoshoshou no Shindan Kijun* (*Diagnostic Criteria for Primary Osteoporosis*) (Revised edition in the fiscal year of 2012)
Non-Patent Publication 11: *J Bone Miner Res* (1993), 8, 1137-1148
Non-Patent Publication 12: *Osteoporos Int* (1995), 5, 354-370
Non-Patent Publication 13: *J Bone Miner Metab* (2004), 22, 104-110
Non-Patent Publication 14: *Journal of Japanese Society for Bone Morphometry* (2018), 28, 31-37
Non-Patent Publication 15: "*Kotsusoshoshou you Yaku no Rinsho Hyokahoho ni Kansuru Gaidorain no Kaitei nitsuite* (*Revision on Guidelines on Clinical Assessment Method for Drugs for Osteoporosis*)" (2017), *Yaku-sei-yaku-shin-hatsu* (*Pharmaceutical Sanitation Bureau Drug Examination Management Notification*) 0707, no. 1
Non-Patent Publication 16: *Bone* 45 (2009), 1053-1058
Non-Patent Publication 17: *J Bone Miner Metab* (2008), 26, 624-634
Non-Patent Publication 18: *Kagoshima-shi Iho* (*JOURNAL OF THE KAGOSHIMA CITY MEDICAL ASSOCIATION*) (2006), 45(9) "Yakuzai Netsu nitsuite (Drug Fever)"
Non-Patent Publication 19: *JAPI* (2008), 56, 418-424
Non-Patent Publication 20: *Calcif Tissue Int* (2014), 94, 170-175
Non-Patent Publication 21: *Endocrine Reviews* (1989), 10(4), 420-436
Non-Patent Publication 22: *Arch Osteoporos.* (2018), 13(1): 54, s11657-018-0466-0
Non-Patent Publication 23: *Iyakuhin Intabyu Fohm Nihon Hyojun Shohin Bunrui Bango* (*Pharmaceutical Interview Form Japan Standard Goods Classification Number*): 872439
Non-Patent Publication 24: *The Journal of the Japanese Society of Internal Medicine* (2012), 101(4), 1007-1014
Non-Patent Publication 25: *BoneKEy Rep* (2014), 3(512)
Non-Patent Publication 26: *Kawasaki Medical Journal* (2010), 36(2), 153-157
Non-Patent Publication 27: *PLOS ONE* 12(4) e0175329 "Acute development of cortical porosity and endosteal naïve bone formation from the daily but not weekly short-term administration of PTH in rabbit."

SUMMARY OF THE INVENTION

Problems to be Solved by the Invention

An object of the present invention is to provide a method for treating and/or preventing osteoporosis with teriparatide or a salt thereof having excellent safety and/or efficacies; and an osteoporosis therapeutic and/or prophylactic agent containing teriparatide or a salt thereof as an active ingredient.

Means to Solve the Problems

One embodiment of an osteoporosis therapeutic and/or prophylactic agent and a method for treating and/or method for preventing osteoporosis of the present invention is characterized in that teriparatide or a salt thereof is contained as an active ingredient, and that the teriparatide or a salt thereof is administered in a unit dose of 28.2 µg at a frequency of twice a week.

The osteoporosis therapeutic and/or prophylactic agent and the method for treating and/or method for preventing osteoporosis mentioned above exhibit excellent safety and/or efficacies.

Specifically, the present invention relates to the following inventions and the like.

[1] An osteoporosis therapeutic and/or prophylactic agent containing teriparatide or a salt thereof as an active ingredient, characterized in that the teriparatide or a salt thereof is administered in a unit dose of 28.2 µg at a frequency of twice a week.

[2] The osteoporosis therapeutic and/or prophylactic agent according to the above [1], wherein the intervals of administration of twice a week (not including the days of administration) are a 2-day interval and a 3-day interval.

[3] The osteoporosis therapeutic and/or prophylactic agent according to the above [1], wherein when the number of weeks of a period administered at a frequency of twice a week is defined as n, and the number of weeks out of the n weeks in which the intervals of administration of twice a week (not including the days of administration) are 2 days and 3 days is defined as m, (m/n)×100(%) is 70% or more.

[4] The osteoporosis therapeutic and/or prophylactic agent according to any one of the above [1] to [3], which is subcutaneously administered.

[5] The osteoporosis therapeutic and/or prophylactic agent according to any one of the above [1] to [4], which is administered to an individual having a bone mineral density of lumbar vertebrae less than 60% of a young adult mean.

[6] The osteoporosis therapeutic and/or prophylactic agent according to any one of the above [1] to [4], which is administered to an individual with one prevalent vertebral fracture.

[7] The osteoporosis therapeutic and/or prophylactic agent according to any one of the above [1] to [4], which is administered to an individual having a serum osteocalcin concentration of less than 15.2 (ng/mL).

[8] The osteoporosis therapeutic and/or prophylactic agent according to any one of the above [1] to [4], which is administered to an individual with an age 80 years or older.

[9] The osteoporosis therapeutic and/or prophylactic agent according to any one of the above [1] to [4], which is administered to male.

[10] The osteoporosis therapeutic and/or prophylactic agent according to any one of the above [1] to [4], which is administered to an osteoporosis patient with a high risk of bone fractures.

[11] The osteoporosis therapeutic and/or prophylactic agent according to any one of the above [1] to [4], which is administered to an osteoporosis patient with all the bone fracture risk factors of aging, prevalent bone fractures, and low bone mineral density.

[12] The osteoporosis therapeutic and/or prophylactic agent according to any one of the above [1] to [4], which is administered to an osteoporosis patient satisfying the following conditions (1) to (3):
(1) an age 65 years or older;
(2) prevalent vertebral bone fractures of one or more and five or less; and
(3) a bone mineral density of lumbar vertebrae less than 80% of a young adult mean.

Advantageous Effects of the Invention

According to the present invention, the osteoporosis therapeutic and/or prophylactic agent and the method for treating and/or method for preventing osteoporosis, in which teriparatide or a salt thereof is contained as an active ingredient, with excellent safety and/or efficacies are provided.

BRIEF DESCRIPTION OF THE DRAWINGS

FIG. 1 is a diagram showing administration scheme examples in cases where an osteoporosis therapeutic agent or the like of the present invention is administered at a frequency of twice a week over two weeks, in which the intervals of administration are set at a 1-day interval and a 6-day interval (a 0-day interval and a 5-day interval, when not including the days of administration), set at a 2-day interval and a 5-day interval (a 1-day interval and a 4-day interval, when not including the days of administration), or set at a 3-day interval and a 4-day interval (a 2-day interval and a 3-day interval, when not including the days of administration).

FIG. 2 is a diagram showing administration scheme examples in cases where an osteoporosis therapeutic agent or the like of the present invention is administered at a frequency of twice a week over two weeks, in which the intervals of administration are set at a 3-day interval and a 4-day interval (a 2-day interval and a 3-day interval, when not including the days of administration).

FIG. 4 is a graph showing the transition of a mean value of change rates (%) in bone mineral densities of lumbar vertebrae (second to fourth lumbar vertebrae) when the osteoporosis therapeutic agent or the like of the present invention is administered to osteoporosis patients over a period of 48 weeks, wherein the axis of abscissas is the number of weeks administered, and the axis of ordinates is a mean value of change rates (%) from the beginning; "BL" is Baseline; and "Final" means "at final of the treatment" for showing a change rate (%) in bone mineral densities of lumbar vertebrae (second to fourth lumbar vertebrae) at final of the treatment for each patient, including change rates (%) in bone mineral densities of lumbar vertebrae (second to fourth lumbar vertebrae) of patients in which the treatment is discontinued during the course of 48 weeks. The numerical values shown in the two lower rows mean the number of treated patients in each week; and "*" denotes for p<0.01.

FIG. 5 is a graph showing the transition of a median value of change rates (%) in serum CTX when the osteoporosis therapeutic agent or the like of the present invention is administered to osteoporosis patients over a period of 48 weeks, wherein the axis of abscissas is the number of weeks administered, and the axis of ordinates is a median value of change rates (%) from the beginning; and "BL" is Baseline. The numerical values shown in the two lower rows mean the number of patients who took the tests in each week.

FIG. 6 is a graph showing the transition of a median value of change rates (%) in serum NTX when the osteoporosis therapeutic agent or the like of the present invention is administered to osteoporosis patients over a period of 48 weeks, wherein the axis of abscissas is the number of weeks administered, and the axis of ordinates is a median value of change rates (%) from the beginning; and "BL" is Baseline. The numerical values shown in the two lower rows mean the number of patients who took the tests in each week.

FIG. 7 is a graph showing the transition of a median value of change rates (%) in urine NTX when the osteoporosis therapeutic agent or the like of the present invention is administered to osteoporosis patients over a period of 48 weeks, wherein the axis of abscissas is the number of weeks administered, and the axis of ordinates is a median value of change rates (%) from the beginning; and "BL" is Baseline. The numerical values shown in the two lower rows mean the number of patients who took the tests in each week.

FIG. 8 is a graph showing the transition of a median value of change rates (%) in serum OC (osteocalcin) when the osteoporosis therapeutic agent or the like of the present invention is administered to osteoporosis patients over a period of 48 weeks, wherein the axis of abscissas is the number of weeks administered, and the axis of ordinates is a median value of change rates (%) from the beginning; and "BL" is Baseline. The numerical values shown in the two lower rows mean the number of patients who took the tests in each week; "*" denotes that a Wilcoxon rank sum test p<0.05, and "*" denotes that a Wilcoxon rank sum test p<0.01, respectively.

FIG. 9 is a graph showing the transition of a median value of change rates (%) in serum P1NP when the osteoporosis therapeutic agent or the like of the present invention is administered to osteoporosis patients over a period of 48 weeks, wherein the axis of abscissas is the number of weeks administered, and the axis of ordinates is a median value of change rates (%) from the beginning; and "BL" is Baseline. The numerical values shown in the two lower rows mean the number of patients who took the tests in each week; "*" denotes that a Wilcoxon rank sum test p<0.05, and "*" denotes that a Wilcoxon rank sum test p<0.01, respectively.

FIG. 10 is a graph showing the transition of a mean value of change rates (%) in bone mineral densities of lumbar vertebrae (second to fourth lumbar vertebrae) when the osteoporosis therapeutic agent or the like of the present invention is administered to osteoporosis patients over a period of 48 weeks, in which a proportion in compliance with administration intervals is classified by 70% or more and less than 70%, wherein the axis of abscissas is the number of weeks administered, and the axis of ordinates is a mean value of change rates (%) from the beginning. The numerical values shown in the two lower rows mean the number of patients that are subjects to be analyzed in each week.

FIG. 11 is a graph showing the transition of a mean value of change rates (%) in bone mineral densities of lumbar vertebrae (second to fourth lumbar vertebrae) when the osteoporosis therapeutic agent or the like of the present invention is administered to osteoporosis patients over a period of 48 weeks, in which a proportion in compliance with administration intervals is classified by 75% or more and less than 75%, wherein the axis of abscissas is the number of weeks administered, and the axis of ordinates is a mean value of change rates (%) from the beginning. The numerical values shown in the two lower rows mean the number of patients that are subjects to be analyzed in each week.

FIG. 12 is a graph showing the transition of a mean value of change rates (%) in bone mineral densities of lumbar vertebrae (second to fourth lumbar vertebrae) when the osteoporosis therapeutic agent or the like of the present invention is administered to osteoporosis patients over a period of 48 weeks, in which a proportion in compliance with administration intervals is classified by 80% or more and less than 80%, wherein the axis of abscissas is the number of weeks administered, and the axis of ordinates is a mean value of change rates (%) from the beginning. The numerical values shown in the two lower rows mean the number of patients that are subjects to be analyzed in each week.

FIG. 13 is a graph showing the transition of a mean value of change rates (%) in bone mineral densities of lumbar vertebrae (second to fourth lumbar vertebrae) when the osteoporosis therapeutic agent or the like of the present invention is administered to osteoporosis patients over a period of 48 weeks, in which a proportion in compliance with administration intervals is classified by 85% or more and less than 85%, wherein the axis of abscissas is the number of weeks administered, and the axis of ordinates is a mean value of change rates (%) from the beginning. The numerical values shown in the two lower rows mean the number of patients that are subjects to be analyzed in each week.

FIG. 14 is a graph showing the transition of a mean value of change rates (%) in bone mineral densities of lumbar vertebrae (second to fourth lumbar vertebrae) when the osteoporosis therapeutic agent or the like of the present invention is administered to osteoporosis patients over a period of 48 weeks, in which a proportion in compliance with administration intervals is classified by 90% or more and less than 90%, wherein the axis of abscissas is the number of weeks administered, and the axis of ordinates is a mean value of change rates (%) from the beginning. The numerical values shown in the two lower rows mean the number of patients that are subjects to be analyzed in each week.

FIG. 15 is a graph showing the transition of a mean value of change rates (%) in bone mineral densities of the femoral neck parts when the osteoporosis therapeutic agent or the like of the present invention is administered to osteoporosis patients over a period of 48 weeks, in which a proportion in compliance with administration intervals is classified by 70% or more and less than 70%, wherein the axis of abscissas is the number of weeks administered, and the axis of ordinates is a mean value of change rates (%) from the beginning. The numerical values shown in the two lower rows mean the number of patients that are subjects to be analyzed in each week.

FIG. 16 is a graph showing the transition of a mean value of change rates (%) in bone mineral densities of the femoral neck parts when the osteoporosis therapeutic agent or the like of the present invention is administered to osteoporosis patients over a period of 48 weeks, in which a proportion in compliance with administration intervals is classified by 75% or more and less than 75%, wherein the axis of abscissas is the number of weeks administered, and the axis of ordinates is a mean value of change rates (%) from the beginning. The numerical values shown in the two lower rows mean the number of patients that are subjects to be analyzed in each week.

FIG. 17 is a graph showing the transition of a mean value of change rates (%) in bone mineral densities of the femoral neck parts when the osteoporosis therapeutic agent or the like of the present invention is administered to osteoporosis patients over a period of 48 weeks, in which a proportion in compliance with administration intervals is classified by 80% or more and less than 80%, wherein the axis of abscissas is the number of weeks administered, and the axis of ordinates is a mean value of change rates (%) from the beginning. The numerical values shown in the two lower rows mean the number of patients that are subjects to be analyzed in each week.

FIG. 18 is a graph showing the transition of a mean value of change rates (%) in bone mineral densities of the femoral neck parts when the osteoporosis therapeutic agent or the like of the present invention is administered to osteoporosis patients over a period of 48 weeks, in which a proportion in compliance with administration intervals is classified by 85% or more and less than 85%, wherein the axis of abscissas is the number of weeks administered, and the axis of ordinates is a mean value of change rates (%) from the beginning. The numerical values shown in the two lower rows mean the number of patients that are subjects to be analyzed in each week.

FIG. 19 is a graph showing the transition of a mean value of change rates (%) in bone mineral densities of the femoral neck parts when the osteoporosis therapeutic agent or the like of the present invention is administered to osteoporosis patients over a period of 48 weeks, in which a proportion in compliance with administration intervals is classified by 90% or more and less than 90%, wherein the axis of abscissas is the number of weeks administered, and the axis of ordinates is a mean value of change rates (%) from the beginning. The numerical values shown in the two lower rows mean the number of patients that are subjects to be analyzed in each week.

FIG. 20 is a graph showing the transition of a mean value of change rates (%) in a bone mineral density of the femoral proximal total when the osteoporosis therapeutic agent or the like of the present invention is administered to osteoporosis patients over a period of 48 weeks, in which a proportion in compliance with administration intervals is classified by 70% or more and less than 70%, wherein the axis of abscissas is the number of weeks administered, and the axis of ordinates is a mean value of change rates (%) from the beginning. The numerical values shown in the two lower rows mean the number of patients that are subjects to be analyzed in each week.

FIG. 21 is a graph showing the transition of a mean value of change rates (%) in a bone mineral density of the total proximal part of the femur when the osteoporosis therapeutic agent or the like of the present invention is administered to osteoporosis patients over a period of 48 weeks, in which a proportion in compliance with administration intervals is classified by 75% or more and less than 75%, wherein the axis of abscissas is the number of weeks administered, and the axis of ordinates is a mean value of change rates (%) from the beginning. The numerical values shown in the two lower rows mean the number of patients that are subjects to be analyzed in each week.

FIG. 22 is a graph showing the transition of a mean value of change rates (%) in a bone mineral density of the total proximal part of the femur when the osteoporosis therapeutic agent or the like of the present invention is administered to osteoporosis patients over a period of 48 weeks, in which a proportion in compliance with administration intervals is classified by 80% or more and less than 80%, wherein the axis of abscissas is the number of weeks administered, and the axis of ordinates is a mean value of change rates (%) from the beginning. The numerical values shown in the two lower rows mean the number of patients that are subjects to be analyzed in each week.

FIG. 23 is a graph showing the transition of a mean value of change rates (%) in a bone mineral density of the total proximal parts of the femur when the osteoporosis therapeutic agent or the like of the present invention is administered to osteoporosis patients over a period of 48 weeks, in which a proportion in compliance with administration intervals is classified by 85% or more and less than 85%, wherein the axis of abscissas is the number of weeks administered, and the axis of ordinates is a mean value of change rates (%) from the beginning. The numerical values shown in the two lower rows mean the number of patients that are subjects to be analyzed in each week.

FIG. 24 is a graph showing the transition of a mean value of change rates (%) in a bone mineral density of the total proximal parts of the femur when the osteoporosis therapeutic agent or the like of the present invention is administered to osteoporosis patients over a period of 48 weeks, in which a proportion in compliance with administration intervals is classified by 90% or more and less than 90%, wherein the axis of abscissas is the number of weeks administered, and the axis of ordinates is a mean value of change rates (%) from the beginning. The numerical values shown in the two lower rows mean the number of patients that are subjects to be analyzed in each week.

FIG. 25 is a graph showing a mean value of change rates (%) in bone mineral densities of lumbar vertebrae (second to fourth lumbar vertebrae) observed after 48 weeks of administration when the osteoporosis therapeutic agent or the like of the present invention is administered to osteoporosis patients showing some recordation of compliance in which the proportions in compliance of administration of each of two- to three-day intervals are each of specified numerical values (70, 75, 80, 85, or 90%) or more.

FIG. 26 is a graph showing a fracture incidence rate (%) in clinical bone fractures when the osteoporosis therapeutic agent or the like of the present invention is administered to osteoporosis patients showing some recordation of compliance in which the proportions in compliance with the administration of each of two- to three-day intervals are each of specified numerical values (70, 75, 80, 85, or 90%) or more.

FIG. 27 is a graph showing a median value of change rates (%) of OC at four weeks after the beginning of administration observed when the osteoporosis therapeutic agent or the like of the present invention is administered to osteoporosis patients showing some recordation of compliance in which the proportions in compliance with the administration of each of two- to three-day intervals are each of specified numerical values (70, 75, 80, 85, or 90%) or more.

FIG. 28 is a graph showing a proportion (%) expressing nausea (side effects) when the osteoporosis therapeutic agent or the like of the present invention is administered to osteoporosis patients showing some recordation of compliance in which the proportions in compliance with the administration of each of two- to three-day intervals are each of specified numerical values (70, 75, 80, 85, or 90%) or more.

FIG. 29 is a basic administration schedule for the test drug group and the control drug group.

MODES FOR CARRYING OUT THE INVENTION

Figure 3:
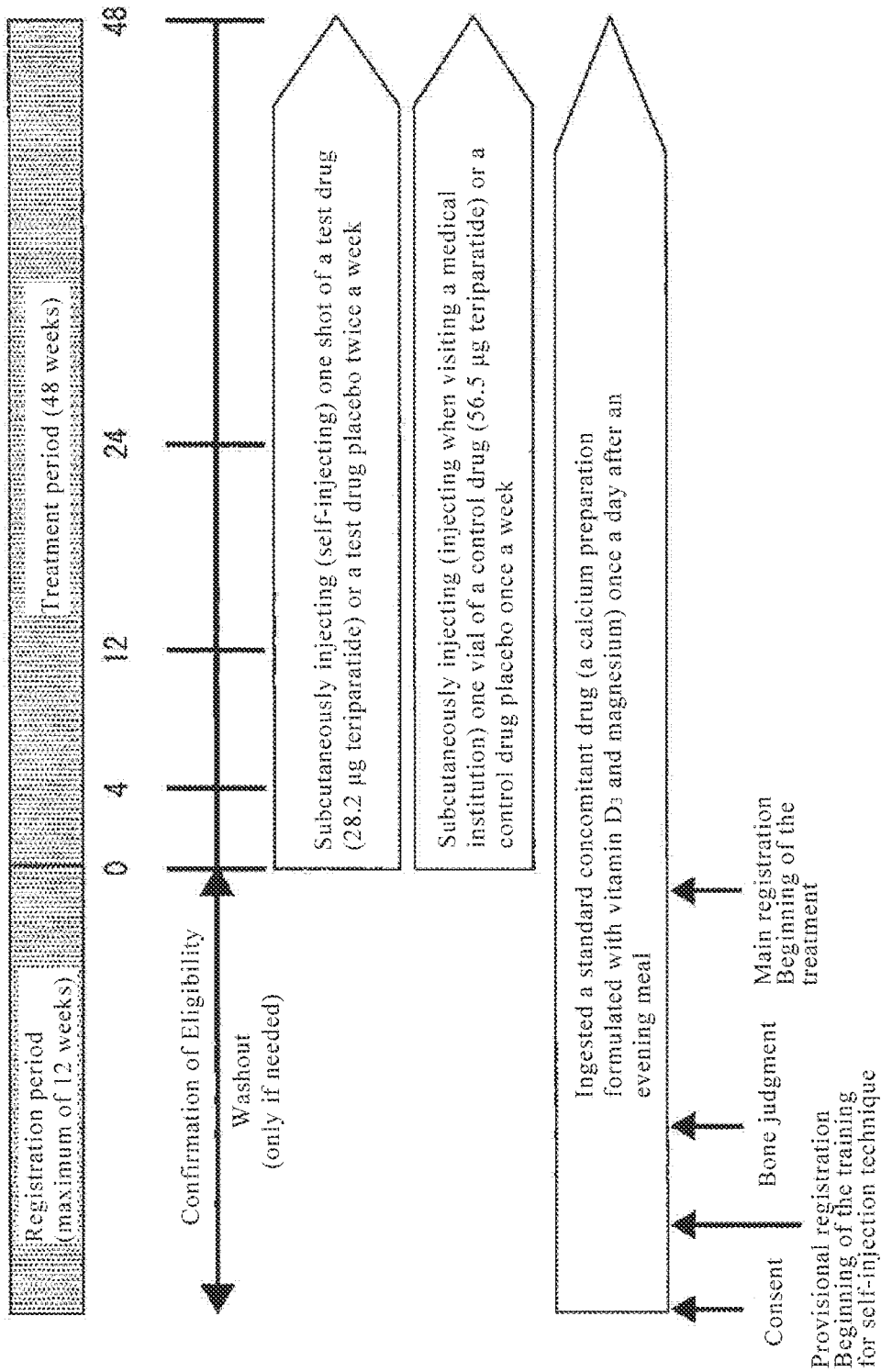
FIG. 3 is a chart schematically showing a treatment scheme in Working Examples of the present invention. In addition.

The present invention shall be described in detail hereinbelow on the basis of specific embodiments. However, the present invention is not intended to be bound to the following embodiments, and can be carried out in any embodiments within the range that would not depart from the spirit of the present invention.

(1) Teriparatide or Salt Thereof (Hereinafter Also Referred to as an Active Ingredient):

In the present invention, human PTH(1-34) is a peptide represented by a partial amino acid sequence consisting of amino acid residues of the position 1 to the position 34 from an N-terminal side in the amino acid sequence of human PTH(1-84) which is human parathyroid hormone.

]In the present invention, teriparatide means human PTH (1-34) in a free form. Teriparatide can also be in a salt form.

In the present invention, the salt of teriparatide includes any salts formed by teriparatide and one or more volatile organic acids. The volatile organic acids are exemplified by trifluoroacetic acid, formic acid, acetic acid, and the like. When teriparatide in a free form and the volatile organic acid form a salt, the ratio thereof is not particularly limited so long as the salt is formed. In particular, as the volatile organic acid, acetic acid is preferred. Specifically, the salt of teriparatide in the present invention is preferably exemplified by teriparatide acetate.

Teriparatide or a salt thereof can be produced by methods that themselves are known (for example, Patent Publications 1 to 3 and the like).

(2) Dosage:

The unit dose of the active ingredient, which is contained in the osteoporosis therapeutic and/or prophylactic agent of the present invention, or which is used in the method for treating and/or method for preventing osteoporosis of the present invention is preferably exemplified by, but not particularly limited to, as follows.

Specifically, the unit dose of the active ingredient is more preferably 20 μg or more, 25 μg or more, 27 μs or more, or 28 μg or more. In addition, the unit dose of the active ingredient which is contained in the osteoporosis therapeutic and/or prophylactic agent of the present invention is preferably 40 μg or less, and more preferably 35 μg or less, or 30 μg or less.

In particular, it is preferable that the unit dose of the active ingredient is 28.2 μg or 29.2 μg, in terms of teriparatide. When teriparatide used is an acetate, examples include the amount added with the acetate amount. For example, in a case where teriparatide pentaacetate is used, the unit dose of the active ingredient is preferably 30.3 μs or 31.3 μg, in terms of teriparatide acetate. Therefore, in the present invention, the phrase "teriparatide or a salt thereof . . . in a unit dose of 28.2 μg" means that a unit dose is an amount of 28.2 μg in terms of teriparatide, or an amount of 30.3 μg in terms of teriparatide acetate.

(3) Administration Frequency and Intervals of Administration:

One of the features of the osteoporosis therapeutic and/or prophylactic agent of the present invention and the method for treating and/or method for preventing osteoporosis of the present invention is in that the administration is carried out at a frequency of twice a week.

When the osteoporosis therapeutic agent or the like of the present invention is administered at a frequency of twice a week, the intervals of the administration in a week can be set at 1) a 1-day interval and a 6-day interval (a 0-day interval and a 5-day interval, when not including the days of administration), 2) at a 2-day interval and a 5-day interval (a 1-day interval and a 4-day interval, when not including the days of administration), or 3) at a 3-day interval and a 4-day interval (a 2-day interval and a 3-day interval, when not including the days of administration) (FIG. 1).

The intervals of administration in a week are not particularly limited, and an embodiment in which the intervals are a 3-day interval and a 4-day interval (a 2-day interval and a 3-day interval, when not including the days of administration) is most preferred.

An embodiment in which the intervals of administration in a week are a 3-day interval and a 4-day interval (a 2-day interval and a 3-day interval, when not including the days of administration) will be specifically described by administration schedule examples over two weeks from the initial administration. The administration of twice a week can be carried out in the week of the initial administration (week 1) by administration at Day 4 or Day 5 from the date of initial administration, and subsequently, the administration of twice a week in week 2 can be carried out by administration at Day 8, and administration at Day 11 or Day 12 (FIG. 2).

The time zone for the administration is not particularly limited, and the time zone may be during the day or may be at night. When the time zone for the administration is during the day, the administration may be administration in the morning, or administration in the afternoon or evening (in the p.m.). However, when used in combination with another therapeutic drug or basal drug (Ca, vD preparations or the like), it is more preferred that the ingestion time does not overlap with each other.

When the number of weeks of a period in which an osteoporosis therapeutic agent of the present invention or the like is administered at a frequency of twice a week is defined as n, and the number of weeks out of the n weeks in which the intervals of administration of twice a week are a 3-day interval and a 4-day interval (a 2-day interval and a 3-day interval, when not including the days of administration) is defined as m, $(m/n) \times 100 (\%)$ can be a given level or higher. The lower limit of the proportion is exemplified by 50%, 60%, 70%, 75%, 80%, 85%, 90%, or 95%, and the lower limit of the proportion is preferably 80% or more, and more preferably 90% or more.

For example, in a case where a period in which an osteoporosis therapeutic agent or the like of the present invention is administered at a frequency of twice a week is 34 days, and the number of weeks in which the intervals of administration of twice a week are a 3-day interval and a 4-day interval (a 2-day interval and a 3-day interval, when not including the days of administration) is 2, $(m/n) \times 100$ defined above would be calculated to be $2 \div (34 \div 7) \times 100$, i.e. about 41.2(%).

(4) Administration Route and Administration Sites:

The administration route for the osteoporosis therapeutic and/or prophylactic agent of the present invention and the method for treating and/or method for preventing osteoporosis of the present invention is not particularly limited, and the administration can be carried out intravenously, subcutaneously, or intramuscularly. In particular, the subcutaneous administration is preferably exemplified.

The administration sites for the osteoporosis therapeutic and/or prophylactic agent of the present invention and the method for treating and/or method for preventing osteoporosis of the present invention are not particularly limited, and for example, the administration can be carried out to upper arm parts, femur parts, or abdominal parts. However, in the second or subsequent administrations, it is preferable that the administration is carried out to a site at least 3 cm or so away from the previous administration site. In addition, the administration can be facilitated by pinching the surrounding of the administration site with a hand, and raising up the administration site and the surroundings thereof from the skin surface immediately before the administration.

(5) Period of Administration:

The period of administration for the osteoporosis therapeutic and/or prophylactic agent of the present invention and the method for treating and/or method for preventing osteoporosis of the present invention is not particularly limited, and the period of administration can be properly determined by the prescription of a physician in charge depending upon the patients or the like.

The lower limit of the period of administration is not particularly limited, and the period of administration is preferably exemplified by, for example, preferably 4 weeks or more, 8 weeks or more, 12 weeks or more, 24 weeks or more, 48 weeks or more, or 1 year or more. The upper limit of the period of administration is also not limited in the same manner, and the upper limit of the period of administration preferably includes, for example, within 5 years, within 4 years, within 3 years, or within 2 years.

(6) Diseases and Patients:

(6-1) Diseases:

One of the features of the osteoporosis therapeutic and/or prophylactic agent of the present invention and the method for treating and/or method for preventing osteoporosis of the present invention is in that administration is carried out for the purpose of treatment and/or prevention of osteoporosis.

The osteoporosis in the present invention means "a skeletal disease characterized by compromised bone strength predisposing a person to an increased risk of fracture" (Non-Patent Publication 1; the definition in Consensus Conference in NIH in 2000), which includes both primary osteoporosis and secondary osteoporosis.

The primary osteoporosis is exemplified by involutional osteoporosis (postmenopausal osteoporosis and senile osteoporosis), and idiopathic osteoporosis (post-pregnancy osteoporosis, juvenile osteoporosis, or the like). The secondary osteoporosis is osteoporosis triggered by a specified disease, a specified drug, and other causations. The causations include specified drugs, rheumatoid arthritis, diabetes, hyperthyroidism, sexual dysfunctions, immobility, nutrition, congenital diseases, and the like. The specified drugs include, for example, steroids. The diagnostic criteria for the primary osteoporosis are well known (Non-Patent Publication 10).

The osteoporosis in the present invention includes preferably osteoporosis with high risks of bone fractures. The osteoporosis with high risks of bone fractures may be patients with risk factors such as low bone mineral density, prevalent bone fractures, aging, and family history with bone fractures at the femoral neck parts (Non-Patent Publication 9).

As mentioned above, as drugs with efficacies and effects for osteoporosis with high risks of bone fractures, a daily administered preparation or a once-weekly administered preparation, each containing teriparatide or a salt thereof as an active ingredient, has been developed. After being approved for sales thereof, the preparation has been actually used in clinical situations.

In addition, as osteoporosis therapeutic agents with high risks of bone fractures, the development of human anti-sclerostin antibodies has been advanced. From these situations, one of ordinary skill in the art can easily and clearly recognize osteoporosis with high risks of bone fractures.

As a tool for assessing the absolute riskiness of bone fractures of individuals, FRAX (registered trademark) of the WHO (World Health Organization) has been known, which can calculate the incidence probability (%) of bone fractures in the future 10 years of the individuals. In the daily medical services, the tool can be used as a screening means for discriminating individuals with latent high risks of bone fractures in aged individuals without symptoms who are outpatients in the medical institutions.

(6-2) Patients:

The osteoporosis patients in the present invention can be osteoporosis patients with at least one or more of the risk factors for bone fractures mentioned above. The patients described above can be preferably exemplified by osteoporosis patients with three risk factors for bone fractures of aging, prevalent bone fractures, and low bone mineral density.

In addition, the osteoporosis patients in the present invention can be osteoporosis patients in which at least one risk factor out of the above risk factors for bone fractures satisfies specified conditions (for example, a specified threshold value or less, a specified threshold value or more, a specified numerical range, the presence or absence, or the like).

In particular, it is preferable that the osteoporosis patients in the present invention are osteoporosis patients with high risks of bone fractures. The osteoporosis patients with high risks of bone fractures as described above can be preferably exemplified by osteoporosis patients satisfying the following 3 conditions.

1) an age 65 years or older;
2) prevalent bone fractures of one or more; and
3) a bone mineral density of the lumbar vertebrae of less than 80% of the young adult mean (Young Adult Mean, which may also be referred to as YAM).

Here, the prevalent bone fractures include preferably prevalent vertebral bone fractures, and the number of prevalent bone fractures can be 1 or more and 5 or less. In addition, the prevalent vertebral bone fractures can be graded as prevalent vertebral bone fractures of a low-level deformation (grade 1), a mid-level deformation (grade 2), or a high-level deformation (grade 3) (Non-Patent Publication 9).

Specific examples of the grade 1 include low-level bone fractures in which the decrease is 20 to 25% in the centrum height; specific examples of the grade 2 include mid-level bone fractures in which the decrease is 25 to 40% in the centrum height; and specific examples of the grade 3 include high-level bone fractures in which the decrease is 40% or more in the centrum height, respectively.

The osteoporosis patients in the present invention can be osteoporosis patients that are not patients satisfying at least any one out of the following six conditions:
1) patients which are considered to have high risks of the incidence of osteosarcoma;
2) patients with hypercalcemia;
3) patients with primary malignant osteocarcinoma or metastatic osteocarcinoma;
4) patients with metabolic bone diseases other than osteoporosis;
5) patients with prevalence of hypersensitivity to an active ingredient of the osteoporosis therapeutic and/or prophylactic agent of the present invention or other teriparatide preparation; and
6) female adult who are pregnant or possibly pregnant.

The patients which are considered to have high risks of the incidence of osteosarcoma include, for example, patients with Paget's disease of the bone, patients showing high alkaline phosphatase values, patients in which epiphysical line is not closed in infants or the like and juvenile individuals, and patients that took radiation therapy which are considered to affect the bones in the past.

In addition, the osteoporosis patients in the present invention can be osteoporosis patients that are not patients satisfying at least any one of the following five conditions.
1) patients with low blood pressure;
2) patients with renal disorders;
3) patients with serious cardiac diseases;
4) patients with serious hepatic dysfunctions; and
5) patients with urinary calculus and patients with prevalence thereof.

Alternatively, the osteoporosis patients in the present invention can be osteoporosis patients having low-level or mid-level renal disorders. The normal renal function, renal dysfunctions, and the levels of disorders can be discriminated on the basis of the creatinine clearance. Specifically, a creatinine clearance of 80 mL/min or more can be judged as normal renal function, a creatinine clearance of 50 mL/min or more and less than 80 mL/min can be judged as a low-level renal dysfunction, and a creatinine clearance of 30 mL/min or more and less than 50 mL/min can be judged as a mid-level renal dysfunction. The method for calculating a creatinine clearance includes, for example, the formulas of Cockcroft-Gault (male: (140−age)×body weight/(72×serum creatinine value), female: 0.85×(140−age)×body weight/(72×serum creatinine value)) as an example.

In addition, the osteoporosis patients in the present invention can be osteoporosis patients that satisfy such that each of the factors respectively has specified conditions (for example, a specified threshold value or less, a specified threshold value or more, a specified numerical range, the kinds, the presence or absence, or the like), with respect to at least any one of the factors out of the following 18 factors which the patients have:
1) gender;
2) age;
3) height;
4) body weight;
5) BMI;
6) the number of years after menopause (limited to women, patients with menopause);
7) history of suffering from nonvertebral bone fractures at age 50 or older (limited to patients of age 50 or older);
8) history of suffering from nonvertebral bone fractures without accompanying external force at age 50 or older (limited to patients of age 50 or older);
9) prevalence that affects bone metabolism;
10) smoking;
11) alcohol consumption;
12) parental history of femoral bone fractures;
13) previous therapeutic drugs of osteoporosis;
14) 25-hydroxyvitamin D;
15) the number of prevalent vertebral bone fractures;
16) a bone mineral density of the lumbar vertebrae (value calculated as YAM) (%);
17) a bone mineral density at the femoral neck part (value calculated as YAM) (%); and
18) a bone mineral density of the total proximal parts of the femur (value calculated as YAM) (%).

For example, the osteoporosis patients in the present invention can be male or female patients; patients of age 65 years or older and younger than 75 years; patients of age 75 years or older and younger than 80 years; patients of age 80 years or older; patients with a bone mineral density of lumbar vertebrae (value calculated as YAM) (%) of less than 60%, those of 60% or more and less than 70%, or those of 70% or more and less than 80%; patients with the number of prevalent vertebral bone fractures of zero; patients with the number of prevalent vertebral bone fracture of one; patients with the number of prevalent vertebral bone fractures of two to three; patients with the number of prevalent vertebral bone fractures of four to five; patients with the number of prevalent vertebral bone fractures of six or more, or the like.

The osteoporosis patients in the present invention are osteoporosis patients in which each of the items of at least any one of items out of the following 26 investigational study items respectively satisfies specified conditions (for example, a specified threshold value or less, a specified threshold value or more, a specified numerical range, or the like).
1) blood general test items (a total of 6 items) (red blood cell count, hemoglobin, hematocrit, white blood cell count, white blood cell fraction, platelet count);
2) blood biochemical test items (a total of 14 items) (AST (GOT), ALT (GPT), alkaline phosphatase, total cholesterol, urea nitrogen, uric acid, creatinine, CPK, calcium, inorganic phosphorus, sodium, potassium, chlorine, albumin); and
3) urine test items (a total of 6 items) (occult blood, protein, sugar, urobilinogen, bilirubin, pH).

AST (GOT) as used herein means aspartate aminotransferase (glutamic-oxaloacetic transaminase)), and ALT (GPT) as used herein means alanine aminotransferase (glutamic-pyruvic transaminase)). Here, CPK as used herein means creatinine phosphokinase.

In addition, the osteoporosis patients in the present invention can be osteoporosis patients in which each of the items of at least any one of items out of the vital sign items (sitting systolic blood pressure, sitting diastolic blood pressure, pulse rate, and the like) respectively satisfies specified conditions (for example, a specified threshold value or less, a specified threshold value or more, a specified numerical range, or the like).

Alternatively, the osteoporosis patients in the present invention can also be osteoporosis patients which are capable of producing anti-drug antibodies (for example, antibodies against teriparatide or a salt thereof, and the like) and neutralizing antibodies (for example, antibodies capable of lowering or losing the activity of teriparatide or a salt thereof, and the like), with the ingestion of the osteoporosis therapeutic and/or prophylactic agent of the present invention.

In addition, the osteoporosis patients in the present invention can be osteoporosis patients in which each of the markers of at least any one of the markers out of the following 12 markers respectively satisfies specified conditions (for example, a specified threshold value or less, a specified threshold value or more, a specified numerical range, or the like).
1) blood markers (osteocalcin, P1NP, NTX, CTX, calcium, inorganic phosphorus, albumin, 25-hydroxyvitamin D fraction); and
2) urine markers (NTX, calcium, inorganic phosphorus, creatinine).

P1NP as used herein means procollagen type I aminoterminal propeptide, NTX as used herein means crosslinked N-telopeptide of type I collagen, and CTX as used herein means type I collagen crosslinked C-telopeptide, respectively.

The osteoporosis patients in the present invention include patients with a blood osteocalcin concentration of less than 15.2 (ng/mL), patients with a blood osteocalcin concentration of 15.2 (ng/mL) or more and less than 21.8 (ng/mL), and patients with a blood osteocalcin concentration of 21.8 (ng/mL) or more.

Alternatively, the osteoporosis patients in the present invention include, for example, a blood osteocalcin concentration of less than 14.8 (ng/mL), patients with a blood osteocalcin concentration of 14.8 (ng/mL) or more and less than 21.9 (ng/mL), and patients with a blood osteocalcin concentration of 21.9 (ng/mL) or more.

In addition, the osteoporosis patients in the present invention include, for example, patients with a blood P1NP concentration of less than 38.0 (μg/L), patients with a blood P1NP concentration of 38.0 (μs/L) or more and less than 58.5 (μs/L), and patients with those of 58.5 (μs/L) or more.

Alternatively, the osteoporosis patients in the present invention include, for example, patients with a blood P1NP concentration of less than 37.4 (μg/L), patients with a blood P1NP concentration of 37.4 (μs/L) or more and less than 57.3 (μs/L), and patients with those of 57.3 (μs/L) or more.

The osteoporosis patients in the present invention can also be patients having therapeutic history with previous therapeutic drugs for osteoporosis. The previous therapeutic drugs for osteoporosis include calcium drugs, female hormone drugs, SERMs (selective estrogen receptor modulators), active vitamin $D_3$ drugs, vitamin $K_2$ drugs, calcitonin drugs, parathyroid hormone drugs, bisphosphonate drugs, and denosumab.

Here, the SERMs are preferably exemplified by raloxifene and bazedoxifene; the active vitamin $D_3$ drugs are preferably exemplified by eldecalcitol, alfacalcidol, and calcitriol; and the vitamin $K_2$ drugs are preferably exemplified by menatetrenone, respectively. Further, the bisphosphonate drugs are exemplified by etidronate, alendronate, risedronate, minodronate, and ibandronate. The calcitonin drugs are exemplified by calcitonin salmon and elcatonin. The parathyroid hormone drugs include a daily administered preparation or a once-weekly administered preparation, containing teriparatide or a salt thereof mentioned above as an active ingredient.

In addition, the osteoporosis patients in the present invention can be osteoporosis patients suffering from other diseases, in other words, osteoporosis patients having complications. Other diseases include diabetes, hypertension, adipogenetic aberrancy (hyperlipemia or the like), chronic kidney diseases (CKD), rheumatoid arthritis, gout, hyperuricemia, dementia, cataract, senile hearing impairments, dysuria, cerebrovascular diseases, ischemic cardiac diseases, and the like.

Alternatively, the osteoporosis patients in the present invention can also be osteoporosis patients who are in a care-needed state.

(7) Combination Use:

The osteoporosis therapeutic and/or prophylactic agent of the present invention and the method for treating and/or method for preventing osteoporosis of the present invention can be used in combination with other drugs. Other drugs can be administered in the identical or different routes, simultaneously or successively (i.e., at separate time) with the osteoporosis therapeutic and/or prophylactic agent of the present invention.

Other drugs include at least one of the drugs in the previous therapeutic drugs for osteoporosis mentioned above. Alternatively, other drugs also include a therapeutic and/or prophylactic agent for complications mentioned above. In addition, other drugs may be a basal drug (Ca, vD preparations, and the like).

Preferred basal drugs include $vD_3$ (vitamin $D_3$) preparations, magnesium preparations, and calcium preparations. These basal drugs can be used together in any combinations, and they may be in the form of a combination preparation. For example, calcium preparations formulated with $vD_3$ and magnesium are preferably exemplified as a basal drug. The combination preparation as described above is preferably ingested once a day after an evening meal, the combination preparation containing $vD_3$ 400 IU, magnesium 30 mg, and calcium 610 mg per dose.

When the osteoporosis therapeutic and/or prophylactic agent of the present invention is subjected to a clinical test as a test drug, the evaluation can also be carried out in the state that the test individuals are ingested with the above or equivalent basal drug (Non-Patent Publication 15). Here, the considerations can be made to the ideas that the decrease in the risks of bone fractures by a combined use of vD and a calcium preparation is indefinite (Non-Patent Publication 25), and that when both the test drug group and the control drug group are given with a basal drug, the influences of the basal drug in the differences between the two groups on efficacies and safety are not probably substantially recognized. In view of these ideas, when the osteoporosis therapeutic and/or prophylactic agent of the present invention is used in a clinically practiced site, the use of vD and a calcium preparation is not necessarily needed.

(8) Preparation:

The osteoporosis therapeutic and/or prophylactic agent of the present invention can take various preparation forms. In general, it is preferable that the present preparation is in the form of an injection containing pharmaceutically acceptable excipients and additives, from the viewpoint of safety or the like.

The excipients and the additives are not particularly limited, including, for example, a sugar alcohol (mannitol or the like), an inorganic salt (sodium chloride or the like), a saccharide (sucrose or the like), or an amino acid (methionine or the like). The present preparation may contain a buffer, or may not contain a buffer. The pH of the present preparation can be appropriately adjusted, and the pH can be adjusted to, for example, from 3.5 to 5.5.

The concentration of the active ingredient in the present preparation is also not particularly limited, and the concentration can be, for example, 50 µg/mL or more, and can also be from 100 to 200 µg/mL.

When the present preparation is in the form of an injection, the present preparation can be produced by dissolving an active ingredient, excipients and additives in a proper solvent (sterile water, a buffer, physiological saline or the like), subjecting the solution to filtration with a filter or the like and/or sterile treatment, and subsequently dispensing and sealing the filtrate in a container previously cleaned and subjected to sterile treatment.

Here, examples of the dispensing container include, for example, ampules, vials, pre-filled syringes, bags, and the like. The materials for the container include, but not particularly limited to, glass and plastics. The materials for the container are preferably exemplified by plastics, from the viewpoint of strength, easiness in handling, safety, and the like.

For example, the preparation may be an automatically administered preparation in which a pre-filled syringe with a needle which is previously dispensed with a drug solution is incorporated into an auto-injector. Since the osteoporosis therapeutic agent or the like according to the present invention shows sufficient safety, the preparation can serve as an automatically administered preparation for domiciliary care.

(9) Efficacies:

The main purpose of the therapeutic and/or prophylactic agent for osteoporosis according to the present invention and the method for treating and/or method for preventing osteoporosis of the present invention is to prevent or inhibit bone fractures.

(9-1) Prevention or Inhibition of Bone Fractures:

The bone fractures in the present invention include pathological bone fractures caused by osteoporosis, osteogenesis imperfecta, bone tumor, or the like, and traumatic bone fractures caused by traffic accidents, bruises, or the like. The bone fractures preferably include bone fractures caused by osteoporosis.

The bone fractures in the present invention include both vertebral bone fractures and non-vertebral bone fractures. The non-vertebral bone fractures include, but also not particularly limited to, for example, bone fractures in the proximal part of the femur, the distal end of the radius, the proximal part of the humerus, the tibiae, pelvis, costa, and the like. The bone fractures in the present invention preferably include vertebral bone fractures (new vertebral bone fractures, worsening vertebral bone fractures, and the like).

In general, the femoral proximal fractures mean hip fractures of elderly individuals, which are understood to be bone fractures that are different from the fractures of the proximal part of the femur (Non-Patent Publication 9). The bone fractures that are included in the femoral proximal fractures include, for example, subchondral insufficiency fracture of the femoral head, femoral neck fracture, basal neck fracture of the femur, trochanteric fracture of the femur, and subtrochanteric fracture of the femur (Non-Patent Publication 9).

Here, since the subchondral insufficiency fracture of the femoral head is very rare and the diagnosis of the basal neck fracture of the femur is difficult, they can also be classified into either one of femoral neck fracture and trochanteric fracture of the femur. Since the distinctions between the trochanteric fracture of the femur and the subtrochanteric fracture of the femur are not clear, it is also possible to employ a method of roughly classifying the femoral proximal fractures into two groups of the femoral neck fracture and the trochanteric fracture of the femur (Non-Patent Publication 9). The femoral proximal part may be also referred to a femoral proximal total, from the implications of emphasizing its totality.

The vertebral bone fractures have a very high clinical significance in the prevention or inhibition thereof because the vertebral bone fractures are osteoporosis bone fractures with the highest frequency and the vertebral bone fractures are important as an index for diagnosis and treatment of osteoporosis (Non-Patent Publication 9). In addition, since the femoral proximal fractures cause the worsening of life functions or the QOL and the femoral proximal fractures are considered to also be relevant to life prognosis (Non-Patent Publication 9), it is preferable that measures for sufficient prevention or inhibition are taken against the femoral proximal fractures.

The vertebral bone fractures can be judged as morphometric bone fractures according to the level of degree of deformation of vertebrae irrelevant to the presence or absence of clinical symptoms (Non-Patent Publication 9). The morphometric bone fractures can be classified into prevalent bone fractures and new bone fractures.

The new bone fractures can be defined as bone fractures which are judged as new incidence by comparing X-ray images or the like at two time points, and the prevalent bone fractures can be bone fractures which are judged by the extent of deformation of the centrum at one time point before the beginning of the treatment. Of the new bone fractures, those in which the centrum that has not undergone deformation before the beginning of the treatment is deformed after the beginning of the treatment are defined as new vertebral bone fractures, which can also be distinguished from worsening bone fractures that are those in which the extent of deformation of the centrum is increased after the beginning of the treatment. The new vertebral bone fractures and the worsening vertebral bone fractures as used herein are expressed in the distinctions as mentioned above.

The vertebral bone fractures in the present invention include both new vertebral bone fractures and worsening vertebral bone fractures. For example, the extent of the deformation of the centrum can be classified according to Grades in view of the forms of the total centrum, which is generally classified as Grade 0 (normal), Grade 1 (decrease of about 20 to about 25% in the centrum height, and decrease of 10 to 20% in the centrum area), Grade 2 (decrease of about 25 to about 40% in the centrum height, and decrease of 20 to 40% in the centrum area), and Grade 3 (decrease of about 40% or more in the centrum height, and decrease of 40% or more in the centrum area). The distinctions of new and worsening can be carried out in line with the increase patterns of Grade in accordance with the judgment criteria of Genant. Specifically, in cases where a change is found from Grade 0 to Grade 1, 2, or 3, it is diagnosed as a new vertebral bone fracture, and in a case where a change is found from Grade 1 to Grade 2 or 3, or from Grade 2 to Grade 3, it can be considered as a worsening bone fracture.

Of the bone fractures in the present invention, bone fractures which are diagnosed with clinical symptoms such as pains can be referred to as clinical bone fractures, and the clinical bone fractures can be classified into clinical vertebral bone fractures and clinical non-vertebral bone fractures. The clinical non-vertebral bone fractures as used herein are simply referred to as non-vertebral bone fractures. The clinical symptoms are, for example, acute pains of dorsolumbar parts, and the like, which can be confirmed by appeals made by the test individuals.

The bone fracture assessment method using an X-ray image or MRI is a method that itself is known, and, for example, a quantitative assessment method (QM method) or a semi-quantitative assessment method (SQ method) has been known. The SQ method is a method proposed by Genant et al. in 1993, which has been so far used in many clinical tests in Japan or elsewhere, and the evidences thereof have been constructed, so that the method can be more preferably used (Non-Patent Publication 11). Besides them, a method by Wu et al. or a method by Fukunaga et al. can also be used (Non-Patent Publications 11 to 13).

When the osteoporosis therapeutic and/or prophylactic agent is tested, it is preferable that the bone fracture inhibitory action thereof is assessed. When the bone fracture inhibitory action of a test drug is assessed, the bone fracture inhibitory action (bone fracture risk reducing property or the like) of the test drug can be also assessed in the same test without using a placebo control drug in the same test by subjecting a control drug which is found to have bone fracture inhibitory property by past clinical data or the like to a test and carrying out the same test to obtain a bone fracture incidence rate of the control drug, and comparing a bone fracture incidence rate of a test drug with a bone fracture incidence rate of a control drug, or by comparing a bone fracture incidence rate of a test drug with a bone fracture incidence rate without treatment for test individuals of the same test which can be assumed on the basis of the past clinical data or the like.

(9-2) Increase in Bone Mineral Densities:

The bone strength is made up of two factors, bone mineral density and bone quality, and in general, the "bone mineral density" can account for about 70% of the bone strength, and the "bone quality" can account for the remaining 30% or so (Non-Patent Publication 9). Even in a daily administered preparation or a once-weekly administered preparation, the preparation containing teriparatide or a salt thereof as an active ingredient, not only the bone fracture inhibitory effects but also bone mineral density increasing effects have been known (Non-Patent Publications 4, 5, 8, and 9).

Here, the bone mineral density refers typically to a bone mineral content of the lumbar vertebrae. The lumbar vertebrae are rich in trabecular bones having a fast bone turnover, so that the sensitivity of a detection change of the change in bone mineral densities by a drug therapy is also high. In addition, in a case where the assessment of the bone mineral content of the lumbar vertebrae is difficult or the like, the bone mineral density can be expressed by the bone mineral content values of the radius, the second metacarpal bone, the femoral neck part, or the calcaneus. In addition, the young adult mean infers to a mean value of bone mineral densities of ages 20 to 44 years.

The bone mineral density can be measured by methods that are themselves known, for example, dual-energy X-ray absorptiometry, photodensitometry, photon absorptiometry, quantitative CT scan, quantitative ultrasonography, and the like.

The change rate in bone mineral densities can be calculated by, for example, the following formula:

$$\text{Change rate in bone mineral densities}(\%) \text{ at a certain time point } a = \frac{\begin{pmatrix} \text{Bone mineral} \\ \text{density at the} \\ \text{time point} \end{pmatrix} - \begin{pmatrix} \text{Bone mineral} \\ \text{density at the} \\ \text{beginning of} \\ \text{administration} \end{pmatrix}}{\begin{pmatrix} \text{Bone mineral} \\ \text{density at the} \\ \text{beginning of} \\ \text{administration} \end{pmatrix}} \times 100$$

In addition, the degree of bone atrophy in the present invention means a degree of loss in bone mass on an X-ray. The degree of bone atrophy is classified into no bone atrophy, bone atrophy grade I, bone atrophy grade II, and bone atrophy grade III. No bone atrophy in the degree of bone atrophy refers to a normal condition, which specifically means a condition in which the trabecular structure cannot be recognized because latitudinal and longitudinal trabeculae are dense. Bone atrophy grade I means that longitudinal trabeculae are prominent. Typically, it means a condition in which the longitudinal trabeculae are thin and visible but still arranged densely, and the end plates of the centrum are prominent. Bone atrophy grade II in the degree of bone atrophy means a state in which the longitudinal trabeculae have become rough, appear thick, and are roughly arranged, and the end plates of the centrum also have lighter color. Bone atrophy grade III in the degree of bone atrophy means a condition in which the longitudinal trabeculae become indistinct, the centrum shadows appear blurry as a whole, and the difference from the shadows of the intervertebral disks is reduced. The degree of bone atrophy can be judged, for example, from a lateral X-ray image of the lumbar vertebrae.

(9-3) Fluctuations in Bone Metabolism Markers:

The fluctuations in the bone metabolism markers are associated with the prevention or inhibition of bone fractures and increase in bone mineral densities. Therefore, when the osteoporosis therapeutic agent is assessed or the like from the aspect of efficacies, it is considered to be useful to measure bone metabolism marker values in biological samples (blood samples, urine samples, and the like) derived from test individuals, and confirm the fluctuations thereof (for example, differences between values before the administration and values after the administration) (Non-Patent Publication 9).

For the purpose of assessing the osteoporosis therapeutic and/or prophylactic agent of the present invention in the aspect of efficacies, the fluctuations of bone metabolism markers, the increase in bone mineral densities, or the inhibition of bone fractures can be observed. In an administration embodiment where a method of administration is twice a week in the present invention in which the intervals of the administration in a week are a 2-day interval and a 3-day interval (not including the days of administration), it is preferable that the efficacies are assessed by directly observing the increase in bone mineral densities or the inhibition of bone fractures.

The bone metabolism markers are roughly classified into bone formation markers and bone resorption markers. The bone formation markers can be substances that are directly or indirectly produced from osteoblasts at each stage of differentiation of the osteoblasts, and osteocalcin, P1NP or the like has been known. The bone resorption markers can be substances that are related to activation or bone resorption of osteoclasts, and NTX, CTX or the like has been known.

Conventionally, regarding a daily osteoporosis therapy using teriparatide, particularly at an early stage, the dissociation of the bone formation markers which are found to have a rapid increase from the beginning of administration and the bone resorption markers is called "anabolic window," which has been considered to the mechanism of increase in bone mineral densities from an early stage of administration (Non-Patent Publication 24). Also in the osteoporosis therapeutic and/or prophylactic agent of the present invention, the fluctuations of the bone metabolism markers, for example, "Anabolic window" can serve as an index for therapeutic monitoring particularly at an early stage of the beginning of administration (for example, within several months from the beginning of administration).

However, the administration embodiment where a method of administration of twice a week in the present invention in which the intervals of the administration in a week are a 2-day interval and a 3-day interval (not including the days of administration) can be clearly distinguished from the conventional teriparatide therapeutic method with regard to the relationship between the bone metabolism markers and the efficacies. Therefore, when the efficacies are assessed in the same administration embodiment, it is more preferable that the increase in bone mineral densities or the inhibition of bone fractures is directly observed, not the fluctuations of the bone metabolism markers.

Further, according to the studies on rats subjected to ovariectomy which are widely used as osteoporosis models (Non-Patent Publications 14 and 15), it has been reported that the voids in the cortical bone are increased according to the dosage when the dosage frequency of teriparatide is high (Non-Patent Publication 14).

In addition, it has been reported that teriparatide has been used as a therapeutic agent for osteoporosis with a high risk of bone fractures, and the voids in the cortical bone are increased in the subject patients by aging or pathologies, and it has been reported that the therapeutic strategies in considerations of pathologies of the patients and the features of the pharmacological actions of teriparatide are needed in order to maximize the therapeutic effects with teriparatide (Non-Patent Publication 14).

Therefore, in the treatment or prevention in the present invention, an embodiment such that a blood concentration or a urine concentration of the bone resorption markers which are deeply related with the void formation or porosity in the cortical bone is reduced with the time course or the increase is inhibited with the time course, while increasing the bone formation markers associated with an increase in bone mineral densities and a bone fracture inhibitory rate is preferred. The bone resorption markers which are deeply related with the void formation or porosity in the cortical bone can be exemplified by NTX and CTX. Moreover, an embodiment of the present invention as described above can be an embodiment in which the intervals between administrations are appropriately taken so as not to continuously increase bone resorption when repeatedly administered. More specifically, for example, the treatment or prevention in which a dosage is 28.2 µg, in terms of teriparatide, is exemplified, among which a method of administration twice a week in the present invention (provided that a unit dose is 28.2 μg in terms of teriparatide), in which the intervals of administration in a week are a 2-day interval and a 3-day interval (not including the days of administration), is preferably exemplified.

(10) Safety:
(10-1) Adverse Events and Side Effects:

All the unwanted or unintended diseases or symptoms thereof caused in individuals administered with a drug can be referred to as adverse events (AE).

Among the adverse events, those in which cause-and-effect relationship with a drug cannot be denied can be referred to as side effects. The matter that the cause-and-effect relationship cannot be denied includes the matter that a reasonable possibility of the cause-and-effect relationship is found, and the matter that no reasonable possibilities of the cause-and-effect relationship cannot be assessed.

The adverse events can be roughly classified into serious adverse events and non-serious adverse events, and the following six adverse events can be defined as serious adverse events, and the adverse events other than the serious adverse events can be defined as non-serious adverse events.
1) those leading to death (death);
2) those threatening life (risks of death);
3) those in need of hospitalization for the treatment or extension of the hospitalization period (hospitalization or extension of the hospitalization period);
4) those suffering from persistent or marked disorders or dysfunctions (disorders);
5) those having congenital aberrancy (congenital aberrancy); and
6) other medically important conditions (risks of disorders, seriousness in accordance with the above 1) to 4)).

In addition, in addition to the seriousness and the cause-and-effect relationships, the adverse events can be roughly classified by the levels of the adverse events. For example, the following three levels can be considered.
1) low-level: a level that is transient and easily durable;
2) mid-level: a level that has some hindrances in an ordinary activity; and
3) high-level: a level that makes it impossible to perform an ordinary activity.

Alternatively, the adverse events can also be classified in terms of the outcomes of treatment as, for example, being recovered/resolved, recovering/resolving, being not recovered/not resolved, being recovered/resolved with sequelae, being dead, and unknown, from the viewpoint of changes in the time course.

The method when a certain drug is compared with a different drug in safety is not particularly limited. For example, a certain adverse event is remarked, and the comparisons can be made with respect to expression frequency, seriousness, cause-and-effect relationship, the outcomes of treatment, and/or levels. Alternatively, both the drugs can be compared from the viewpoint of administration discontinuation caused by the entire or a part of the adverse events or the entire or part of the side effects.

The adverse events can include abnormality in clinical test values and vital signs.

The adverse events are not particularly limited, and can be classified according to the System Organ Class (SOC). The System Organ Class in connection with the adverse events is exemplified by the following.
1) infections and infestations;
2) gastrointestinal disorders;
3) musculoskeletal and connective tissue disorders;
4) injury, poisoning and procedural complications;
5) general disorders and administration site conditions (general and systemic disorders and administration site conditions);
6) skin and subcutaneous tissue disorders;
7) nervous system disorders;
8) respiratory, thoracic and mediastinal disorders;
9) eye disorders;
10) metabolism and nutrition disorders;
11) investigations (investigational studies);
12) neoplasms benign, malignant and unspecified (incl cysts and polyps);
13) ear and labyrinth disorders;
14) cardiac disorders; and
15) vascular disorders.

The adverse events classified as the "infections and infestations" can be exemplified by epipharingitis and influenza. The adverse events classified as the "nervous system disorders" can be exemplified by headaches and free-floating dizziness. The adverse events classified as the "respiratory, thoracic and mediastinal disorders" can be exemplified by inflammations in the upper airway. The adverse events classified as the "gastrointestinal disorders" can be exemplified by nausea, vomiting, constipation, or the like. The adverse events classified as the "skin and subcutaneous tissue disorders" can be exemplified by eczema. The adverse events classified as the "musculoskeletal and connective tissue disorders" can be exemplified by osteoarthritis. The adverse events classified as the "general and systemic disorders and administration site conditions" can be exemplified by malaise, bleeding at injected sites, and fervescence. The adverse events classified as the "injury, poisoning and procedural complications" can be exemplified by contusion.

As mentioned above, it has been also reported that nausea, vomiting, headaches, or the like is often observed by the administration of teriparatide acetate (Non-Patent Publication 9). In addition, in clinical tests using a daily administered preparation containing teriparatide or a salt as an active ingredient, it has been reported that dizziness is significantly high as compared to that of the placebo group (Non-Patent Publication 9). Further, it has also known to show shocks, or unconsciousness or the like accompanying a transient drastic blood pressure drop, from immediately after the administration to several hours of a daily administered preparation or a once-weekly administered preparation, each containing teriparatide or a salt thereof as an active ingredient (Non-Patent Publications 4 and 8).

Therefore, in the treatment or prevention in the present invention, an embodiment in which the expression frequency, the seriousness, and/or the levels of at least any one of the adverse effects or side effects out of adverse events or side effects such as nausea, vomiting, headaches, or the like, (free-floating) dizziness, shocks, a pressure drop, or unconsciousness is inhibited as much as possible is preferred.

(10-2) Therapeutic Continuality:

As mentioned above, in general, it has been reported that the drug ingestion situations in drug therapies for osteoporosis are such that 52.1% of the individuals undesirably drop out from the ingestion within 5 years after the beginning of the treatment, and there are some disadvantages addressed to the lowering in the inhibition of bone fractures, the increase in needs of use of facilities, and stagnancy in medical cost reductions due to lack of compliance to drug ingestions (Non-Patent Publication 9). Factors associated with the failure to the compliance to the drug ingestions are exemplified by the presence of pains, side effects, drugs ingested for gastrointestinal disorders, and the like (Non-Patent Publication 9). On the other hand, the preparation containing teriparatide or a salt thereof as an active ingredient has been addressed in the lowness in the therapeutic continuality, and it has been reported that the therapeutic continuality rate over a period of 12 months is 34.9% (Non-Patent Publication 22).

Therefore, providing a drug therapy with teriparatide or a salt thereof, the therapy exhibiting an even higher therapeutic continuality rate is considered to have a publicly high significance in social welfare and medicinal economy beyond the living improvements in the individual patients.

In view of the above, in the treatment or prevention in the present invention, an embodiment showing a high therapeutic continuality rate is preferred.

EXAMPLES

The present invention will be described more specifically hereinbelow by means of Working Examples, without intending to bind the present invention to those following Working Examples, and can be carried out in any embodiments within the range which does not depart from the spirit of the present invention.

Working Example 1

1. Test Method:

Test individuals were randomly assigned to either one of Test Drug Group and Control Drug Group. As shown in FIG. 3, each test individual of Test Drug Group was subcutaneously administered with a test drug and a control drug placebo, and each test individual of Control Drug Group was subcutaneously administered with a control drug and a test drug placebo, over 48 weeks in accordance with a double blind method (a double dummy method). In addition, the test individuals of both the groups ingested two tablets of a standard concomitant drug at a frequency of once a day after an evening meal.

In a case where each test individual uses an osteoporosis therapeutic agent within 8 weeks before the obtainment of the consent for the investigational studies, those test individuals were subjected to a washout. Upon washout, the following day of a final ingestion or the day of injection of the previous therapeutic agent for the treatment of osteoporosis is defined as Day 1 of washout, and it is considered to be acceptable if the beginning day of the investigational studies with the investigational product is on or after 8 weeks (56 days) of the washout. However, as a general rule, the beginning of the treatment with an investigational product did not exceed 12 weeks (84 days) from the obtainment of the consent.

When a physician in charge of the investigational studies or a contributory physician of the investigational studies discontinued the investigational studies for the test individuals when it was acknowledged that test individuals met given criteria after the beginning of the treatment with an investigational product. The given criteria were adverse events, lack of effects, impossibility of tracking studies, judgments by the physician in charge of the investigational studies or the contributory physician of the investigational studies, serious departure from the protocol of the investigational studies, compliance failures to the administration of an investigational product, proffers by test individuals, or judgments of the individuals that requested for the investigational studies.

1.1. Test Drug:

A test drug was an auto-injector preparation containing 0.2 g of a drug solution in one shot, and when an entire amount of a single shot of the preparation was administered, 28.2 μg in terms of teriparatide (30.3 μg in terms of teriparatide acetate) was administered. The drug solution is previously filled in a prefilled syringe with a needle incorporated in the auto-injector, the auto-injector being a tool used in subcutaneous injection of a drug solution to human bodies.

1.2. Test Drug Placebo:

A test drug placebo is an auto-injector preparation which is not distinguishable in external comparison from a test drug, the preparation not substantially containing teriparatide.

1.3. Control Drug:

A control drug is a vial preparation, which is a freeze-dried preparation for injection containing 63.3 μg in terms of teriparatide (67.9 μg in terms of teriparatide acetate) in one vial. Here, a control drug is a preparation with which 56.5 μg in terms of teriparatide is administered, when a drug solution obtained by adding 1 mL of Japanese Pharmacopoeia physiological saline to the drug to dissolve is administered with a syringe.

1.4. Control Drug Placebo:

A control drug placebo is a freeze dried preparation for injection which is not distinguishable in external comparison from a test drug, the preparation not substantially containing teriparatide.

1.5. Standard Concomitant Drug:

A standard concomitant drug is a calcium preparation formulated with vitamin $D_3$ and magnesium (New CAL-CICHEW (registered trademark) $D_3$; manufactured and sold by Nitto Pharmaceutical Industries, Ltd., and sold by Takeda Pharmaceuticals Company, Limited). Two tablets of the standard concomitant drug contain precipitated calcium carbonate 1,525 mg (610 mg, in terms of calcium), magnesium carbonate 118.4 mg (30 mg, in terms of magnesium), cholecalciferol 400 IU (vitamin $D_3$), and various additives.

1.6. Frequency of Twice A Week:

The intervals of administration at a frequency of twice a week are, in principle, three-day to four-day-intervals (two day- or three day-intervals between administrations). The intervals of administration (three day- or four day-interval) in principle as used herein mean that when the day of administration of either one of administration out of the two consecutive administrations was defined as Day 1, the day of the other administration was Day 4 or Day 5. For example, when administered on Monday of a certain week, the next day of administration would be, in principle, on Thursday or Friday, as shown below.
(One Example of Administration Intervals in General Rule)
Monday, Day 1, administered
Tuesday, Day 2
Wednesday, Day 3
Thursday, Day 4 or Friday, Day 5, administered 1.7. Test Individuals:

Test individuals were osteoporosis patients with all of the three bone fracture risk factors of "aging," "prevalent bone fractures," and "low bone mineral density." More specifically, test individuals were patients with primary osteoporosis that satisfied all the following conditions (1) to (6) (satisfying the selected criteria), but did not satisfy any one of the following conditions (7) to (25) (satisfying the exclusion criteria). Since the test individuals are osteoporosis patients with all of the three bone fracture risk factors of "aging," "prevalent bone fractures," and "low bone mineral density" (satisfying the following conditions (2) to (4)), the test individuals are osteoporosis patients with high risks of bone fractures.

[1] Selected Criteria:

(1) patients diagnosed as primary osteoporosis on the basis of Genpatsusei Kotsusoshoshou no Shindan Kijun (*Diagnostic Criteria for Primary Osteoporosis*) (Revised edition of the fiscal year of 2012);

(2) men and women of ages 65 years or older at the time of the obtainment of the consent;

(3) patients with prevalent bone fractures of one or more and within five at Th4 to L4 vertebrae (fourth thoracic vertebra to fourth lumbar vertebra) of the centrum;

(4) patients with a bone mineral density at lumbar vertebrae (L2 to L4) less than 80% of a young adult mean at the time of provisional registration;

(5) self-ambulatory outpatients; and (6) patients that have learned self-injection techniques before the initial administration of a test drug or the like, so that a physician in charge of the investigational studies or a contributory physician of the investigational studies judged that the patients are competent of managing and administering a test drug or the like.

[2] Exclusion Criteria:

(7) patients diagnosed as secondary osteoporosis;

(8) patients with diseases showing the loss in bone mass other than osteoporosis;

(9) patients having the following X-ray findings which are considered to influence in the assessment of bone mineral density of lumbar vertebrae:

found to have a high level of bone fractures of lumbar vertebrae in any one of lumbar vertebrae L2 to L4;

found to have a high level of osteosclerosis in any one of lumbar vertebrae L2 to L4;

found to have a high level of scoliosis, lordosis, or kyphosis;

found to have a high level of changes in spondylitis deformans; and others that the bone assessment committee members judged as inappropriate such as admixture of foreign matters.

Here, the "bone assessment committee members" refer to committee members which constitute "the bone assessment committee" which has been founded for the purpose of equally assessing the assessment of bone mass and the assessment of bone fractures of all the patients. Each of the assessment committee members is constituted by experts of imaging diagnosis for osteoporosis.

(10) patients to which a surgery of the centrum is previously operated;

(11) patients that are appealing for acute pains so as to be in suspect of vertebral bone fractures {patients with expressing or intensifying acute lumbago or backache from a period of 12 weeks (84 days) before the obtainment of the consent to the beginning day of treatment that need resting and additional therapy such as an antiphlogistic painkiller};

(12) patients that were judged to have low reliability of diagnosis by physician's inquiries on conditions of patients (at least patients with cognitive impairment being excluded);

(13) patients with serious renal diseases, hepatic diseases, or cardiac diseases (provided that the term "serious renal diseases" as used herein means those showing a serum creatinine value by a test defined before provisional registration of 2 mg/dL or more, the term "serious hepatic diseases" means those showing AST(GOT) or ALT(GPT) value by a test defined before provisional registration of 2.5 times or more the upper limit of the standard value or 100 IU/L or more, and the term "serious cardiac diseases" means those that are judged in reference to grade 2 shown in "*Iyakuhin no Fukusayo no Jutokudo Bunrui Kijun nitsuite* (*Classification Criteria for Degree of Seriousness of Side Effects of Pharmaceuticals*) (Yaku-an hatsu (PSEHB/PSD Notification) No. 80 dated Jun. 29, 1992)."

(14) patients with physical constitutions that are likely to cause hypersensitivity symptoms such as bronchial asthma and rashes (erythema, wheal, and the like);

(15) patients with a serum calcium value of 11.0 mg/dL or more according to a test defined before provisional registration;

(16) patients with an alkaline phosphatase value of double or more of the upper limit of the standard values according to a test defined before provisional registration;

(17) patients with Paget's disease of the bone;

(18) patients with complications or prevalence of primary malignant osteocarcinoma or metastatic osteocarcinoma;

(19) patients with complications of malignant osteocarcinoma or with prevalence within the past 5 years;

(20) patients who were subjected to radiotherapy which is considered to influence the bones in the past;

(21) patients subjected to administration of a teriparatide preparation or an anti-RANKL antibody preparation in the past;

(22) patients subjected to administration of a bisphosphonate preparation within 52 weeks (364 days) before the obtainment of the consent (however, in a drug which is set to have a certain period of intervals in the usage of the drug, the number of days are the 52 weeks (364 days) before the obtainment of the consent added with the period);

(23) patients administered with other investigational products within 26 weeks (182 days) before the obtainment of the consent;

(24) patients subjected to administration of the following (A) to (G) osteoporosis therapeutic agents on the day of obtainment of the consent (however, patients are considered as selectable as subjects if it is possible to perform washout of 8 weeks (56 days) or more before the beginning of the treatment (meaning a resting drug for the purpose of eliminating the influences of the previous therapeutic agent):

(A) a calcitonin preparation;

(B) an active vitamin $D_3$ preparation;

(C) a vitamin K preparation;

(D) an ipriflavone preparation;

(E) an estrogen preparation;

(F) an SERM preparation; and (G) an anabolic hormone preparation; and

(25) Other patients that a physician in charge of the investigational studies or a contributory physician of the investigational studies judged to be inappropriate in carrying out the present investigational studies.

1.8. Administration to Test Drug Group and Control Drug Group:

Test individuals were randomly assigned to either one of Test Drug Group and Control Drug Group. As shown in FIG. 3, each test individual of Test Drug Group was subcutaneously administered with a test drug and a control drug placebo, and each test individual of Control Drug Group was subcutaneously administered with a control drug and a test drug placebo, over 48 weeks in accordance with a double blind method (a double dummy method). In addition, the test individuals of both the groups ingested two tablets of a standard concomitant drug at a frequency of once a day after an evening meal.

Each patient assigned to Test Drug Group was subcutaneously injected with a single shot of a test drug twice a week (self-injected at any one of sites of upper arm parts, femur parts, and abdominal parts). The intervals of administration in a general rule were three to four days (two day- or three day-intervals between administrations). Further, the same patients were subcutaneously injected once a week (injected upon visits to medical institutions) with a solution obtained by dissolving one vial of a control drug placebo in 1 mL of Japanese Pharmacopoeia physiological saline upon use.

Each patient assigned to Control Drug Group was subcutaneously injected with a single shot of a test drug placebo twice a week (self-injected at any one of sites of upper arm parts, femur parts, and abdominal parts). Further, the same patients were subcutaneously injected once a week (injected upon visits to medical institutions) with a solution obtained by dissolving one vial of a control drug in 1 mL of Japanese Pharmacopoeia physiological saline upon use.

The main assessment item for the efficacies of the test was a change rate in bone mineral densities of lumbar vertebrae (second to fourth lumbar vertebrae).

The subsidiary assessment items for the efficacies of the test were a change rate in femoral bone mineral densities, a change rate in bone mineral densities of lumbar vertebrae (first to fourth lumbar vertebrae), an incidence rate of new vertebral bone fractures, an incidence rate of worsening vertebral bone fractures, incidence rates of (new and worsening) vertebral bone fractures, incidence rates of clinical bone fractures (clinical vertebral bone fractures and non-vertebral bone fractures), an incidence rate of vulnerable clinical bone fractures, an incidence rate of vulnerable non-vertebral bone fractures, and bone metabolism markers.

The safety assessment items for the test were adverse events, vital signs, clinical tests, and immunogenicity.

1.9. Measurement of Change Rate in Bone Mineral Densities:

The methods for measuring each of change rates in bone mineral densities of the bone mineral densities of lumbar vertebrae and the femoral bone mineral densities are shown in the following Table 1-1.

TABLE 1-1

|  | Bone mineral density of lumbar vertebrae | Femoral bone mineral density |
|---|---|---|
| Person taking measurement | A physician in charge of the investigational studies or a contributory physician of the investigational studies | |
| Timing of measurement | The beginning day of treatment, after 24 weeks, after 48 weeks, and at discontinuation | |
| Measurement sites | First to fourth lumbar vertebrae | Femoral proximal part is subjected to incycloduction at 20 degrees, and the measurement is only taken on a left side (the measurement is taken on a right side if the left side is immeasurable in connection with any prevalence or the like). The measurement site is taken from the same side throughout the investigational study period. |
| Measurement indices | Bone mineral content (BMC; g), bone area ($cm^2$), bone mineral density (BMD; $g/cm^2$) at each of the first to fourth lumbar vertebrae | Bone mineral content (BMC; g), bone area ($cm^2$), bone mineral density (BMD; $g/cm^2$) of femoral proximal total and femoral neck part |
| Measurement machine type | In the same test individuals, the identical sites are measured by the same machine type and the same scan mode throughout the investigational study period. | |

1.10. Assessment of Vertebral Bone Fractures:

The methods for assessing vertebral bone fractures are shown in the following Table 1-2.

TABLE 1-2

| X-ray photographer | A physician in charge of the investigational studies or a contributory physician of the investigational studies |
|---|---|
| Subjects to be X-ray photographed | Thoracic vertebrae and lumbar vertebrae |
| Timing of X-ray photographing | The beginning day of treatment, after 24 weeks, after 48 weeks, and at discontinuation |
| Assessment of vertebral bone fractures | An X-ray photograph at the beginning of treatment from fourth thoracic vertebra to fourth lumbar vertebra is compared with an X-ray photograph after the time course of a period. When normal centrum at the time point of the beginning of treatment is caused to be deformed after time course of a period and found to have a morphological fracture, it is defined as a new vertebral fracture. In addition, an X-ray photograph at the beginning of treatment from fourth thoracic vertebra to fourth lumbar vertebra is compared with an X-ray photograph after time course of a period. When deformed centrum already found at the time point of the beginning of treatment is again caused to be deformed after the time course of a period and found to have a morphological fracture, it is defined as a worsening vertebral fracture. The above judgment is carried out by the bone assessment committee in accordance with separately ordained judgment criteria in reference to a method of Genant et al, a method of Wu et al., and a method of Fukunaga et al. (Non-Patent Publications 11 to 13). |

1.11. Assessment of Clinical Bone Fractures (Clinical Vertebral Bone Fractures and Non-Vertebral Bone Fractures):

In a case where the test individuals appealed (for clinical symptoms) up to 48 weeks (at discontinuation) after the beginning of treatment and a physician in charge of the investigational studies or a contributory physician of the investigational studies confirmed the bone fractures by an X-ray photograph, MRI or the like, the test individuals were diagnosed as clinical bone fractures. In particular, in a case where test individuals appealed for acute pains at the lower back parts or back parts, an X-ray photograph was taken to confirm the presence or absence of the bone fractures.

The contents of assessment were the incidence date of bone fractures (the day a test individual developed the clinical symptoms), bone fracture sites (the centrum, femoral proximal parts, radius, upper arm bone, and others), the presence or absence of a large external force, the bases of judgment for the bone fractures (X-ray photographing, MRI, the information from other service departments or other medical institutions, and others), and the date of photographing X-ray or MRI.

1.12. Test of Bone Metabolism Markers:

The methods for testing bone metabolism markers are shown in the following Table 1-3.

TABLE 1-3

| Timing of Test | The beginning day of treatment, after 4 weeks, after 12 weeks, after 24 weeks, after 48 weeks, and at discontinuation (treatment period) | | |
|---|---|---|---|
| Test items | Blood marker tests | Bone formation | Osteocalcin, P1NP |
| | | Bone resorption | NTX, CTX |
| | | Others | Calcium, inorganic phosphorus, albumin, 25-hydroxyvitamin D fractions |
| | Urine marker tests | Bone formation | NTX |
| | | Others | Calcium, inorganic phosphorus, creatinine |

1.13. Studies on Adverse Events:

A physician in charge of the investigational studies or a contributory physician of the investigational studies studied on adverse events by voluntary reports from the test individuals, diagnosis by physician's inquiries on conditions of patients, and various tests, over a period from the day of the obtainment of the consent from each test individual to one week after the final day of administration.

The study items were the name of adverse events, the incidence date, the situations of administration of an investigational product, the day of disappearance, the outcomes of treatment, the classifications of degrees of seriousness, the reasons of seriousness, the levels, the cause-and-effect relationships between the investigational product and a standard concomitant drug, and when the adverse events were caused in the injected sites, the sites thereof, and the presence or absence of the discontinuation of the investigational studies.

1.14. Measurements of Vital Signs:

The methods for measuring vital signs are shown in the following Table 1-4.

TABLE 1-4

| Person taking measurement | A physician in charge of the investigational studies or a contributory physician of the investigational studies |
|---|---|
| Measurement items | Sitting systolic blood pressure, sitting diastolic blood pressure, pulse rate |
| Timing of measurement | The beginning day of treatment, after 4 weeks, after 12 weeks, after 24 weeks, and after 48 weeks |

TABLE 1-4-continued

| Time of measurement | Before administration of an investigational product, 10 minutes after the administration (allowable range ± 5 minutes), before coming home (to be in the course of one or more hours after the administration of an investigational product if at all possible) |
|---|---|

1.15. Clinical Test:

The method for a clinical test is shown in the following Table 1-5.

TABLE 1-5

| Collection of analytes | Collection of analytes (blood and urine) before administration of an investigational product on each test day | |
|---|---|---|
| Timing of test | The beginning day of treatment, after 4 weeks, after 12 weeks, after 24 weeks, after 48 weeks, and at discontinuation (treatment period) | |
| Test items | Blood general test | Red blood cell count |
| | | Hemoglobin |
| | | Hematocrit |
| | | White blood cell count |
| | | White blood cell count fraction |
| | | Platelet count |
| | Blood biochemical test | AST (GOT) |
| | | ALT (GPT) |
| | | Alkaline phosphatase |
| | | Total cholesterol |
| | | Urea nitrogen |
| | | Uric acid |
| | | Creatinine |
| | | CPK |
| | | Calcium |
| | | Inorganic phosphorus |
| | | Sodium |
| | | Potassium |
| | | Chlorine |
| | | Albumin |
| | Urine test | Occult blood (qualitative) |
| | | Protein (qualitative) |
| | | Sugar (qualitative) |
| | | Urobilinogen (qualitative) |
| | | Bilirubin (qualitative) |
| | | pH |

1.16. Assessment of Immunogenicity:

A physician in charge of the investigational studies or a contributory physician of the investigational studies collected analytes (blood) before the administration of an investigational product on the day of each test, and stored. An anti-drug antibody against the investigational product was measured after the collection of analytes. Only those analytes in which the anti-drug antibody was positive were measured for a neutralizing antibody.

2. Test Results:

2.1. Subjects to Be Analyzed for Efficacies:

Test individuals that expressed the consent of the treatment were 859 people, out of which 553 people registered for the investigational studies and received the treatment, in which 76 people discontinued the treatment and 477 people completed the treatment. Of those 553 people that received the treatment, the backgrounds (outline) of 551 people which were subjects to be analyzed for the efficacies are shown in the following Table 2-1. Table 2-1 shows that there are no large imbalances in backgrounds between Test Drug Group and Control Drug Group, so that the risks of bone fractures would be probably nearly of the same level.

TABLE 2-1

| Backgrounds (outline) of the subjects to be analyzed for efficacie | | Number of Test Drug Group (%) | Number of Control Drug Group (%) |
|---|---|---|---|
| Number of patients | | 275 | 276 |
| Gender | Male | 23 (8.4) | 25 (9.1) |
| | Female | 252 (91.6) | 251 (90.9) |
| Age | 65 ≤ Age < 70 | 69 (25.1) | 72 (26.1) |
| | 70 ≤ Age < 80 | 158 (57.5) | 144 (52.2) |
| | 80 ≤ Age | 48 (17.5) | 60 (21.7) |
| | Mean | 74.1 | 74.5 |
| Height (cm) | Height < 140 | 10 (3.6) | 12 (4.3) |
| | 140 ≤ Height < 150 | 112 (40.7) | 117 (42.4) |
| | 150 ≤ Height < 160 | 133 (48.4) | 125 (45.3) |
| | 160 ≤ Height | 20 (7.3) | 22 (8.0) |
| | Mean | 151.12 | 150.78 |
| Body weight (kg) | Body weight < 40 | 19 (6.9) | 15 (5.4) |
| | 40 ≤ Body weight < 50 | 125 (45.5) | 106 (38.4) |
| | 50 ≤ Body weight < 60 | 113 (41.1) | 120 (43.5) |
| | 60 ≤ Body weight | 18 (6.5) | 35 (12.7) |
| | Mean | 50.18 | 51.23 |
| Body mass index (BMI) (kg/m$^2$) | BMI < 18.5 | 30 (10.9) | 25 (9.1) |
| | 18.5 ≤ BMI < 25.0 | 208 (75.6) | 196 (71.0) |
| | 25.0 ≤ BMI | 37 (13.5) | 55 (19.9) |
| | Mean | 21.97 | 22.54 |
| Number of years passed after menopause | Number of years < 10 | 1 (0.4) | 0 (0.0) |
| | 10 ≤ Number of years < 20 | 66 (24.0) | 65 (23.6) |
| | 20 ≤ Number of years | 185 (67.3) | 186 (67.4) |
| | Mean | 24.1 | 25.0 |
| History of treatment of osteoporosis | Presence | 119 (43.3) | 127 (46.0) |
| | Absence | 156 (56.7) | 149 (54.0) |
| Number of prevalent vertebral bone fractures at registration | 1 | 156 (56.7) | 147 (53.3) |
| | 2 to 3 | 100 (36.4) | 115 (41.7) |
| | 4 to 5 | 19 (6.9) | 14 (5.1) |
| Bone mineral densities of lumbar vertebrae (L2-L4) on the basis of YAM (%) | Mean | 65.3 | 65.7 |

[2.2. Mean of Number of Administrations and Mean of Administration Period:

The mean of the number of administrations and the mean of the administration period in 553 individuals who received treatment are shown in Tables 2-2 and 2-3. Here, as to the mean of the number of administrations, a tested individuals that were previously administered with a test drug as an actual drug (MN-10-T AI) were administered with a control drug placebo (MN-10-T Placebo), and test individuals that were previously administered with a control drug as an actual drug (MN-10-T) were administered with a test drug placebo (MN-10-T AI Placebo) (FIG. 29). Therefore, the mean of the number of administrations of the four agents, a test drug actual drug, a control drug placebo, a test drug placebo, and a control drug actual drug, is calculated.

TABLE 2-2

| Mean of number of administrations (times) | | |
|---|---|---|
| | | Mean of number of administrations |
| Test Drug Group | Test drug actual drug | 81.9 |
| | Control drug placebo | 41.1 |
| Control Drug Group | Test drug placebo | 80.1 |
| | Control drug actual drug | 40.1 |

TABLE 2-3

| Mean of administration period (weeks) | |
|---|---|
| | Mean of administration period |
| Test Drug Group | 43.9 |
| Control Drug Group | 42.8 |

It was considered that there were no significant differences in the mean of the number of administrations when the test drug actual drug of Test Drug Group was compared with the test drug placebo of Control Drug Group, and the control drug placebo of Test Drug Group was compared with the control drug actual drug of Control Drug Group.

It was considered that there were no differences in the mean of the administration period between Test Drug Group and Control Drug Group. Here, the reasons why some did not reach 48 weeks are in that examples that were discontinued in the course were included.

2.3. Time Transition of Mean Value of Change Rate in Bone Mineral Densities of Each of Lumbar Vertebrae, Femoral Neck Part, and Femoral Proximal Total:

The time transitions of the mean value of a change rate in bone mineral densities of each of lumbar vertebrae (second to fourth lumbar vertebrae), lumbar vertebrae (first to fourth lumbar vertebrae), a femoral neck part, and a femoral proximal total in the subjects to be analyzed for the efficacies are shown in the following Tables 2-4 to 2-7. The numerical values in the tables show a mean value of a change rate (%) from the beginning.

Figure 4:
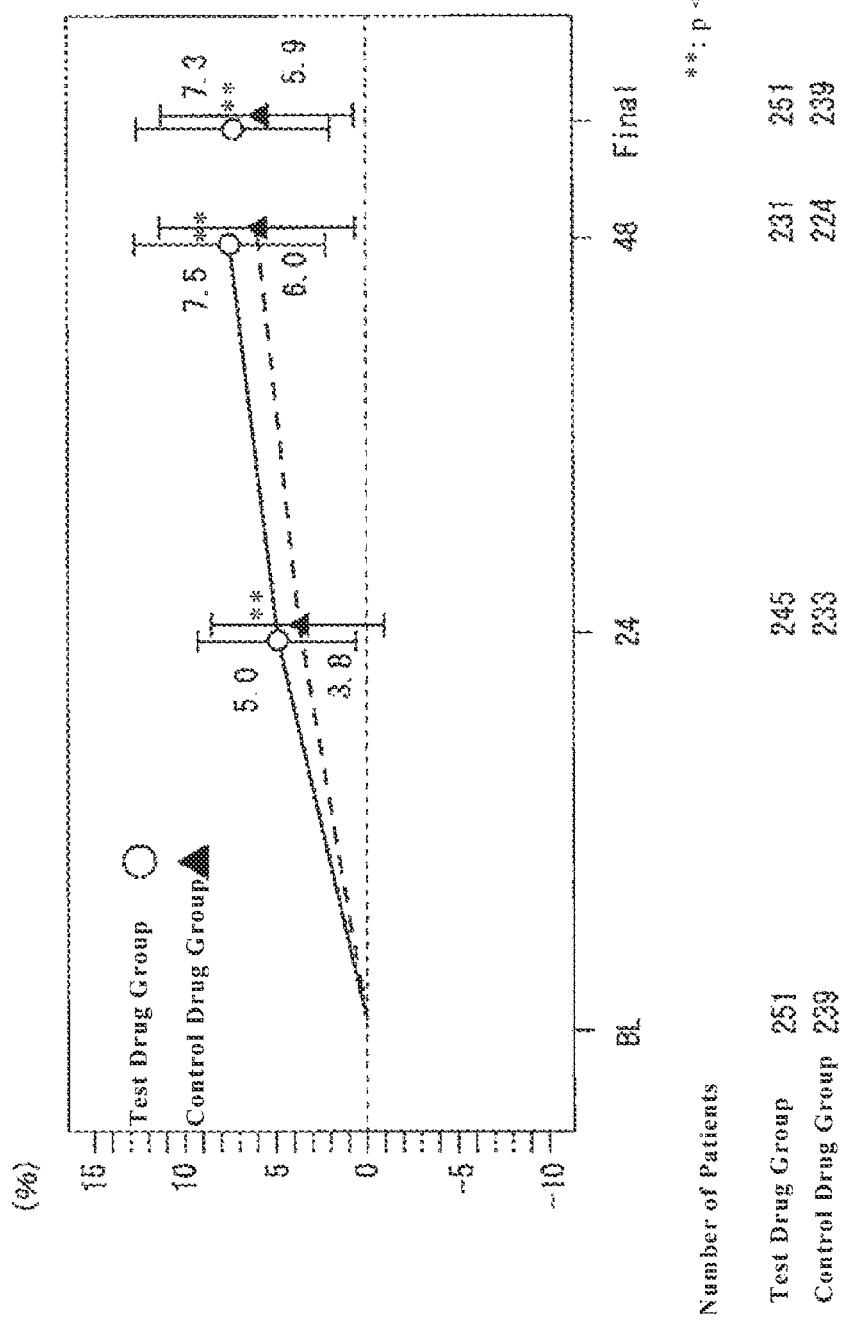
FIGS. 4 to 28 are graphs relating to the test results of Working Examples, and the details of each drawing are explained as follows.

In addition, the time transitions of the mean value of a change rate in bone mineral densities of lumbar vertebrae (second to fourth lumbar vertebrae) in the subjects to be analyzed for the efficacies are shown in FIG. 4.

TABLE 2-4

Time transitions of the mean value of change rate (%) in bone mineral densities of lumbar vertebrae (second to fourth lumbar vertebrae)

|  | After 24 weeks | After 48 weeks | at Final |
|---|---|---|---|
| Test Drug Group | 5.0** | 7.5** | 7.3** |
| Control Drug Group | 3.8 | 6.0 | 5.9 |

**p < 0.01 (Statistical analysis results in accordance with a t-test student)

TABLE 2-5

Time transitions of the mean value of change rate (%) in bone mineral densities of lumbar vertebrae (first to fourth lumbar vertebrae)

|  | After 24 weeks | After 48 weeks | at Final |
|---|---|---|---|
| Test Drug Group | 4.8** | 7.2** | 7.1** |
| Control Drug Group | 3.5 | 5.5 | 5.4 |

**p < 0.01

TABLE 2-6

Time transitions of the mean value of change rate (%) in bone mineral densities of femoral neck part

|  | After 24 weeks | After 48 weeks | at Final |
|---|---|---|---|
| Test Drug Group | 1.6 | 2.1 | 2.0 |
| Control Drug Group | 1.0 | 1.4 | 1.4 |

TABLE 2-7

Time transitions of the mean value of change rate (%) in bone mineral densities of femoral proximal total

|  | After 24 weeks | After 48 weeks | at Final |
|---|---|---|---|
| Test Drug Group | 1.3 | 1.8 | 1.8 |
| Control Drug Group | 1.0 | 1.3 | 1.3 |

The treatment with a test drug showed high increase rates in all of the bone mineral density of lumbar vertebrae, the bone mineral density of the femoral neck part, and the bone mineral density of femoral proximal total, as compared to those treatment with a control drug. Especially, it was significantly high in the bone mineral densities of lumbar vertebrae.

When the treatment with a test drug was compared with the treatment with a control drug, it is considered that the dosage of teriparatide per week is substantially of the same level. On the other hand, it has been reported that the bone mineral density and the bone strength increase in accordance with the dosage of teriparatide per week (Non-Patent Publication 14). Therefore, it was considered that the results which can be thought to be significant in the comparisons between the treatment with a test drug and the treatment with a control drug can be clearly distinguished from the conventional medical techniques.

The subjects to be analyzed for the efficacies were divided into subgroups in which the bone mineral densities of lumbar vertebrae (second to fourth lumbar vertebrae) at the beginning or the number of prevalent vertebral bone fractures was used as an index. The results of analyzing the mean value of a change rate in the bone mineral densities of lumbar vertebrae (second to fourth lumbar vertebrae) at final are shown in the following Tables 2-8 and 2-9. The numerical values in the tables show a mean value of a change rate (%) from the beginning.

TABLE 2-8

Mean value of change rate in bone mineral densities of lumbar vertebrae (second to fourth lumbar vertebrae) at final classified by bone mineral densities of lumbar vertebrae (second to fourth lumbar vertebrae) from the beginning

| Bone mineral densities of lumbar vertebrae | Test Drug Group | | Control Drug Group | |
|---|---|---|---|---|
| (second to fourth lumbar vertebrae) (%, YAM ratio) | No. of cases | Mean value of change rate (%) | No. of cases | Mean value of change rate (%) |
| Less than 60 | 74 | 9.4 | 61 | 8.2 |
| 60 Or more and less than 70 | 93 | 7.0 | 89 | 5.4 |
| 70 Or more and less than 80 | 79 | 5.9 | 87 | 5.0 |

TABLE 2-9

Mean value of change rate in bone mineral densities of lumbar vertebrae (second to fourth lumbar vertebrae) at final classified by the number of prevalent vertebral bone fractures

| | Test Drug Group | | Control Drug Group | |
|---|---|---|---|---|
| No. of prevalent fractures | No. of cases | Mean value of change rate (%) | No. of cases | Mean value of change rate (%) |
| 1 | 138 | 7.8 | 128 | 5.9 |
| 2 to 3 | 95 | 6.9 | 101 | 6.2 |
| 4 to 5 | 18 | 5.4 | 10 | 4.6 |

It has been reported that the risks of the vertebral bone fractures would be 2.3 times by a decrease in the bone mineral densities of lumbar vertebrae by 1 SD (Non-Patent Publication 9).

The increase in the bone mineral densities of lumbar vertebrae by the administration was analyzed using the bone mineral densities of lumbar vertebrae at the beginning or the number of prevalent vertebral bone fractures as an index. As a result, the increase in the bone mineral densities of lumbar vertebrae by the administration showed the tendency of being high along with the decrease in the bone mineral densities of lumbar vertebrae at the beginning, and conversely the increase in the bone mineral densities of lumbar vertebrae by the administration showed the tendency of being low along with the increase in the number of prevalent vertebral bone fractures.

The subjects to be analyzed for the efficacies were divided into subgroups in which the value of serum osteocalcin at the beginning was used as an index. The results of analyzing the time transitions of the mean value of a change rate in the bone mineral densities of lumbar vertebrae (second to fourth lumbar vertebrae) and in the femoral neck part are shown in the following Tables 2-10 and 2-11. The numerical values in the tables show a mean value of a change rate (%) from the beginning.

TABLE 2-10

Time transitions of the mean value of change rate (%) in bone mineral densities of lumbar vertebrae (second to fourth lumbar vertebrae)

| | Serum osteocalcin (OC) concentration (ng/mL) at beginning | After 24 weeks (no. of cases) | After 48 weeks (no. of cases) | at Final (no. of cases) |
|---|---|---|---|---|
| Test Drug Group | OC conc. < 15.2 | 3.9 (84) | 5.1 (82) | 5.3 (85) |
| | 15.2 ≤ OC conc. < 21.8 | 4.5 (79) | 6.9 (74) | 6.7 (82) |
| | 21.8 ≤ OC conc. | 6.5 (82) | 10.6 (75) | 9.9 (84) |
| Control Drug Group | OC conc. < 14.8 | 1.7 (76) | 3.1 (74) | 3.1 (78) |
| | 14.8 ≤ OC conc. < 21.9 | 3.6 (78) | 6.1 (75) | 6.0 (82) |
| | 21.9 ≤ OC conc. | 5.9 (79) | 8.8 (75) | 8.7 (79) |

TABLE 2-11

Time transitions of the mean value of change rate (%) in bone mineral densities of femoral neck part

| | Serum osteocalcin (OC) concentration (ng/mL) at beginning | After 24 weeks (no. of cases) | After 48 weeks (no. of cases) | at Final (no. of cases) |
|---|---|---|---|---|
| Test Drug Group | OC conc. < 15.2 | 1.0 (85) | 1.4 (83) | 1.4 (86) |
| | 15.2 ≤ OC conc. < 21.8 | 1.5 (84) | 1.9 (80) | 1.8 (87) |
| | 21.8 ≤ OC conc. | 2.3 (84) | 3.1 (77) | 2.9 (85) |
| Control Drug Group | OC conc. < 14.8 | 0.3 (79) | 0.2 (76) | 0.1 (81) |
| | 14.8 ≤ OC conc. < 21.9 | 0.9 (79) | 1.2 (77) | 1.2 (84) |
| | 21.9 ≤ OC conc. | 2.0 (84) | 2.9 (78) | 2.8 (84) |

TABLE 2-12

Time transitions of mean value of change rate (%) in bone mineral densities of lumbar vertebrae (second to fourth lumbar vertebrae)

| | Serum P1NP concentration (μg/L) at beginning | After 24 weeks (no. of cases) | After 48 weeks (no. of cases) | at Final (no. of cases) |
|---|---|---|---|---|
| Test Drug Group | P1NP conc. < 38.0 | 3.4 (79) | 4.9 (76) | 4.9 (82) |
| | 38.0 ≤ P1NP conc. < 58.5 | 4.8 (86) | 7.4 (83) | 7.2 (87) |
| | 58.5 ≤ P1NP conc. | 6.7 (80) | 10.2 (72) | 9.8 (82) |
| Control Drug Group | P1NP conc. < 37.4 | 2.1 (78) | 3.4 (75) | 3.4 (80) |
| | 37.4 ≤ P1NP conc. < 57.3 | 3.2 (78) | 5.4 (76) | 5.5 (80) |
| | 57.3 ≤ P1NP conc. | 6.0 (77) | 9.3 (73) | 9.0 (79) |

TABLE 2-13

Time transitions of mean value of change rate (%) in bone mineral densities of femoral neck part

| | Serum P1NP concentration (μg/L) at beginning | After 24 weeks (no. of cases) | After 48 weeks (no. of cases) | at Final (no. of cases) |
|---|---|---|---|---|
| Test Drug Group | P1NP conc. < 38.0 | 0.5 (81) | 1.4 (78) | 1.4 (84) |
| | 38.0 ≤ P1NP conc. < 58.5 | 1.7 (86) | 1.6 (84) | 1.6 (87) |
| | 58.5 ≤ P1NP conc. | 2.5 (86) | 3.4 (78) | 3.1 (87) |
| Control Drug Group | P1NP conc. < 37.4 | 0.9 (76) | 0.9 (73) | 0.8 (78) |
| | 37.4 ≤ P1NP conc. < 57.3 | 0.2 (82) | 1.1 (79) | 1.0 (84) |
| | 57.3 ≤ P1NP conc. | 2.0 (84) | 2.4 (79) | 2.3 (87) |

The subjects to be analyzed for the efficacies were divided into subgroups in which the value of blood P1NP at the beginning was used as an index. The results of analyzing the time transitions of the mean value of a change rate in the bone mineral densities of lumbar vertebrae (second to fourth lumbar vertebrae) and the femoral neck part are shown in the following Tables 2-12 and 2-13. The numerical values in the tables show a mean value of a change rate (%) from the beginning.

On the bases of the data of the above four tables, the calculated results that the mean value of a change rate in bone mineral densities at final (Test Drug Group) of the subgroup in which the OC or P1NP concentration at the beginning was the lowest was divided by the mean value of a change rate in bone mineral densities at final (Control Drug Group) of the subgroup in which the OC or P1NP concentration at the beginning was the lowest are shown the following Table 2-14.

TABLE 2-14

| Bone formation marker | Subgroup in which bone formation marker at beginning was lowest (Test Drug Group) (A Group) | Subgroup in which bone formation marker at beginning was lowest (Control Drug Group) (B Group) | Sites of Bone | Value calculated by dividing the mean value of change rate (%) in bone mineral densities shown at final of A Group by the mean value of change rate (%) in bone mineral densities shown at final of B Group |
|---|---|---|---|---|
| OC | OC Conc. < 15.2 (ng/mL) | OC Conc. < 14.8 (ng/mL) | Bone mineral densities of lumbar vertebrae (second to fourth lumbar vertebrae) | 1.71 |
| | | | Femoral neck part | 14.0 |
| P1NP | P1NP Conc. < 38.0 (μg/L) | P1NP Conc. < 37.4 (μg/L) | Bone mineral densities of lumbar vertebrae (second to fourth lumbar vertebrae) | 1.44 |
| | | | Femoral neck part | 1.75 |

The treatment with a test drug was considered to be particularly excellent from the viewpoint of the effects of increasing the bone mineral density of femoral neck part when the patients having relatively low blood OC concentrations (for example, less than 15.2 (ng/mL)) were used as subjects.

2.4. Incidence Rate of Vertebral Bone Fractures:

The time transitions or the like of the incidence rate of new vertebral bone fractures and the incidence rate of worsening vertebral bone fractures in accordance with a Kaplan-Meier method in the subjects to be analyzed for the efficacies are shown in Tables 2-15 and 2-16.

TABLE 2-15

Time transitions or the like of incidence rate of new vertebral bone fractures

| | No. of assessed cases | Numbers discontinued during the course | No. of cases of bone fracture incidence | Accumulated incidence rate of bone fractures | |
|---|---|---|---|---|---|
| | | | | Week 24 (%) | Week 48 (%) |
| Test Drug Group | 259 | 17 | 3 | 1.2 | 1.2 |
| Control Drug Group | 247 | 16 | 4 | 1.2 | 1.7 |

TABLE 2-16

Time transitions or the like of incidence rate of worsening vertebral bone fractures

| | No. of assessed cases | Numbers discontinued during the course | No. of cases of bone fracture incidence | Accumulated incidence rate of bone fractures | |
|---|---|---|---|---|---|
| | | | | Week 24 (%) | Week 48 (%) |
| Test Drug Group | 259 | 18 | 1 | 0.0 | 0.4 |
| Control Drug Group | 247 | 16 | 1 | 0.4 | 0.4 |

2.5. Incidence Rate of Clinical Vertebral Bone Fractures:

The time transitions or the like of the incidence rate of clinical vertebral bone fractures in accordance with a Kaplan-Meier method in the subjects to be analyzed for the efficacies are shown in the following Table 2-17.

TABLE 2-17

Time transitions or the like of incidence rate of clinical vertebral bone fractures

| | No. of assessed cases | Numbers discontinued during the course | No. of cases of bone fractures incidence | Accumulated incidence rate of bone fractures | |
|---|---|---|---|---|---|
| | | | | Week 24 (%) | Week 48 (%) |
| Test Drug Group | 275 | 42 | 3 | 0.7 | 1.2 |
| Control Drug Group | 276 | 52 | 4 | 1.1 | 1.6 |

According to the above data for the incidence rate of vertebral bone fractures, it can be considered that the treatment with a test drug is excellent also from the viewpoint of inhibiting the vertebral bone fractures in general, as compared to the treatment with a control drug.

2.6. Bone Resorption Marker:

The time transitions of the bone resorption markers in the subjects to be analyzed for the efficacies are shown in the following Tables 2-18 to 2-20.

TABLE 2-18

Time transitions of serum CTX

| | | No. of assessed cases | Median value of change rate (%) from the baseline |
|---|---|---|---|
| Test Drug Group | After 4 weeks | 266 | −22.2 |
| | After 12 weeks | 265 | −17.1 |
| | After 24 weeks | 256 | −21.4 |
| | After 48 weeks | 243 | −29.4 |
| Control Drug Group | After 4 weeks | 266 | −15.3 |
| | After 12 weeks | 259 | −13.0 |
| | After 24 weeks | 248 | −23.7 |
| | After 48 weeks | 237 | −19.4 |

TABLE 2-19

Time transitions of serum NTX

| | | No. of assessed cases | Median value of change rate (%) from the baseline |
|---|---|---|---|
| Test Drug Group | After 4 weeks | 266 | −5.9 |
| | After 12 weeks | 265 | −5.5 |
| | After 24 weeks | 256 | −8.8 |
| | After 48 weeks | 243 | −7.1 |
| Control Drug Group | After 4 weeks | 266 | −4.1 |
| | After 12 weeks | 259 | −3.8 |
| | After 24 weeks | 248 | −9.0 |
| | After 48 weeks | 237 | −8.4 |

TABLE 2-20

Time transitions of urine NTX

| | | No. of assessed cases | Median value of change rate (%) from the baseline |
|---|---|---|---|
| Test Drug Group | After 4 weeks | 266 | −16.0 |
| | After 12 weeks | 265 | −17.9 |
| | After 24 weeks | 256 | −30.8 |
| | After 48 weeks | 243 | −18.6 |
| Control Drug Group | After 4 weeks | 266 | −12.0 |
| | After 12 weeks | 259 | −11.4 |
| | After 24 weeks | 248 | −23.2 |
| | After 48 weeks | 237 | −9.1 |

Figure 5:
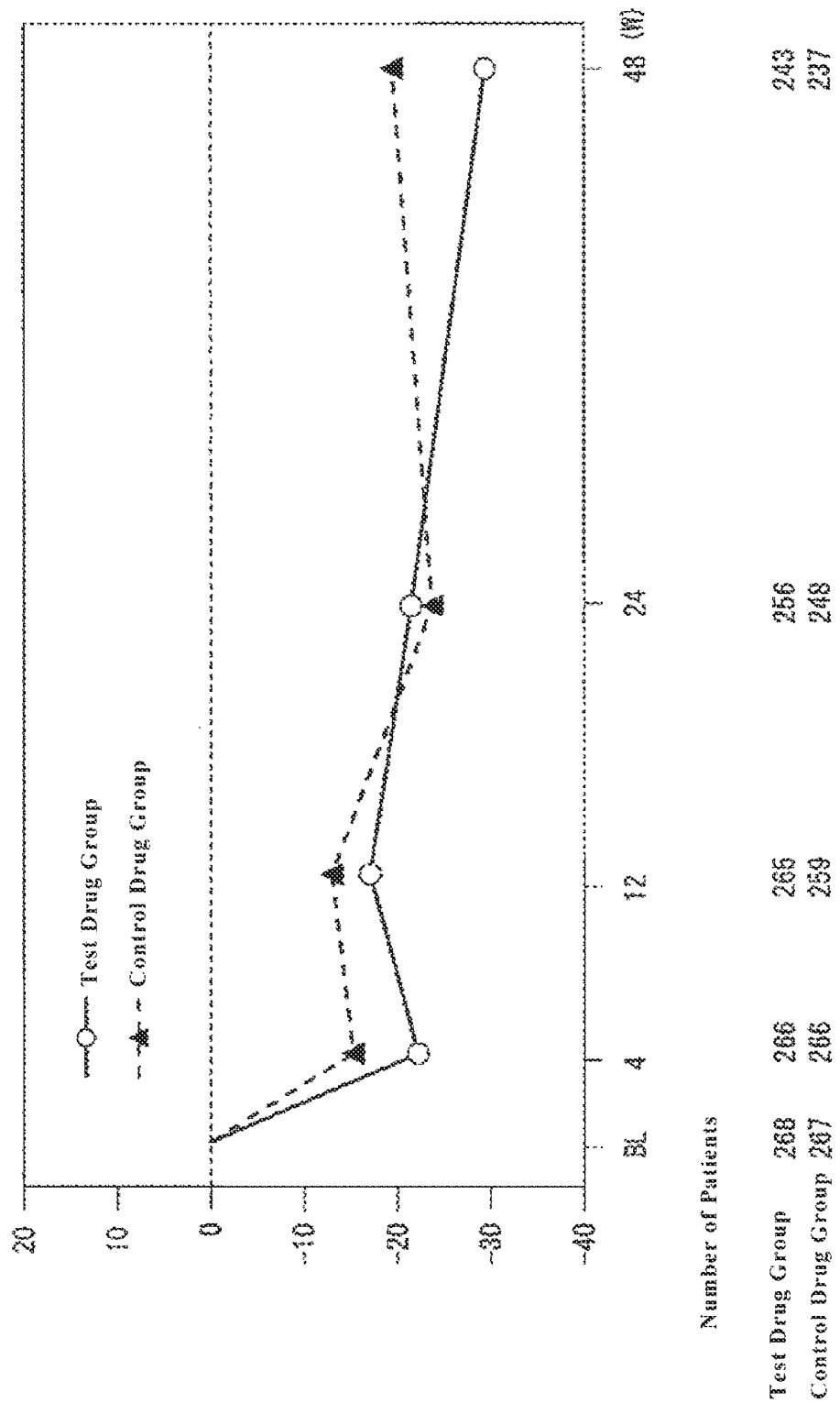
Figure 6:
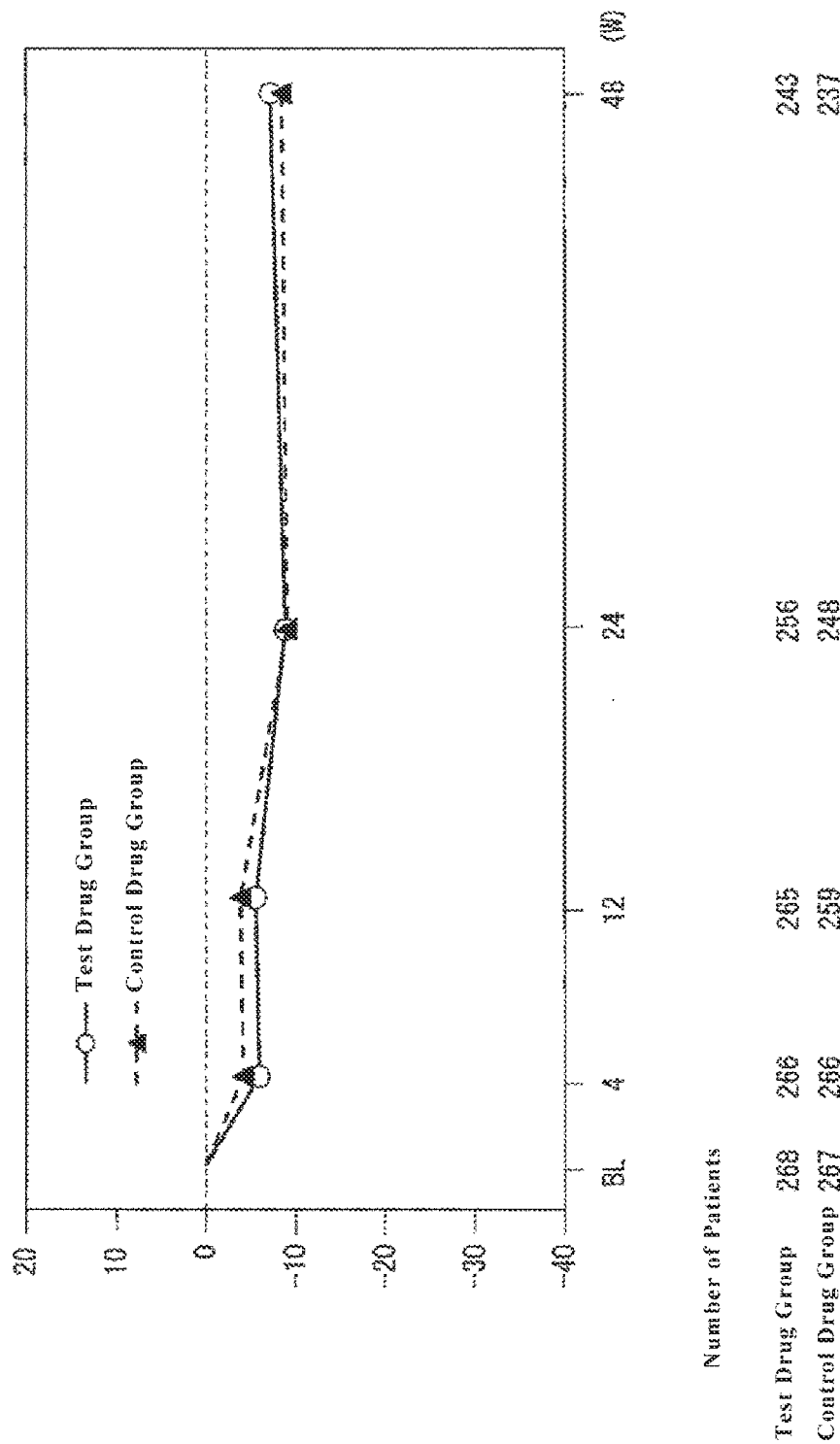
Figure 7:
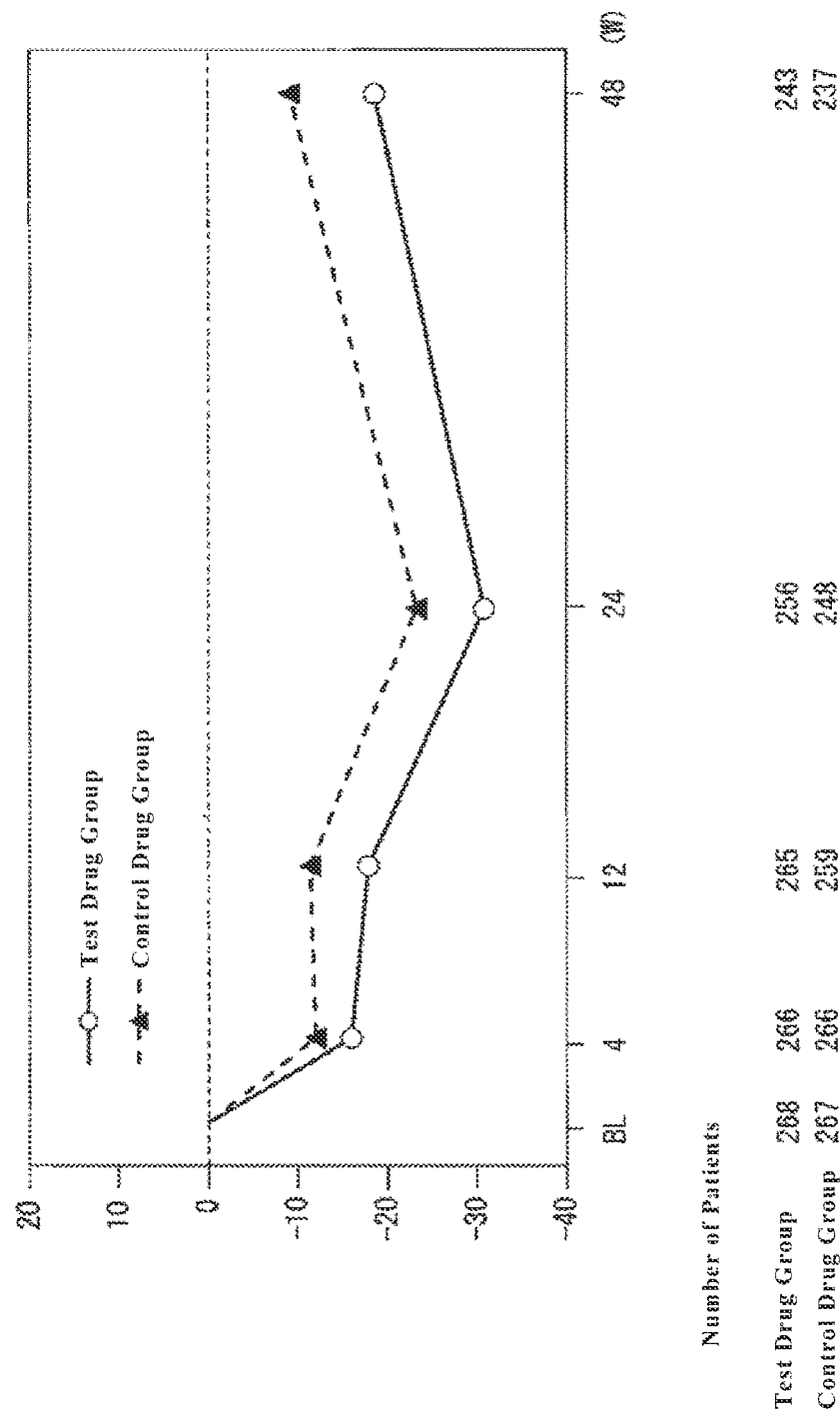

The time transitions of the bone resorption markers accompanying the treatment with a test drug were of the same level or slightly inhibited, as compared to the time transitions of the bone resorption markers accompanying the treatment with a control drug (FIGS. 5 to 7).

Non-Patent Publication 17 has reported that the daily administration of a test drug enhances the bone resorption markers or the like. Further, in Non-Patent Publication 27 corroded surfaces indicating bone resorption are found in void surfaces in cortical bones caused by the daily administration of a test drug (see, FIG. 7 c etc.), whereby suggesting that there is a deep relationship between the porosity of the cortical bones and the increase in bone resorption. In light of the contents or the like of these publications, it is assumed that the time transitions of the bone resorption markers in the treatment of twice a week in this case suggests that the treatment of administration of twice a week is a treatment that does not show an increase in bone turnover so as to increase a void ratio of cortical bone as compared to that of the treatment of administration of once a week.

2.7. Bone Formation Markers:

The time transitions of the bone formation markers in the subjects to be analyzed for the efficacies are shown in the following Tables 2-21 and 2-22.

TABLE 2-21

Time transitions of serum OC

|  |  | No. of assessed cases | Median value of change rate (%) from the baseline |
|---|---|---|---|
| Test Drug Group | After 4 weeks | 266 | 45.7** |
|  | After 12 weeks | 265 | 39.9** |
|  | After 24 weeks | 256 | 21.8* |
|  | After 48 weeks | 243 | 6.8 |
| Control Drug Group | After 4 weeks | 266 | 29.5 |
|  | After 12 weeks | 259 | 23.0 |
|  | After 24 weeks | 248 | 10.7 |
|  | After 48 weeks | 237 | 4.2 |

*Wilcoxon rank sum test $p < 0.05$
**Wilcoxon rank sum test $p < 0.01$

TABLE 2-22

Time transitions of serum P1NP

|  |  | No. of assessed cases | Median value of change rate (%) from the baseline |
|---|---|---|---|
| Test Drug Group | After 4 weeks | 266 | 28.3** |
|  | After 12 weeks | 265 | 12.6* |
|  | After 24 weeks | 256 | 1.3 |
|  | After 48 weeks | 243 | -1.4 |
| Control Drug Group | After 4 weeks | 266 | 17.2 |
|  | After 12 weeks | 259 | 5.2 |
|  | After 24 weeks | 248 | 0.2 |
|  | After 48 weeks | 237 | 1.0 |

*Wilcoxon rank sum test $p < 0.05$
**Wilcoxon rank sum test $p < 0.01$

Figure 8:
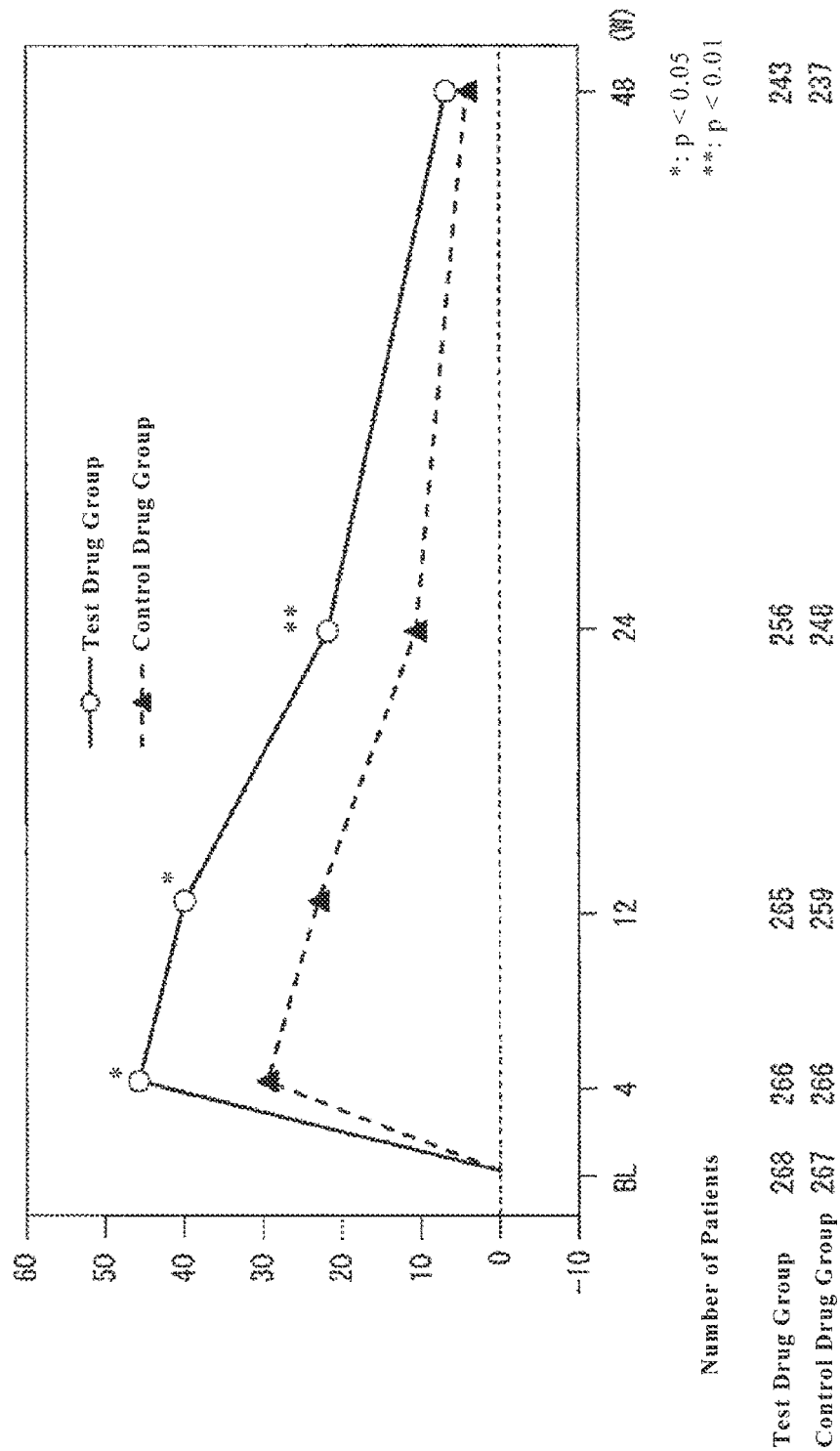
Figure 9:
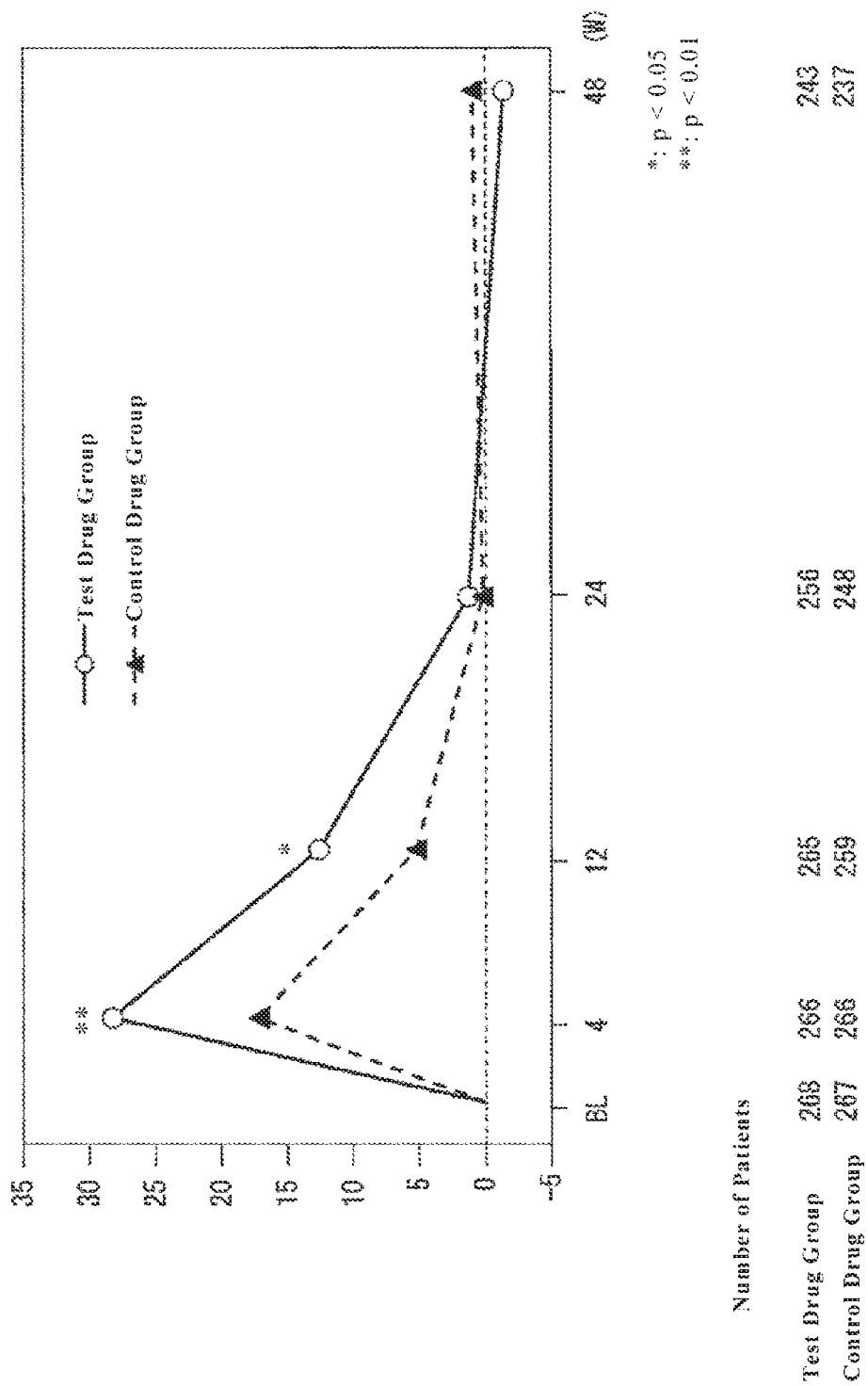
Figure 10:
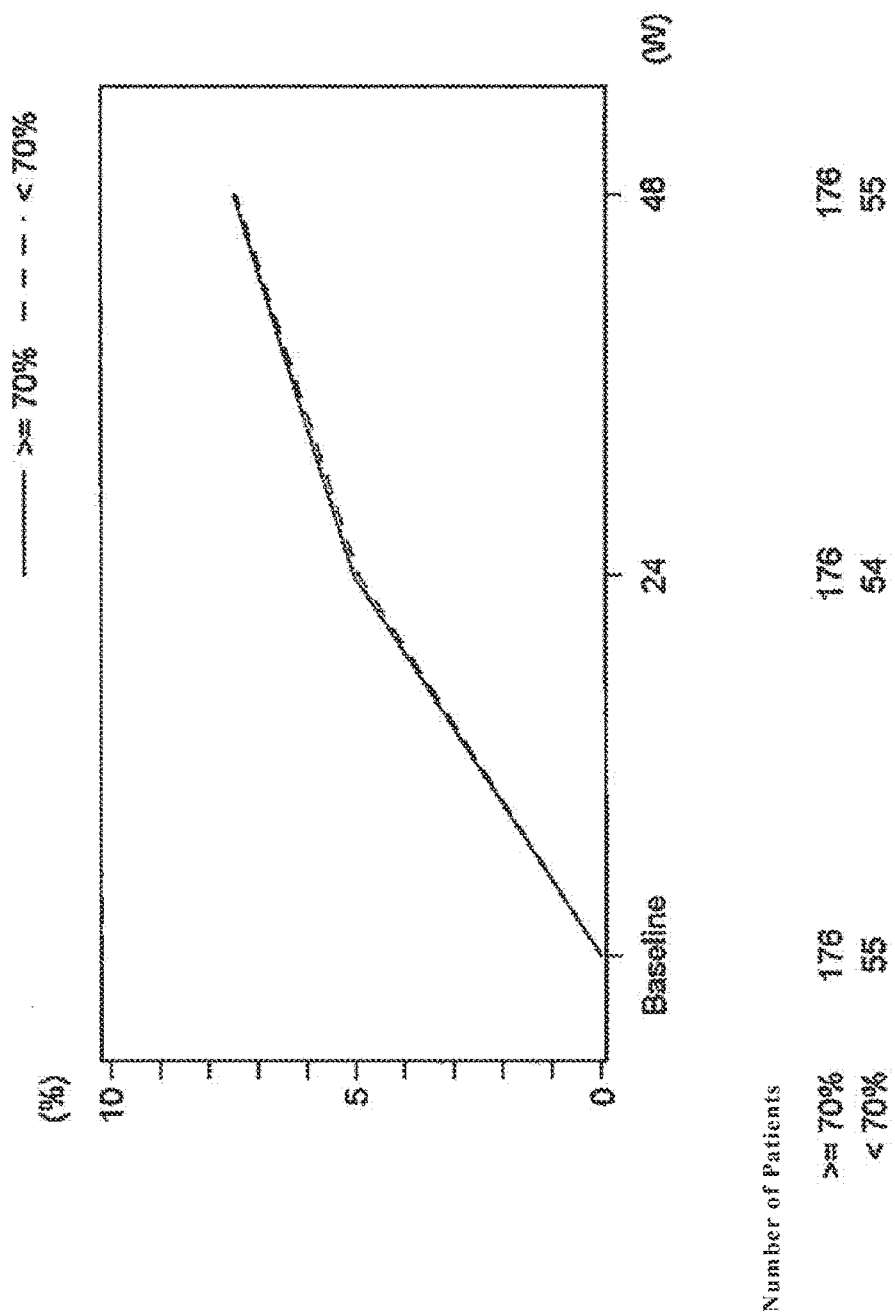
Figure 11:
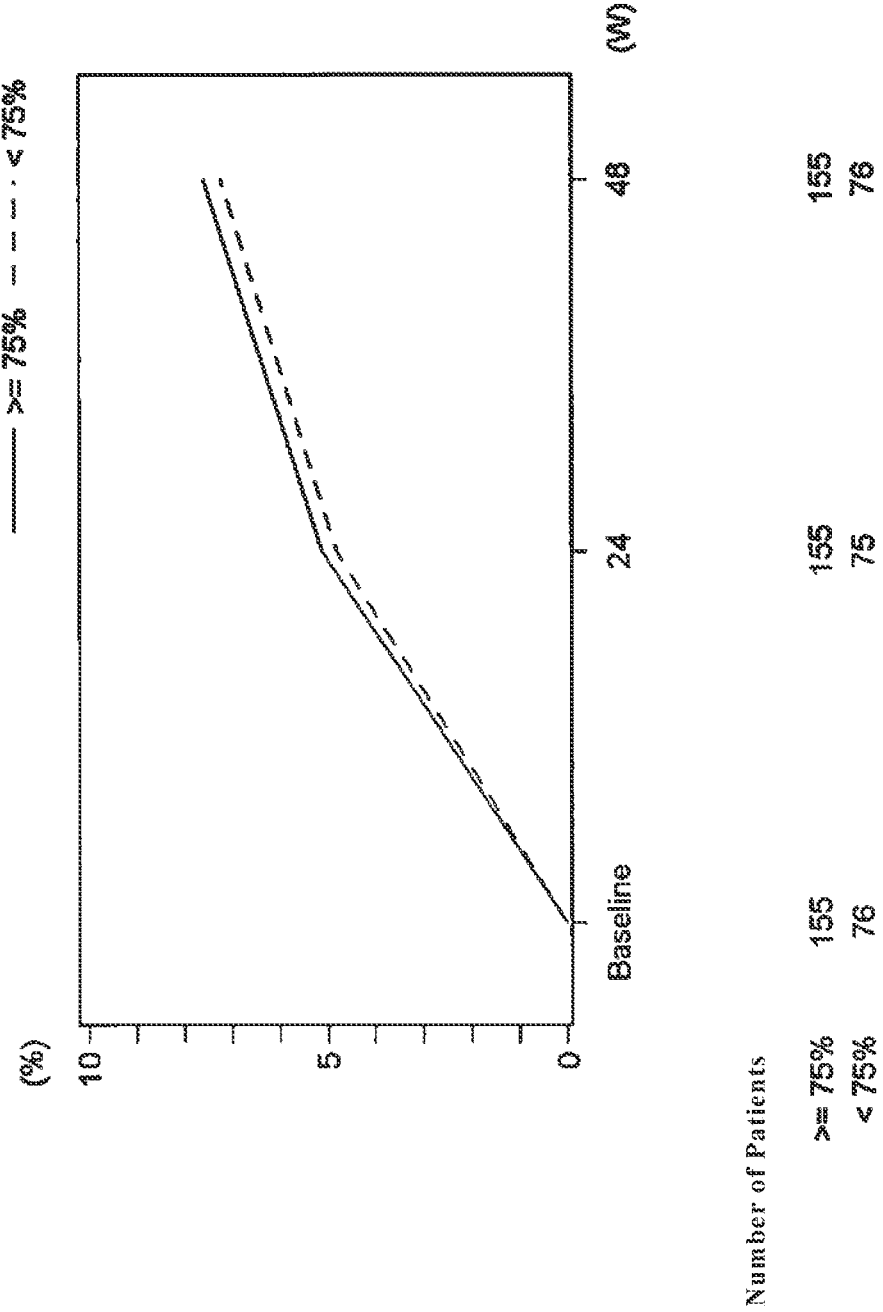
Figure 12:
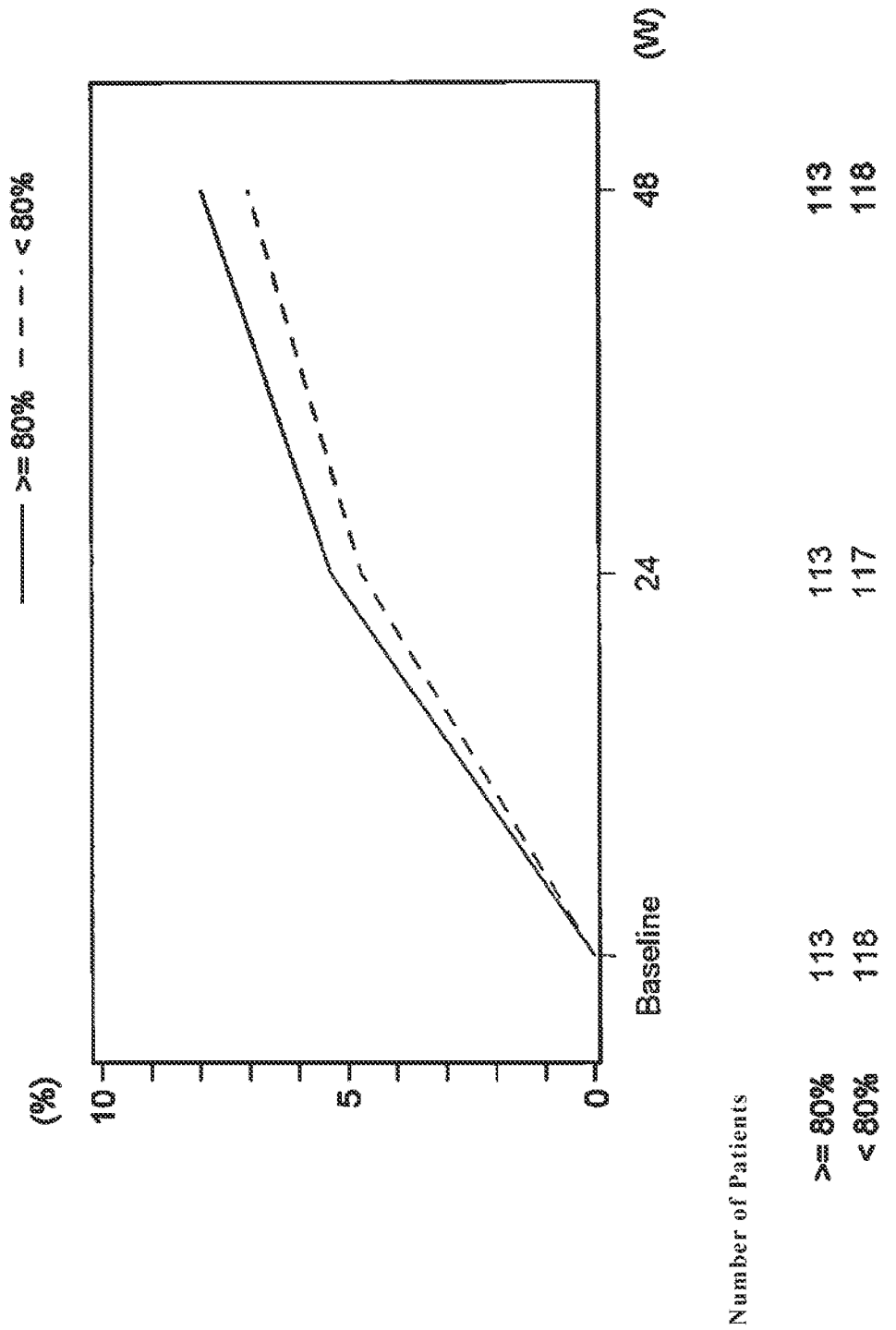
Figure 13:
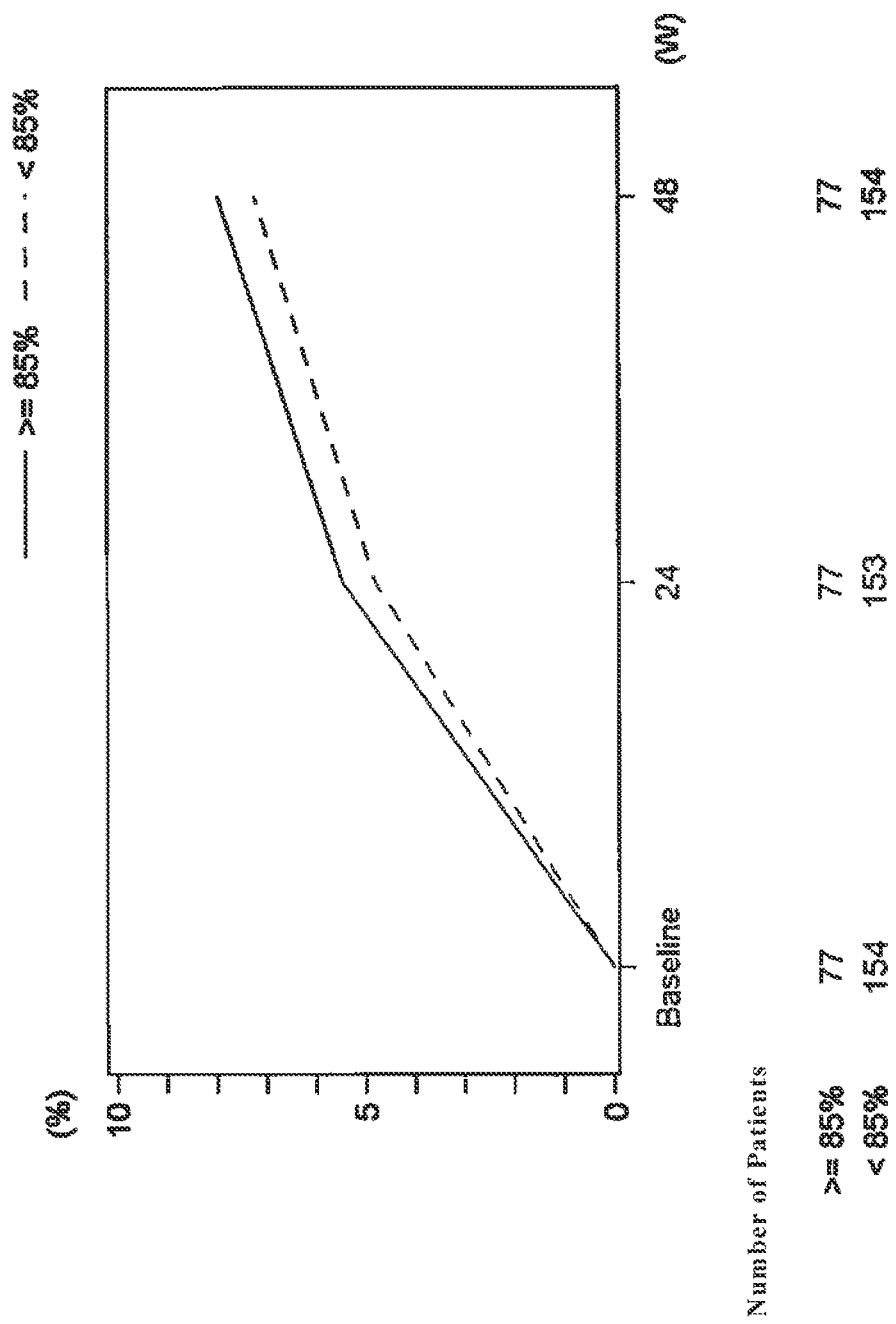
Figure 14:
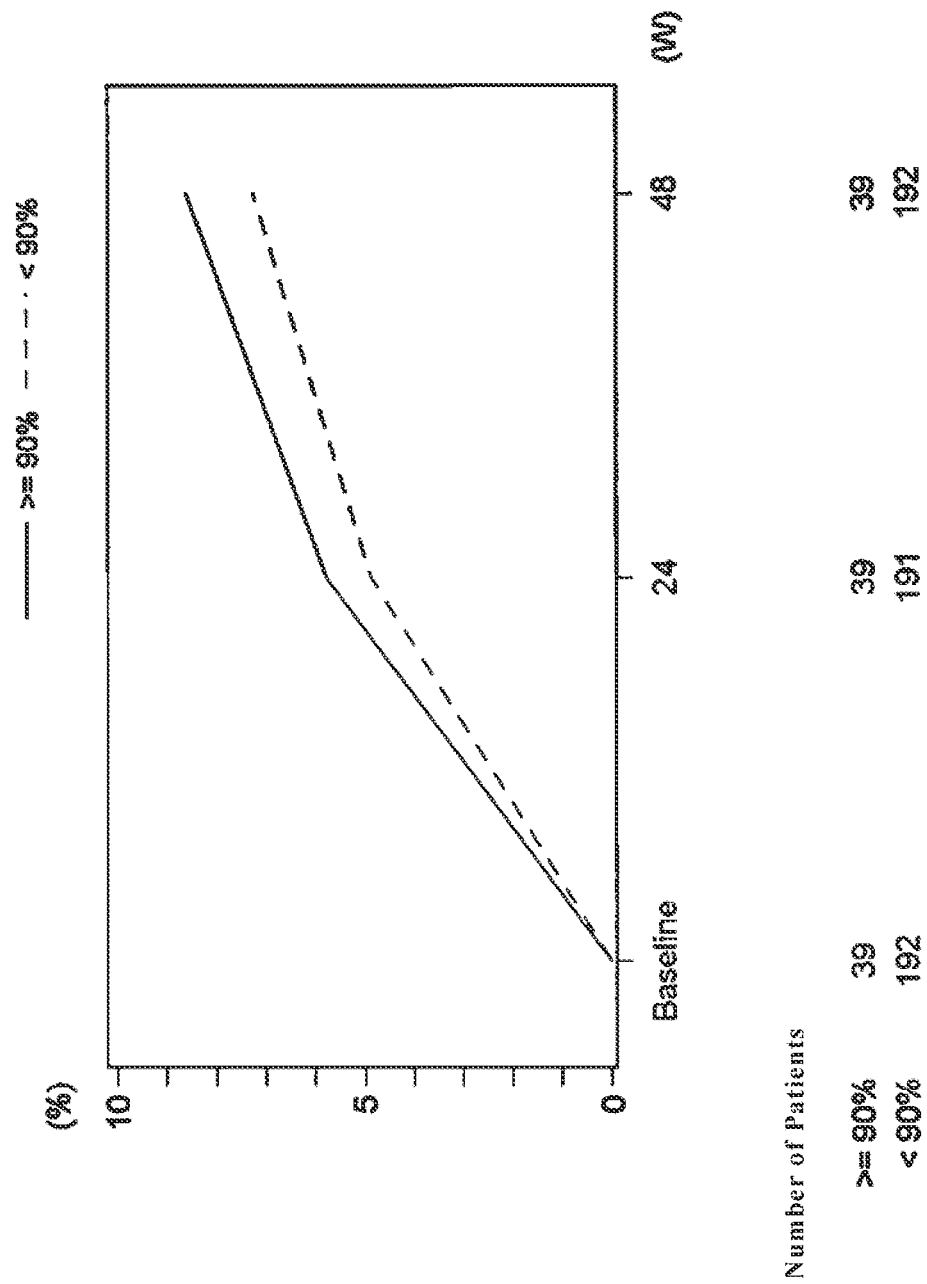
Figure 15:
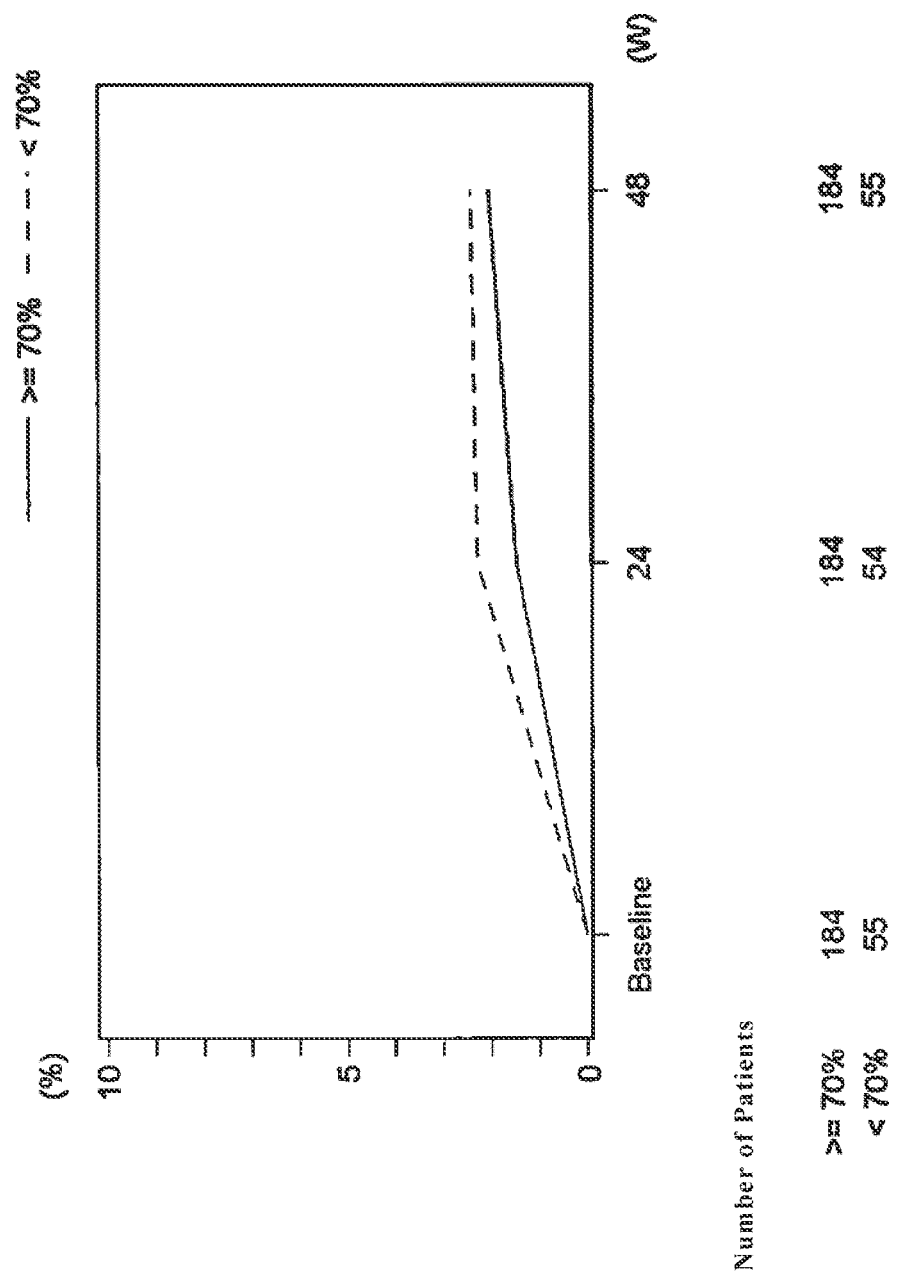
Figure 16:
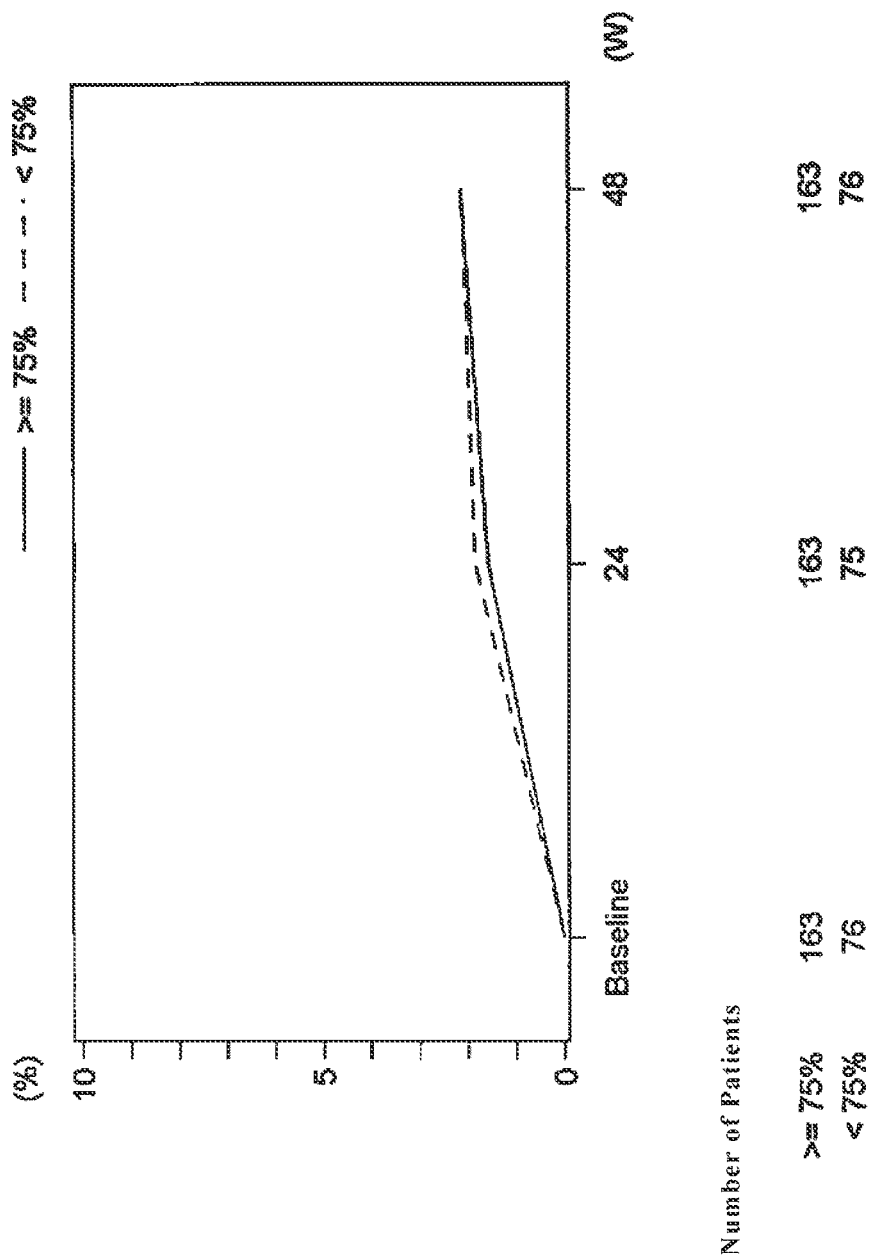
Figure 17:
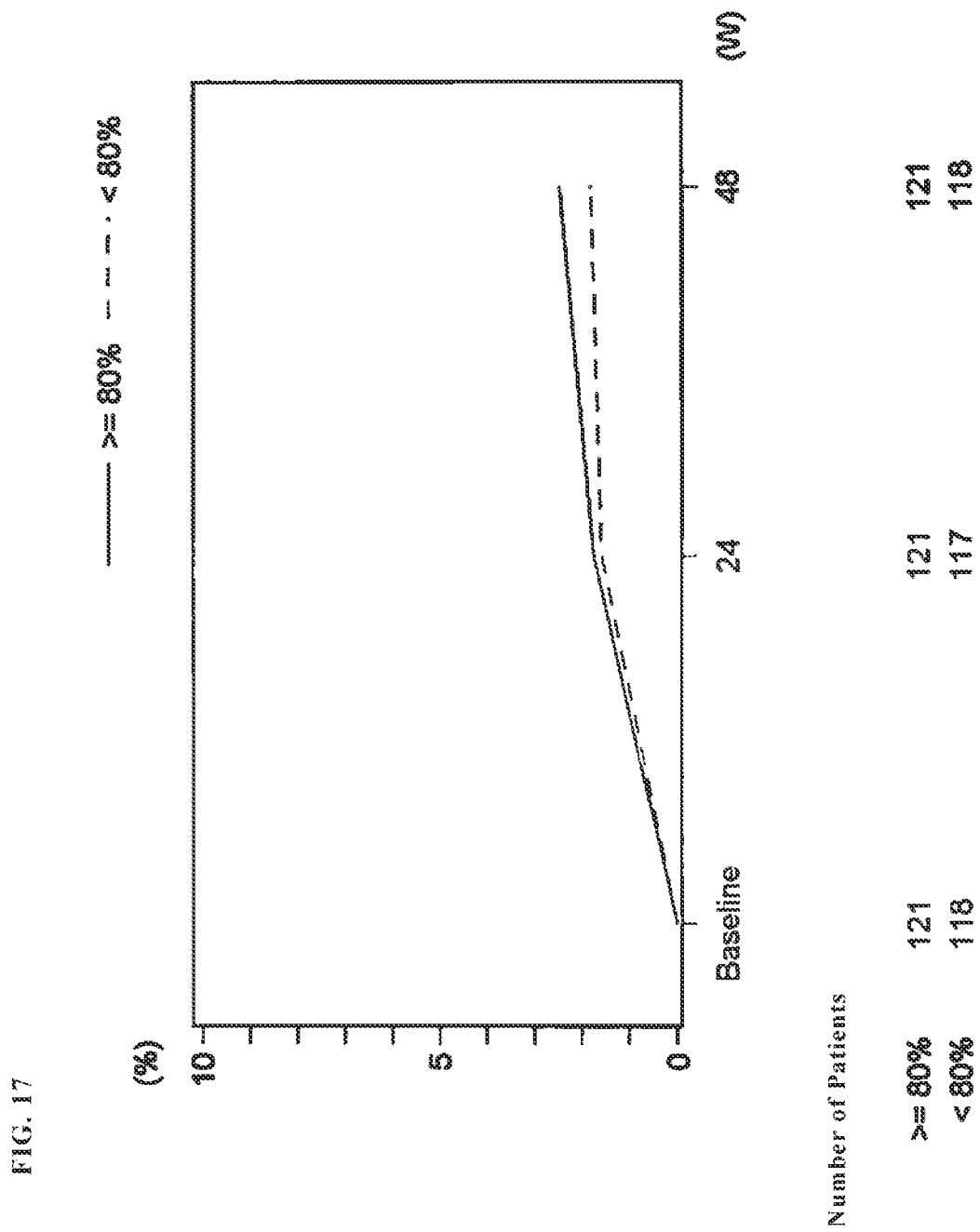
Figure 18:
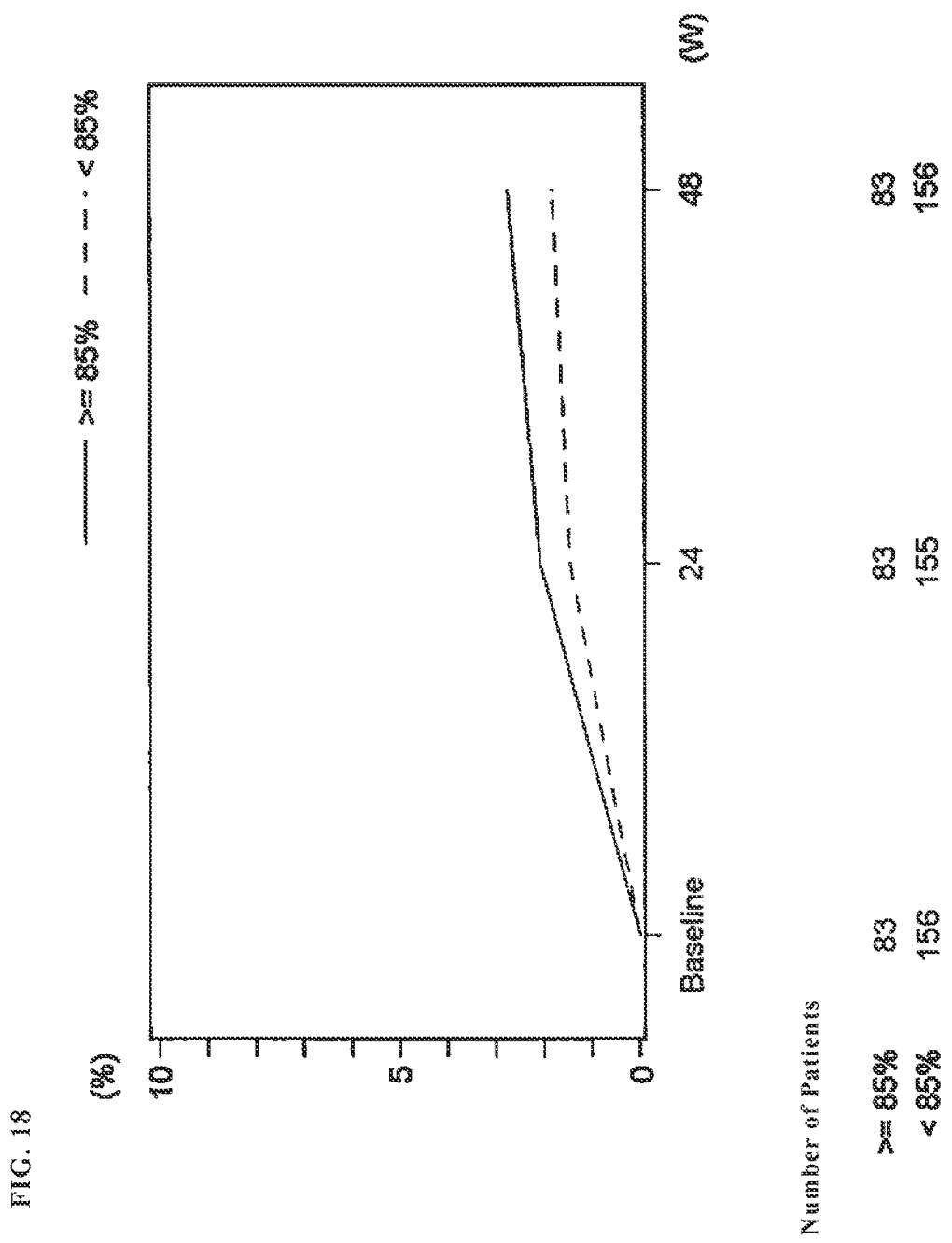
Figure 19:
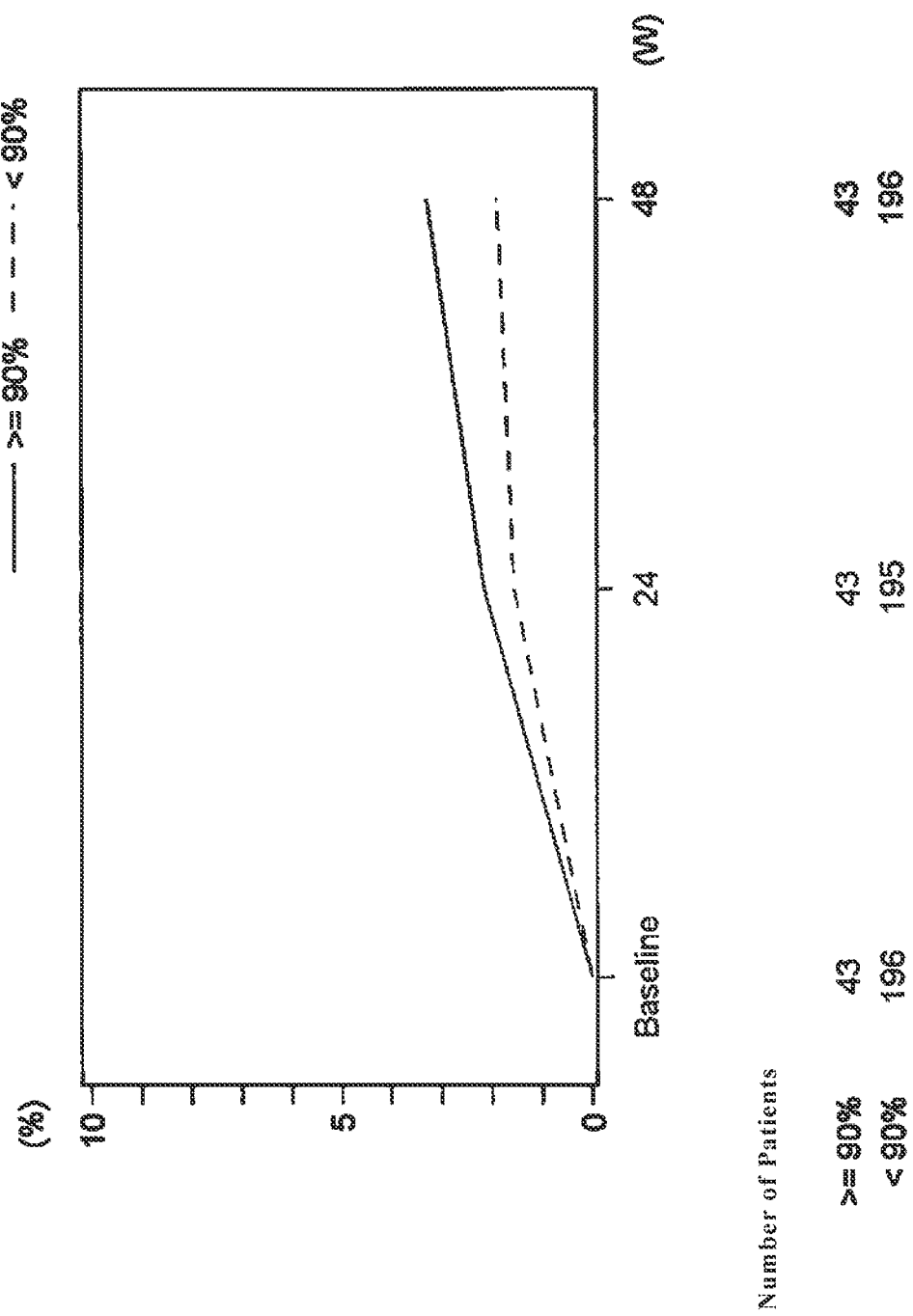
Figure 20:
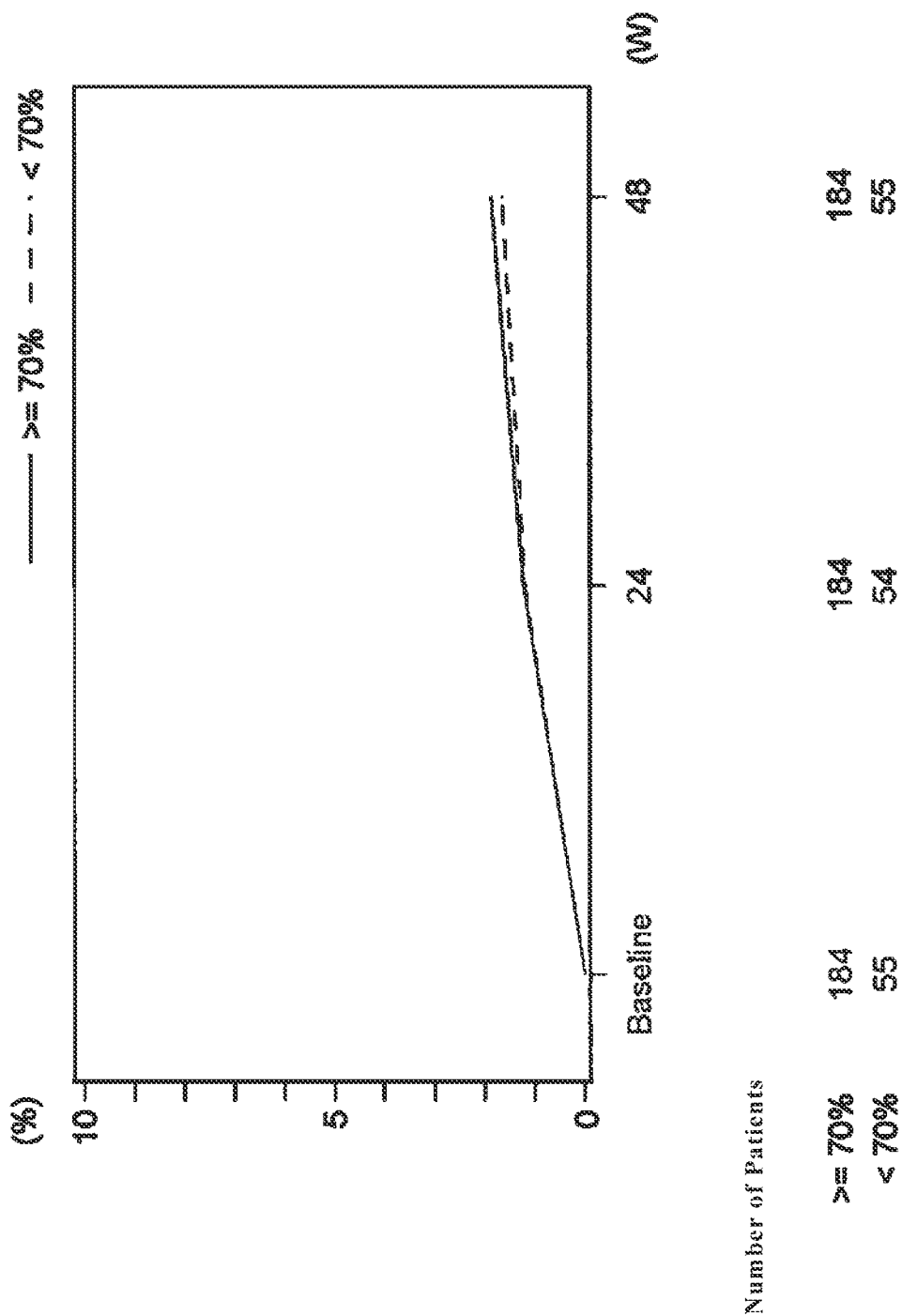
Figure 21:
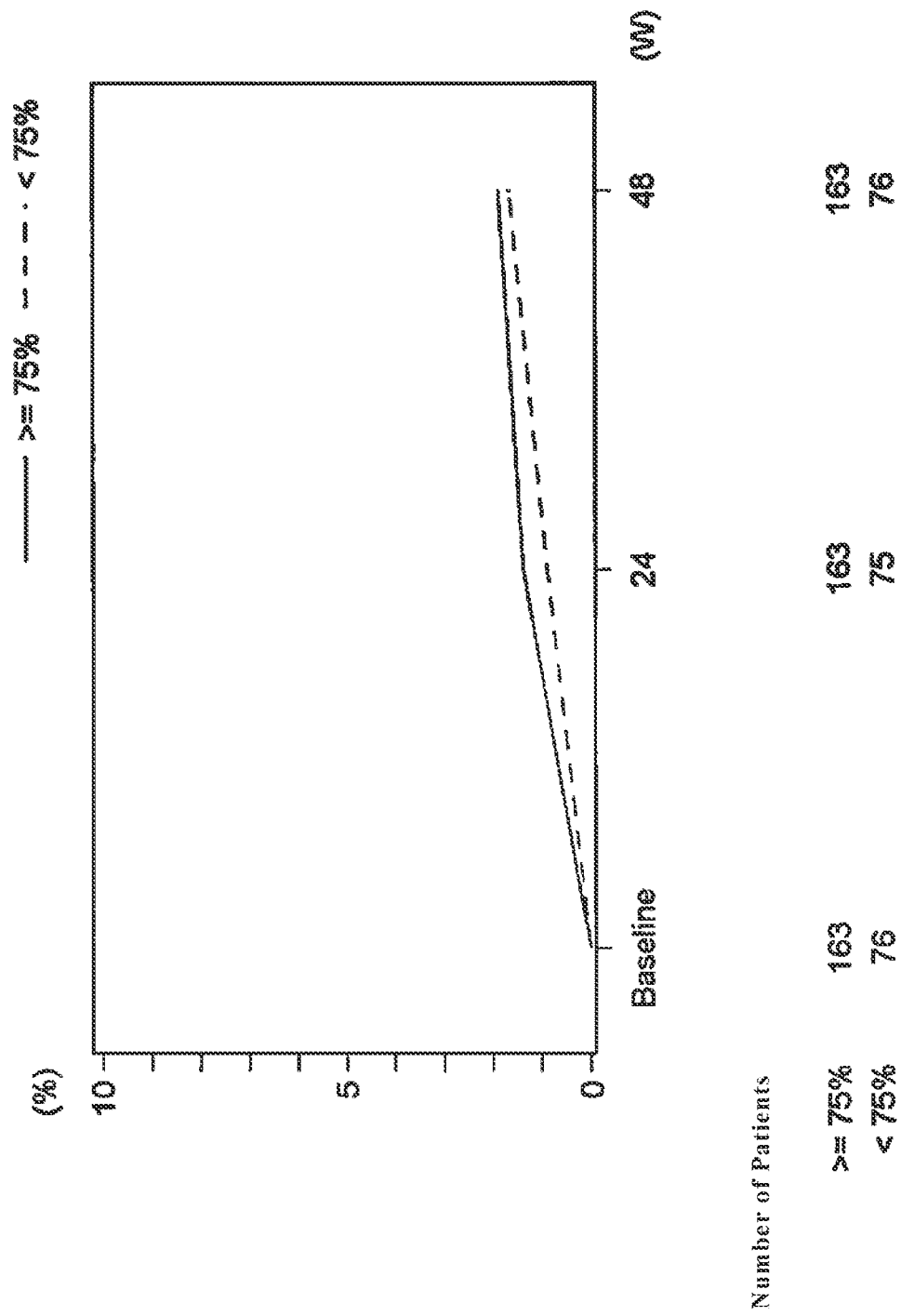
Figure 22:
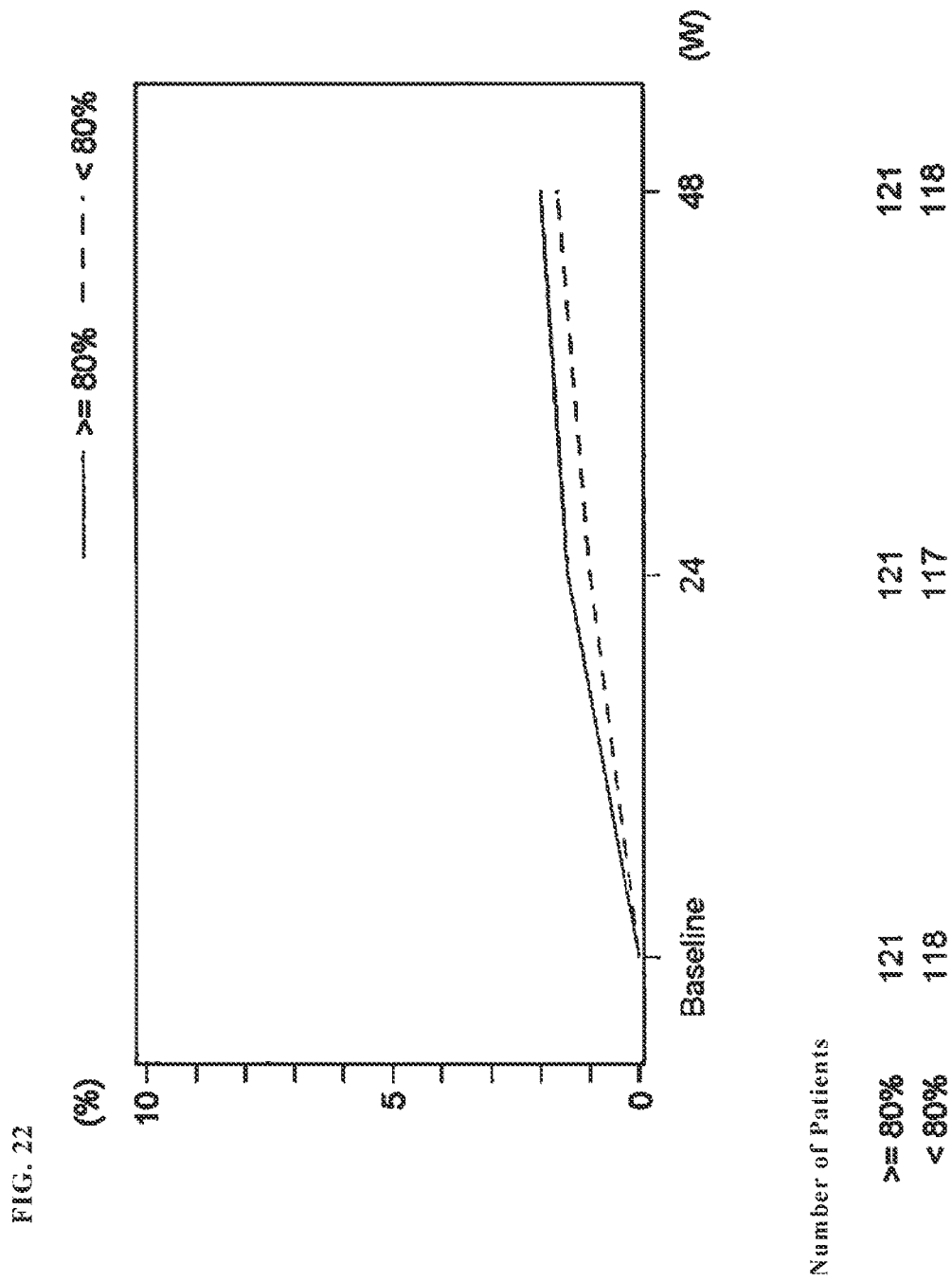
Figure 23:
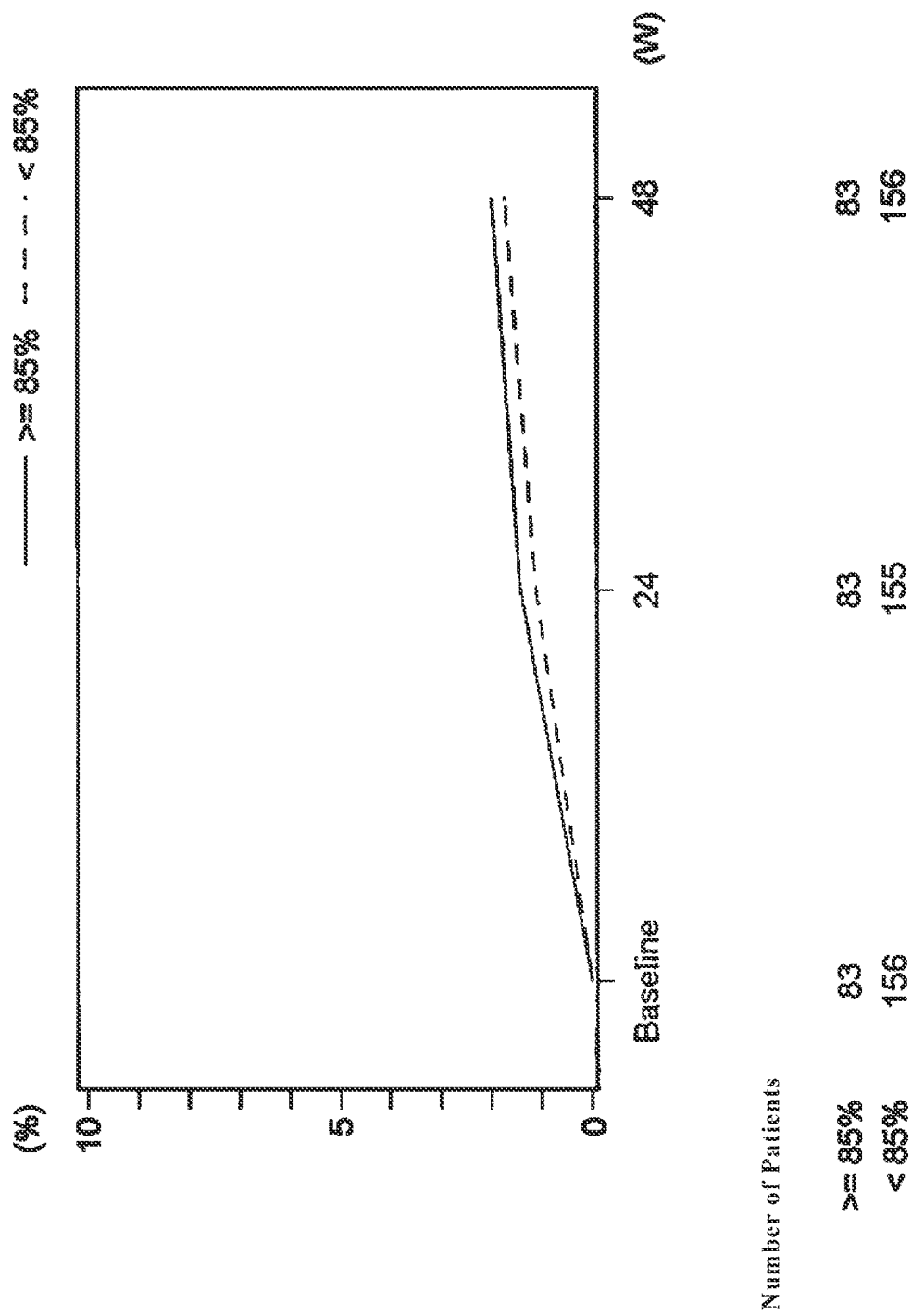
Figure 24:
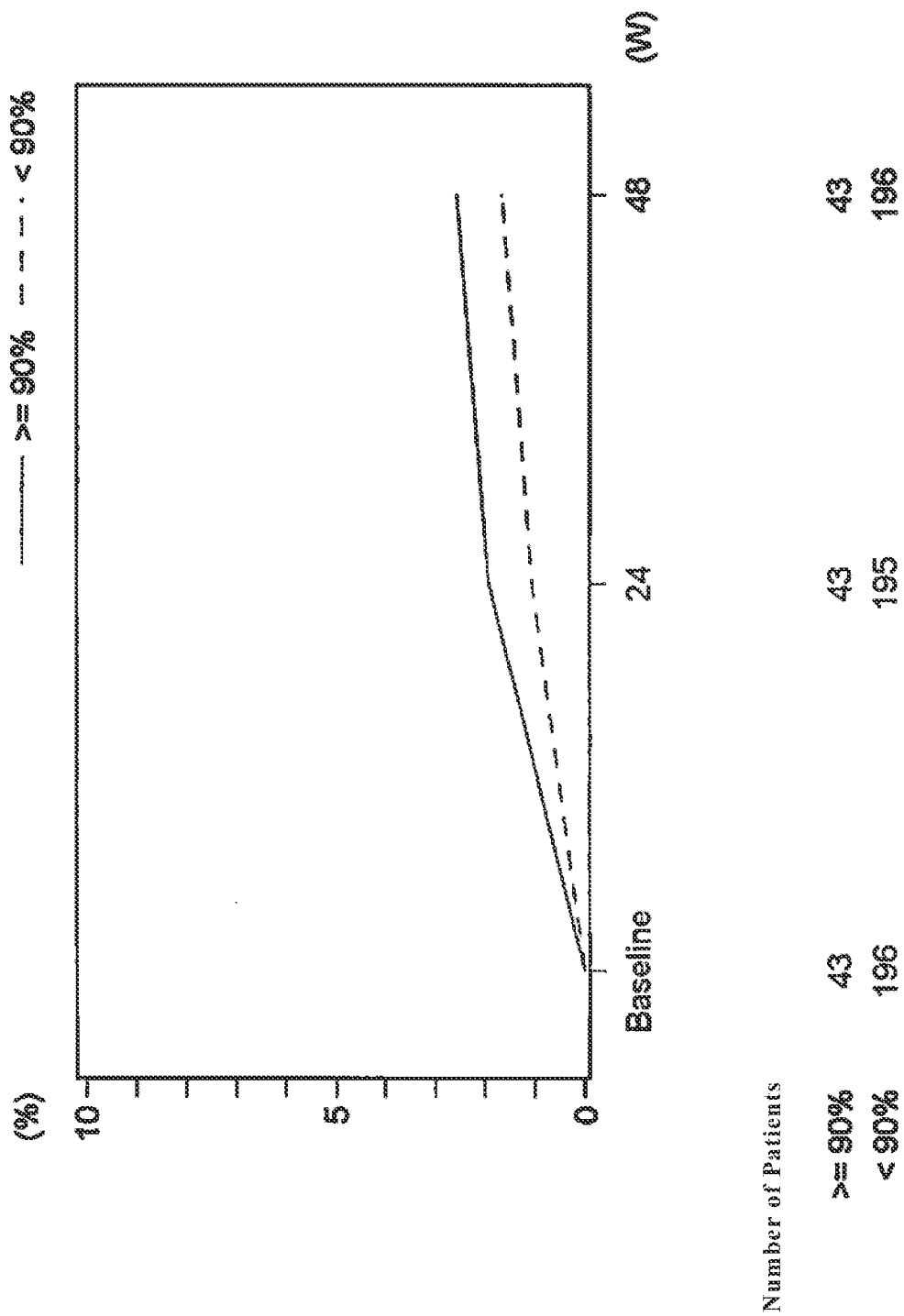

The time transitions of the bone formation markers accompanying the treatment with a test drug were at high levels, as compared to the time transitions of the bone formation markers accompanying the treatment with a control drug (FIGS. 8 and 9). In particular, at an early stage after the beginning of administration (meaning herein until 12 weeks or so after the beginning of administration), the treatment of administration of twice a week had a significantly high change rate in the bone formation markers, as compared to the treatment of administration of once a week. In other words, it can be considered that an increase in bone formation is excellent, whereby it can be thought that the treatment of administration of twice a week possibly shows an even larger increase rate of bone mineral density, as compared to that of the treatment of administration of once a week.

2.8. Safety:

The following aggregate analysis was performed by defining as test individuals subjects to be analyzed for safety who were administered with a test drug or a control drug in the treatment phase at least one or more times. The treatment-emergent adverse event (TEAE) means adverse events that emerged in the treatment phase.

2.8.1. Expression Ratios of Adverse Events and Side Effects (Outline):

TABLE 2-23

Expression ratios of adverse events and side effects

|  |  | No. of assessed cases | No. of expressed cases | Expression ratio (%) | Difference | 95% Confidence interval of difference |
|---|---|---|---|---|---|---|
| Adverse events | Test Drug Group | 277 | 245 | 88.4 | -0.7 | -5.9 to 4.6 |
|  | Control Drug Group | 276 | 246 | 89.1 |  |  |
| Side effects | Test Drug Group | 277 | 110 | 39.7 | -16.4 | -24.7 to -8.2 |
|  | Control Drug Group | 276 | 155 | 56.2 |  |  |

The expression ratio for side effects by the administration of a test drug was markedly decreased, as compared to the expression ratio for side effects by the administration of a control drug.

TABLE 2-24

Expression ratios for adverse events and side effects relating to TEAE

|  |  | No. of cases of Test Drug Group (%) | No. of cases of Control Drug Group (%) |
|---|---|---|---|
| TEAE | Adverse events | 245 (88.4) | 246 (89.1) |
|  | Side effects | 110 (39.7)* | 155 (56.2) |
| Serious adverse events | Adverse events | 20 (7.2) | 24 (8.7) |
|  | Side effects | 1 (0.4) | 4 (1.4) |
| Other important adverse events | Adverse events | 16 (5.8) | 27 (9.8) |
|  | Side effects | 11 (4.0) | 24 (8.7) |

*p < 0.01

The expression ratios for side effects were classified into three, the expression ratio for side effects of TEAE, the expression ratio for side effects of serious adverse events, and the expression ratio for side effects of other important adverse events to analyze. As a result, the expression ratio for side effects by the administration of a test drug was markedly decreased as compared to the expression ratio for side effects by the administration of a control drug in all of the expression ratios for side effects. The important adverse events as used herein were defined as adverse events that resulted in being serious or in discontinuation. In addition, the adverse events excluding "the serious adverse events" from "the important adverse events" were defined as "other important adverse events."

2.8.2. Expression Ratios for Adverse Events and Side Effects Having Relatively High Expression Ratios (Nausea, Vomiting or the like):

TABLE 2-25

Expression ratios for adverse events and side effects relating to nausea, vomiting or the like having relatively high expression ratios

| Rough classification by organs |  | Test Drug Group no. of cases (%) | | Control Drug Group no. of cases (%) | |
|---|---|---|---|---|---|
|  |  | Adverse events | Side effects | Adverse events | Side effects |
| Nervous system disorders | Headache | 18 (6.5)* | 16 (5.8)* | 36 (13.0) | 29 (10.5) |
| Gastro-intestinal disorders | Nausea | 60 (21.7)** | 56 (20.2)** | 92 (33.3) | 88 (31.9) |
|  | Vomiting | 33 (11.9) | 25 (9.0) | 38 (13.8) | 36 (13.0) |
| General and systemic disorders and administration site conditions | Malaise | 28 (10.1) | 26 (9.4) | 35 (12.7) | 33 (12.0) |
|  | Fervescence | 4 (1.4)** | 3 (1.1)** | 19 (6.9) | 18 (6.5) |

*p < 0.05,
**p < 0.01

The expression ratios for adverse events and side effects relating to nausea, vomiting or the like having relatively high expression rations that are common in both the groups showed a low tendency in Test Drug Group, as compared to those of Control Drug Group. In addition, the expression ratios for adverse events and side effects of "headache" or "fervescence" showed a low tendency in Test Drug Group, as compared to those of Control Drug Group.

2.8.3. Expression Ratios for Adverse Events and Side Effects for Each Organ (Nervous System Disorders or the Like):

TABLE 2-26

Expression ratios for adverse events and side effects relating to nervous system disorders or the like for each organ

| Rough classification by organs | Test Drug Group no. of cases (%) | | Control Drug Group no. of cases (%) | |
|---|---|---|---|---|
|  | Adverse events | Side effects | Adverse events | Side effects |
| Nervous system disorders | 49 (17.7) | 24 (8.7) | 70 (25.4) | 41 (14.9) |
| Gastrointestinal disorders | 116 (41.9) | 74 (26.7) | 130 (47.1) | 96 (34.8) |
| General and systemic disorders and administration site conditions | 67 (24.2) | 48 (17.3) | 94 (34.1) | 84 (30.4) |
| Cardiac disorders | 7 (2.5) | 3 (1.1) | 19 (6.9) | 13 (4.7) |
| Vascular disorders | 7 (2.5) | 2 (0.7) | 11 (4.0) | 5 (1.8) |

As a result of the aggregate analysis of the adverse events and the side effects for each organ, the expression ratios for adverse events and side effects showed a low tendency in Test Drug Group, as compared to those of Control Drug Group in all the disorders or conditions of the nervous system disorders, the gastrointestinal disorders, the general and systemic disorders and administration site conditions, the cardiac disorders, and the vascular disorders.

2.8.4. Expression Ratios for Adverse Events and Side Effects (Shocks, Blood Pressure Drop, Unconsciousness) and Change in Blood Pressure in Time Course:

TABLE 2-27

Expression ratios for adverse events and side effects relating to shocks or the like

|  | Test Drug Group no. of cases (%) | | Control Drug Group no. of cases (%) | |
|---|---|---|---|---|
|  | Adverse events | Side effects | Adverse events | Side effects |
| Events associated with shocks | 0 (0.0) | 0 (0.0) | 0 (0.0) | 0 (0.0) |
| Events associated with blood pressure drop | 3 (1.1) | 3 (1.1) | 8 (2.9) | 7 (2.5) |
| Events associated with unconsciousness | 0 (0.0) | 0 (0.0) | 1 (0.4) | 0 (0.0) |

As mentioned above, it has been known that shocks, or unconsciousness accompanying a transient drastic blood pressure drop, convulsion, or fall is found from immediately after the administration over several hours of a daily administered preparation or a once-weekly administered preparation of PTH (Non-Patent Publications 4 and 8).

Here, as to the events associated with blood pressure drop, the expression ratios for adverse events and side effects showed a low tendency in Test Drug Group as compared to those of Control Drug Group. Further, as to the events associated with shocks or unconsciousness, Test Drug Group showed excellent safety such that the expression of adverse events and side effects was not found at all.

TABLE 2-28

Time transitions of change in systolic blood pressure after administration to that administration before administration

| Test timing | Timing after administration | Test Drug Group No. of cases | Test Drug Group Mean (mmHg) | Control Drug Group No. of cases | Control Drug Group Mean (mmHg) |
|---|---|---|---|---|---|
| After 0 weeks | 10 min. after administration | 274 | −6.3 | 275 | −8.9 |
|  | Before returning home | 276 | −7.5 | 275 | −12.2 |
| After 4 weeks | 10 min. after administration | 266 | −8.0 | 266 | −9.6 |
|  | Before returning home | 266 | −7.8 | 266 | −10.9 |
| After 12 weeks | 10 min. after administration | 263 | −7.0 | 253 | −8.8 |
|  | Before returning home | 263 | −7.0 | 253 | −10.8 |
| After 24 weeks | 10 min. after administration | 251 | −7.9 | 244 | −8.2 |
|  | Before returning home | 251 | −9.4 | 244 | −11.6 |
| After 48 weeks | 10 min. after administration | 241 | −6.7 | 233 | −7.4 |
|  | Before returning home | 241 | −6.5 | 233 | −7.5 |

In Test Drug Group, the dropping tendencies of the mean value of the change rates in systolic blood pressure (value after administration−value before administration) were the same for all of the test timings (after 0, 4, 12, 24 and 48 weeks). On the other hand, in Control Drug Group, the same mean value particularly had a large dropping range after 0, 4, and 12 weeks, as compared to that of Test Drug Group. The extent of blood pressure drop was from −6.3 to −9.4 mmHg in Test Drug Group, and from −7.4 to −12.2 mmHg in Control Drug Group, so that the blood pressure drop in Test Drug Group were mild as compared to the blood pressure drop in Control Drug Group.

TABLE 2-29

Time transitions of change in diastolic blood pressure after administration to that before administration

| Test Timing | Timing after administration | Test Drug Group No. of cases | Test Drug Group Mean (mmHg) | Control Drug Group No. of cases | Control Drug Group Mean (mmHg) |
|---|---|---|---|---|---|
| After 0 weeks | 10 min. after administration | 274 | −4.4 | 275 | −6.6 |
|  | Before returning home | 276 | −4.9 | 275 | −8.0 |
| After 4 weeks | 10 min. after administration | 266 | −4.4 | 266 | −5.7 |
|  | Before returning home | 266 | −4.8 | 266 | −7.4 |
| After 12 weeks | 10 min. after administration | 263 | −4.7 | 253 | −5.7 |
|  | Before returning home | 263 | −5.0 | 253 | −7.3 |
| After 24 weeks | 10 min. after administration | 251 | −4.6 | 244 | −4.8 |
|  | Before returning home | 251 | −6.3 | 244 | −7.0 |
| After 48 weeks | 10 min. after administration | 241 | −5.0 | 233 | −4.3 |
|  | Before returning home | 241 | −4.2 | 233 | −4.8 |

In Test Drug Group, the dropping tendencies of the mean value of the change rate in diastolic blood pressure (value after the administration−value before the administration) were the same for all of the test timings (after 0, 4, 12, 24 and 48 weeks). On the other hand, in Control Drug Group, the same mean value particularly had a large dropping range after 0, 4, and 12 weeks. The extent of blood pressure drop was from −4.2 to −6.3 mmHg in Test Drug Group, and from −4.3 to −8.0 mmHg in Control Drug Group, so that the blood pressure drop in Test Drug Group were mild as compared to the blood pressure drop in Control Drug Group.

2.8.5. Expression Ratios for Adverse Events and Side Effects by Age Groups:

TABLE 2-30

Expression ratios for adverse events and side effects by age groups:

| | No. of cases of Test Drug Group (%) | | | No. of cases of Control Drug Group (%) | | |
|---|---|---|---|---|---|---|
| | Ages | | | | | |
| | Age 65 or older and age younger than 75 | Age 75 or older and age younger than 80 | Age 80 or older | Age 65 or older and age younger than 75 | Age 75 or older and age younger than 80 | Age 80 or older |
| TEAE (adverse events) | 131 (88.5) | 72 (91.1) | 42 (84.0) | 132 (89.8) | 63 (91.3) | 51 (85.0) |
| TEAE (side effects) | 72 (48.6) | 28 (35.4) | 10 (20.0) | 89 (60.5) | 38 (55.1) | 28 (46.7) |

The tendencies of decreasing the expression ratios in the frequency of side effects by aging were even more strongly observed in Test Drug Group, and in particular, the expression ratios of the frequency of side effects were markedly lowered in the patients of Test Drug Group of age 80 or older.

2.8.6. Expression Ratios for Adverse Events and Side Effects by Gender Groups:

TABLE 2-31

Expression ratios for adverse events and side effects by gender groups

|  |  | No. of cases of Test Drug Group (%) | | No. of cases of Control Drug Group (%) | |
| --- | --- | --- | --- | --- | --- |
|  |  | Female | Male | Female | Male |
| TEAE | Adverse event | 223 (88.5) | 22 (88.0) | 225 (89.6) | 21 (84.0) |
|  | Side effects | 107 (42.5) | 3 (12.0) | 143 (57.0) | 12 (48.0) |
| Serious adverse events | Adverse event | 19 (7.5) | 1 (4.0) | 20 (8.0) | 4 (16.0) |
|  | Side effects | 1 (0.4) | 0 (0.0) | 4 (1.6) | 0 (0.0) |
| Other important adverse events | Adverse event | 16 (6.3) | 0 (0.0) | 26 (10.4) | 1 (4.0) |
|  | Side effects | 11 (4.4) | 0 (0.0) | 23 (9.2) | 1 (4.0) |

Test Drug Group showed excellent safety regardless of the genders, as compared to those of Control Drug Group, and in particular male individuals had remarkably decreased expression ratios for side effects.

2.8.7. Treatment Continuality:

TABLE 2-32

Treatment continuality

|  | No. of cases of Test Drug Group (%) | No. of cases of Control Drug Group (%) |
| --- | --- | --- |
| Test individuals who began the treatment | 277 (100.0) | 276 (100.0) |
| Test individuals who discontinued the treatment | 35 (12.6) | 41 (14.9) |
| Test individuals who completed the treatment | 242 (87.4) | 235 (85.1) |

The treatment continuality showed high tendencies in Test Drug Group as compared to those of Control Drug Group.

TABLE 2-33

Reasons why the treatment was discontinued

|  | Reason for discontinuation | No. of cases at 0 to 24 weeks | No. of cases at 24 to 48 weeks | No. of cases at 48 weeks or more | Total no. of cases (%) |
| --- | --- | --- | --- | --- | --- |
| Test Drug Group | Adverse events | 11 | 9 | 2 | 22 (62.9) |
|  | Judgment of physician | 1 | 0 | 0 | 1 (2.9) |
|  | Departure from protocol of investigational studies | 1 | 0 | 0 | 1 (2.9) |

TABLE 2-33-continued

Reasons why the treatment was discontinued

|  | Reason for discontinuation | No. of cases at 0 to 24 weeks | No. of cases at 24 to 48 weeks | No. of cases at 48 weeks or more | Total no. of cases (%) |
| --- | --- | --- | --- | --- | --- |
|  | Ineligibility of compliance | 1 | 0 | 0 | 1 (2.9) |
|  | Judgment of patients | 6 | 4 | 0 | 10 (28.6) |
|  | Total | 20 | 13 | 2 | 35 (100.0) |
| Control Drug Group | Adverse events | 25 | 5 | 0 | 30 (73.2) |
|  | Judgment of physician | 2 | 1 | 0 | 3 (7.3) |
|  | Judgment of patients | 5 | 3 | 0 | 8 (19.5) |
|  | Total | 32 | 9 | 0 | 41 (100.0) |

The proportion of discontinuation of the treatment due to adverse events was low in Test Drug Group as compared to that of Control Drug Group. In addition, the discontinuation due to adverse events at less than 24 weeks was 11 individuals in Test Drug Group, in contrast to 25 individuals in Control Drug Group, so that in Test Drug Group, the discontinuation cases due to adverse events at an early stage of the treatment was particularly fewer.

TABLE 2-34

Breakdown of adverse events resulted in discontinuation of treatment

|  | No. of cases of Test Drug Group (%) | | No. of cases of Control Drug Group (%) | |
| --- | --- | --- | --- | --- |
| Events | Adverse events | Side effects | Adverse events | Side effects |
| Headache | 3 (1.1) | 3 (1.1) | 3 (1.1) | 3 (1.1) |
| Nausea | 6 (2.2) | 6 (2.2) | 12 (4.3) | 11 (4.0) |
| Vomiting | 2 (0.7) | 2 (0.7) | 5 (1.8) | 5 (1.8) |
| Dysesthesia | 2 (0.7) | 1 (0.4) | 3 (1.1) | 2 (0.7) |
| Fervescence | 1 (0.4) | 1 (0.4) | 4 (1.4) | 4 (1.4) |

(Provided that only events that were expressed in 3 or more cases)

The treatment with Test Drug Group was found to have improvements in the treatment continuality by decreasing the expression ratios of adverse events or side effects such as nausea and vomiting, as compared to the treatment with Control Drug Group.

2.9. Analysis of Influences by Administration Intervals on Therapeutic Effects:

2.9.1. Method of Analysis:

Using 242 test individuals who completed the treatment over 48 weeks out of Test Drug Group (hereinafter referred to as Test Drug Group with Treatment Completed) as subjects, the proportion occupying the weeks in which the intervals of administration in a week (not including the days of administration) out of 48 weeks, the number of weeks of the entire period of administration, were 2-day and 3-day intervals (%) (hereinafter referred to as the proportion in compliance with administration of 2-day to 3-day intervals) was calculated for each test individual. At this time, it was considered that the weeks that satisfy the following conditions (1) or (2) did not fall under the weeks in which the intervals of administration in a week (not including the days of administration) were 2-day and 3-day intervals.

(1) Weeks in a case where the period of the course from the day on which a control drug placebo was administered to the day on which a next control drug placebo was administered was within 6 days.

TABLE 2-35

Case where the period of the course from the day on which a control drug placebo
was administered to the day on which a next control drug placebo was administered
was 5 days (Days 1 to 7 in the following table fall under the above weeks)

|  | Day 1 | Day 2 | Day 3 | Day 4 | Day 5 | Day 6 | Day 7 | Day 8 | Day 9 |
|---|---|---|---|---|---|---|---|---|---|
| Test drug | ● |  |  | ● |  |  |  | ● |  |
| Control drug placebo | ○ |  |  |  |  | ○ |  |  |  |

(2) Weeks in a case where a test drug was administered without intervals of administration, or administered with a 1-day administration interval, a 4-day administration interval, and a 5-day administration interval, when the period of the course from the day on which a control drug placebo was administered to the day on which a next control drug placebo was administered was 7 or more days.

TABLE 2-36

Cases of weeks where a test drug was administered without intervals of administration,
when the period of the course from the day on which a control drug placebo was administered
to the day on which a next control drug placebo was administered was 7 or more days
(Days 1 to 7 in the following table fall under the above weeks)

|  | Day 1 | Day 2 | Day 3 | Day 4 | Day 5 | Day 6 | Day 7 | Day 8 | Day 9 |
|---|---|---|---|---|---|---|---|---|---|
| Test drug | ● | ● |  |  |  |  |  | ● |  |
| Control drug placebo | ○ |  |  |  |  |  |  | ○ |  |

TABLE 2-37

Cases of weeks where a test drug was administered with a 1-day administration interval,
when the period of the course from the day on which a control drug placebo was administered
to the day on which a next control drug placebo was administered was 7 or more days
(Days 1 to 7 in the following table fall under the above weeks)

|  | Day 1 | Day 2 | Day 3 | Day 4 | Day 5 | Day 6 | Day 7 | Day 8 | Day 9 |
|---|---|---|---|---|---|---|---|---|---|
| Test drug | ● |  | ● |  |  |  |  | ● |  |
| Control drug placebo | ○ |  |  |  |  |  |  | ○ |  |

TABLE 2-38

Cases of weeks where a test drug was administered with a 4-day administration interval,
when the period of the course from the day on which a control drug placebo was administered
to the day on which a next control drug placebo was administered was 7 or more days
(Days 1 to 7 in the following table fall under the above weeks)

|  | Day 1 | Day 2 | Day 3 | Day 4 | Day 5 | Day 6 | Day 7 | Day 8 | Day 9 |
|---|---|---|---|---|---|---|---|---|---|
| Test drug | ● |  |  |  |  | ● |  | ● |  |
| Control drug placebo | ○ |  |  |  |  |  |  | ○ |  |

TABLE 2-39

Cases of weeks where a test drug was administered with a 5-day administration interval,
when the period of the course from the day on which a control drug placebo was administered
to the day on which a next control drug placebo was administered was 7 or more days
(Days 1 to 7 in the following table fall under the above weeks)

|  | Day 1 | Day 2 | Day 3 | Day 4 | Day 5 | Day 6 | Day 7 | Day 8 | Day 9 |
|---|---|---|---|---|---|---|---|---|---|
| Test drug | ● |  |  |  |  |  |  | ● | ● |
| Control drug placebo | ○ |  |  |  |  |  |  | ○ |  |

Having defined the proportion in compliance with administration of 2-day to 3-day intervals as described above, the following five aggregate analyses were carried out.

(1) The comparative analysis on efficacies and safety of Test Drug Group with Treatment Completed with a proportion in compliance with administration of 2-day to 3-day intervals of 70% or more and Test Drug Group with Treatment Completed with a proportion in compliance with administration of 2-day to 3-day intervals is less than 70%.

(2) The comparative analysis on efficacies and safety of Test Drug Group with Treatment Completed with a proportion in compliance with administration of 2-day to 3-day intervals of 75% or more and Test Drug Group with Treatment Completed with a proportion in compliance with administration of 2-day to 3-day intervals is less than 75%.

(3) The comparative analysis on efficacies and safety of Test Drug Group with Treatment Completed with a proportion in compliance with administration of 2-day to 3-day intervals of 80% or more and Test Drug Group with Treatment Completed with a proportion in compliance with administration of 2-day to 3-day intervals is less than 80%.

(4) The comparative analysis on efficacies and safety of Test Drug Group with Treatment Completed with a proportion in compliance with administration of 2-day to 3-day intervals of 85% or more and Test Drug Group with Treatment Completed with a proportion in compliance with administration of 2-day to 3-day intervals is less than 85%.

(5) The comparative analysis on efficacies and safety of Test Drug Group with Treatment Completed with a proportion in compliance with administration of 2-day to 3-day intervals of 90% or more and Test Drug Group with Treatment Completed with a proportion in compliance with administration of 2-day to 3-day intervals is less than 90%.

Here, the assessment items for the efficacies were change rates in bone mineral densities of lumbar vertebrae (second to fourth lumbar vertebrae), change rates in bone mineral densities of femoral neck part, change rates in bone mineral densities of femoral proximal total, clinical fracture incidence rates, and non-vertebral fracture incidence rates. In addition, the assessment items for the safety were the expression ratios of all the side effects and the expression ratios of nausea (side effects).

Further, the mean of the number of administrations and the mean of the number of the administration period in each group to be compared were calculated.

2.9.2. Analysis Results:
2.9.2.1. Mean of Number of Administrations and Mean of Administration Period:

Using 242 individuals of Test Drug Group with Treatment Completed as subjects, the mean of the number of administrations and the mean of the administration period were calculated for each of the proportions in compliance with administration intervals. The results are shown in the following Table 2-40.

TABLE 2-40

Mean of number of administrations and mean of administration period (days) when distinguished by a specified value or more/less than a specified value of each of the proportions in compliance with administration of 2-day to 3-day intervals

| Proportion in compliance with administration of 2-day to 3-day intervals | | No. of Cases | Mean of Number of Administration | Mean of Administration Period (Days) |
|---|---|---|---|---|
| 70% | or more | 186 | 90.2 | 332.3 |
|  | less than | 56 | 87.1 | 332.1 |
| 75% | or more | 165 | 90.3 | 332.1 |
|  | less than | 77 | 87.7 | 332.5 |
| 80% | or more | 122 | 90.6 | 332.4 |
|  | less than | 120 | 88.3 | 332.1 |
| 85% | or more | 83 | 91.8 | 332.8 |
|  | less than | 159 | 88.2 | 332.0 |
| 90% | or more | 43 | 93.0 | 333.1 |
|  | less than | 199 | 88.7 | 332.1 |

In the comparisons of both cases when distinguished by 70% or more and that of less than 70% of the proportion in compliance with administration of 2-day to 3-day intervals, there were no significance differences in the mean of the number of administrations and the mean of the administration period, and were of the same levels. In the cases of comparing a specified value or more and less than a specified value for each of the values for the proportion in compliance with administration of 2-day to 3-day intervals of 75%, 80%, 85% and 90%, similar results were also obtained as the case where a proportion in compliance with administration of 2-day to 3-day intervals of 70% or more. Therefore, it was considered that there were no differences in the mean of the number of administrations and the mean of the administration period even in different proportions in compliance with administration of 2-day to 3-day intervals, so that there are no differences in the exposed amount of the investigational product.

2.9.2.2. Mean Value of Change Rates in Bone Mineral Densities for Each of Lumbar Vertebrae, Femoral Neck Part, and Femoral Proximal Total when Distinguished by Specified Value or More/Less than Specified Value of Each of Proportions in Compliance with Administration of 2-Day to 3-Day Intervals (%):

The mean value of change rates (%) when distinguished by a specified value or more/less than a specified value in bone mineral densities for the lumbar vertebrae, the femoral neck part, and the femoral proximal total was calculated of the proportions in compliance with administration of 2-day to 3-day intervals. The results are shown in the following Tables 2-41 to 2-43.

TABLE 2-41

Mean value of change rates (%) distinguished by a specified value or more/less than a specified value in bone mineral densities of lumbar vertebrae (second to fourth lumbar vertebrae) of each of the proportions in compliance with the administration of 2-day to 3-day intervals

| Proportion in compliance with administration of 2-day to 3-day intervals | | After 24 weeks | After 48 weeks |
|---|---|---|---|
| 70% | or more | 5.0 | 7.5 |
|  | less than | 4.9 | 7.4 |
| 75% | or more | 5.1 | 7.6 |
|  | less than | 4.8 | 7.2 |
| 80% | or more | 5.3 | 8.0 |
|  | less than | 4.7 | 7.0 |
| 85% | or more | 5.5 | 8.0 |
|  | less than | 4.8 | 7.2 |
| 90% | or more | 5.8 | 8.6 |
|  | less than | 4.9 | 7.3 |

TABLE 2-42

Mean value of change rates (%) when distinguished by a specified value or more/less than a specified value in bone mineral densities of the femoral neck part of each of the proportions in compliance with the administration of 2-day to 3-day intervals

| Proportion in compliance with administration of 2-day to 3-day intervals | | After 24 weeks | After 48 weeks |
|---|---|---|---|
| 70% | or more | 1.5 | 2.1 |
|  | less than | 2.3 | 2.4 |
| 75% | or more | 1.6 | 2.2 |
|  | less than | 1.9 | 2.1 |
| 80% | or more | 1.8 | 2.5 |
|  | less than | 1.6 | 1.8 |
| 85% | or more | 2.1 | 2.8 |
|  | less than | 1.5 | 1.8 |
| 90% | or more | 2.2 | 3.3 |
|  | less than | 1.6 | 1.9 |

TABLE 2-43

Mean value of change rates (%) when distinguished by a specified value or more/less than a specified value in bone mineral densities of the femoral proximal total of each of the proportions in compliance with the administration of 2-day to 3-day intervals

| Proportion in compliance with administration of 2-day to 3-day intervals | | After 24 weeks | After 48 weeks |
|---|---|---|---|
| 70% | or more | 1.2 | 1.9 |
|  | less than | 1.2 | 1.7 |
| 75% | or more | 1.4 | 1.9 |
|  | less than | 0.9 | 1.7 |
| 80% | or more | 1.4 | 2.0 |
|  | less than | 1.0 | 1.6 |
| 85% | or more | 1.4 | 2.0 |
|  | less than | 1.1 | 1.7 |
| 90% | or more | 1.9 | 2.6 |
|  | less than | 1.1 | 1.7 |

In addition, graphs showing the transitions of the mean value of change rates (%) in each of the bone mineral densities of lumbar vertebrae (second to fourth lumbar vertebrae), the bone mineral densities of the femoral neck part, and the bone mineral densities of the femoral proximal total by comparing the values of a specified value or more/less than a specified value for each of the proportions in compliance with the administration of 2-day to 3-day intervals are shown in FIGS. 10 to 24.

Figure 25:
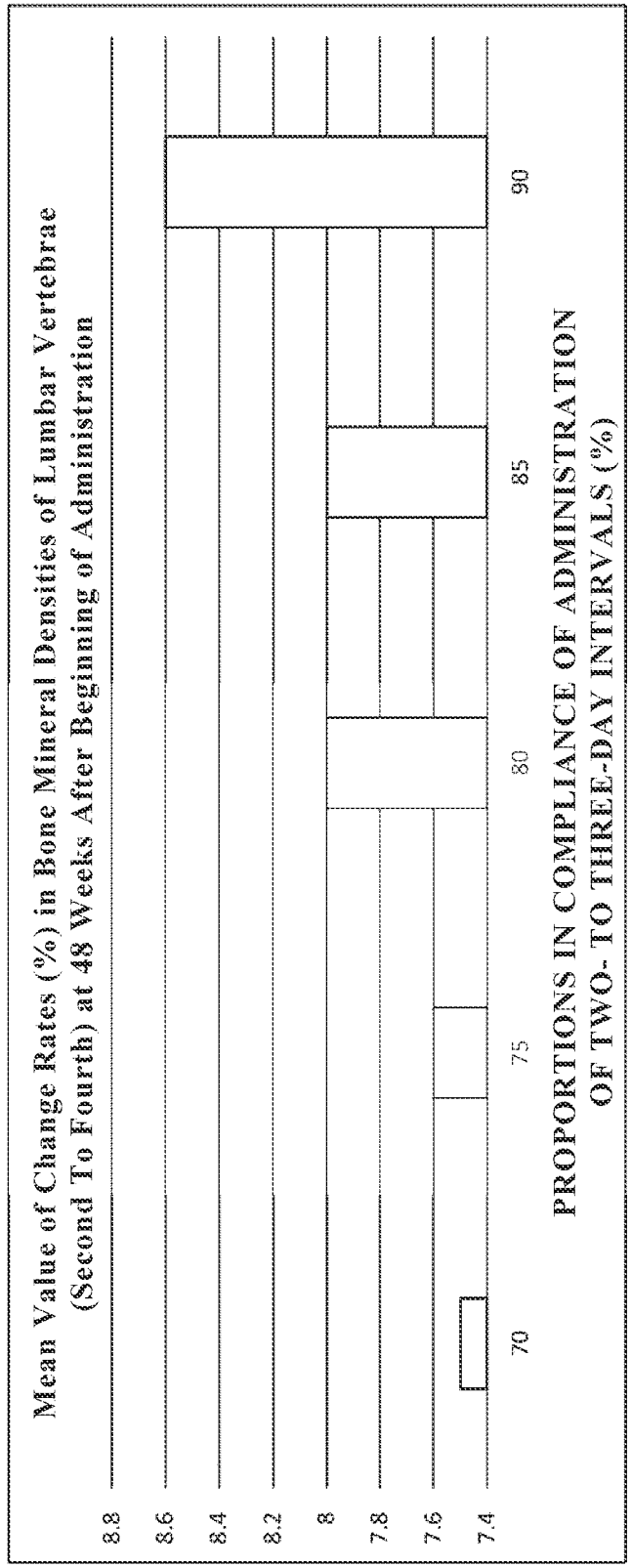

As mentioned above, the bone mineral densities of lumbar vertebrae (second to fourth lumbar vertebrae) are a main assessment item for the efficacies of the present test. In view of the above, the analysis results on the influences given by fluctuations of a specified value to the mean value of change rates (%) in bone mineral densities of lumbar vertebrae (second to fourth lumbar vertebrae) indicated by patients having a proportion in compliance with the administration of 2-day to 3-day intervals of a specified value (%) or more at the time point of 48 weeks after the beginning of administration are shown in FIG. 25.

In the layer where the proportion in compliance with the administration of 2-day to 3-day intervals is a specified value or more, the larger the proportion in compliance with the administration of 2-day to 3-day intervals, the mean value of change rates (%) in bone mineral densities tended to be higher. Therefore, it was considered that the higher the proportion occupied by the weeks in which the intervals of administration in a week (not including the days of administration) was 2-day and 3-day intervals, the higher the therapeutic effects obtained. More specifically, excellent therapeutic effects are exhibited in an embodiment where the same proportion is 70% or more, and even more remarkable therapeutic effects can be acquired in an embodiment where the same proportion is 90% or more. Moreover, in taking strong positive correlative tendencies of the same proportion and the therapeutic effects into account, it was considered that the therapeutic effects would be generally maximized when the same proportion is 100%.

On the other hand, there were two cases where the compliance rate of the administration of 2-day to 3-day intervals (3-day to 4-day intervals including the days of administration) was 0%, and the administration was carried out at the frequency of twice a week by generally 1-day and 4-day intervals (2-day and 5-day intervals including the days of administration). The mean of change rates (%) in the bone mineral densities of lumbar vertebrae (second to fourth lumbar vertebrae) for these two cases were analyzed. As a result, at 48 weeks after the beginning of the administration, the mean value for one case was 5.8%, and that for the other case was 5.9%. The inventor considers that the results also suggest that it is useful to comply with the administration of 2-day to 3-day intervals (3-day to 4-day intervals including the days of administration) when the administration was carried out twice a week.

2.9.2.3. Mean Value of Change Rates (%) in Bone Mineral Densities in Each Group when Proportions in Compliance with Administration of 2-Day to 3-Day Intervals were Grouped into Those of from 75 to 85%, and Those of from 85 to 100%:

TABLE 2-44

Mean value of change rates (%) in bone mineral densities in each group when the proportions in compliance with the administration of 2-day to 3-day intervals were grouped into those of from 75 to 85%, and those of from 85 to 100%

| | Time Course from Beginning of Administration | 75 to 85% (N = 82) | 85 to 100% (N = 83) |
|---|---|---|---|
| Mean value of change rates (%) in bone mineral densities of lumbar vertebrae (second to fourth lumbar vertebrae) | Week 24 | 4.8% | 5.5% |
| | Week 48 | 7.2% | 8.0% |

TABLE 2-44-continued

Mean value of change rates (%) in bone mineral densities in each group when the proportions in compliance with the administration of 2-day to 3-day intervals were grouped into those of from 75 to 85%, and those of from 85 to 100%

| | Time Course from Beginning of Administration | 75 to 85% (N = 82) | 85 to 100% (N = 83) |
|---|---|---|---|
| Mean value of change rates (%) in bone mineral densities of femoral proximal total | Week 24 | 1.3% | 1.4% |
| | Week 48 | 1.8% | 2.0% |
| Bone fracture incidence rate (%) of clinical bone fractures | | 12.2% | 7.2% |

2.9.2.4. Incidence Rates of Clinical Bone Fractures and Non-Vertebral Bone Fractures when Distinguished by Specified Value or More/Less than Specified Value of Each of Proportions in Compliance with Administration of 2-Day to 3-Day Intervals:

The incidence rates of clinical bone fractures and non-vertebral bone fractures when distinguished by a specified value or more and less than a specified value of each of the proportions in compliance with the administration of 2-day to 3-day administration were calculated. The results are shown in the following Tables 2-45 to 2-46.

TABLE 2-45

The number of cases of bone fracture incidence and the bone fracture incidence rate (%) of the clinical bone fractures when distinguished by a specified value or more/less than a specified value of each of the proportions in compliance with the administration of 2-day to 3-day intervals

| Proportion in compliance with administration of 2-day to 3-day intervals | | No. of cases of bone fracture assessed | No. of cases of bone fracture incidence | Incidence rate of bone fractures (%) |
|---|---|---|---|---|
| 70% | or more | 186 | 17 | 9.1 |
| | less than | 56 | 6 | 10.7 |
| 75% | or more | 165 | 16 | 9.7 |
| | less than | 77 | 7 | 9.1 |
| 80% | or more | 122 | 10 | 8.2 |
| | less than | 120 | 13 | 10.8 |
| 85% | or more | 83 | 6 | 7.2 |
| | less than | 159 | 17 | 10.7 |
| 90% | or more | 43 | 1 | 2.3 |
| | less than | 199 | 22 | 11.1 |

TABLE 2-46

The number of cases of bone fracture incidence and the bone fracture incidence rate (%) of the non-vertebral bone fractures when distinguished by a specified value or more/less than a specified value of each of the proportions in compliance with the administration of 2-day to 3-day administration intervals

| Proportion in compliance with administration of 2-day to 3-day intervals | | No. of cases of bone fracture assessed | No. of cases of bone fracture incidence | Incidence rate of bone fractures (%) |
|---|---|---|---|---|
| 70% | or more | 186 | 16 | 8.6 |
| | less than | 56 | 6 | 10.7 |
| 75% | or more | 165 | 15 | 9.1 |
| | less than | 77 | 7 | 9.1 |
| 80% | or more | 122 | 9 | 7.4 |
| | less than | 120 | 13 | 10.8 |
| 85% | or more | 83 | 6 | 7.2 |
| | less than | 159 | 16 | 10.1 |

TABLE 2-46-continued

The number of cases of bone fracture incidence and the bone fracture incidence rate (%) of the non-vertebral bone fractures when distinguished by a specified value or more/less than a specified value of each of the proportions in compliance with the administration of 2-day to 3-day administration intervals

| Proportion in compliance with administration of 2-day to 3-day intervals | | No. of cases of bone fracture assessed | No. of cases of bone fracture incidence | Incidence rate of bone fractures (%) |
|---|---|---|---|---|
| 90% | or more | 43 | 1 | 2.3 |
| | less than | 199 | 21 | 10.6 |

Figure 26:
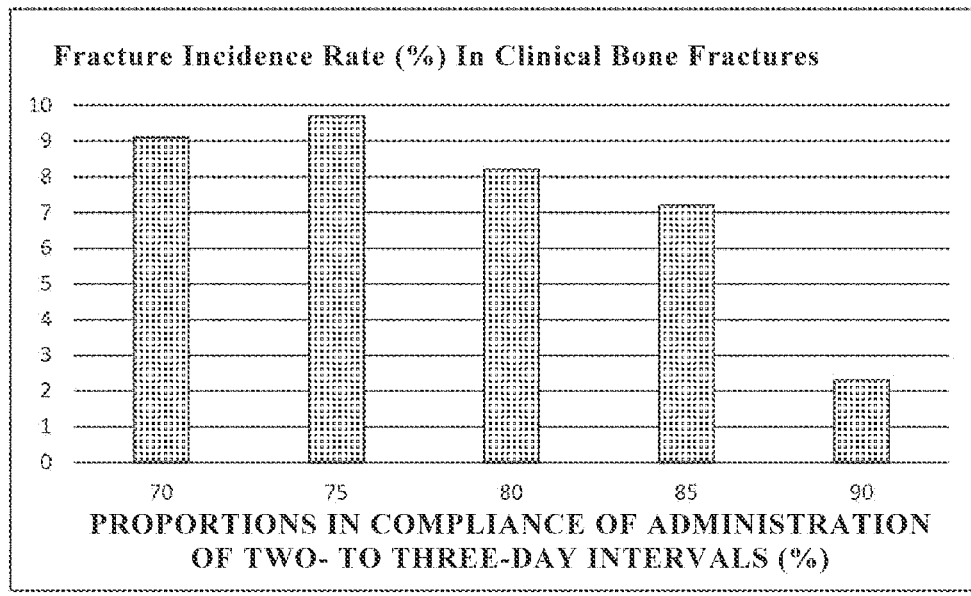

As mentioned above, the clinical bone fractures are bone fractures that embrace vertebral and non-vertebral bone fractures. In view of the above, the analysis results on the influences given by fluctuations of a specified value to the bone fracture incidence rate (%) for the clinical bone fractures indicated by patients having a proportion in compliance with the administration of 2-day to 3-day intervals of a specified value (%) or more are shown in FIG. 26.

In the layer where the proportion is a specified value or more, the larger the proportion in compliance with the administration of 2-day to 3-day intervals, the bone fracture incidence rate (%) tended to be generally decreasing. Therefore, it was considered that the higher the proportion occupied by the weeks in which the intervals of administration in a week (not including the days of administration) is 2-day and 3-day intervals, the higher the therapeutic effects obtained. More specifically, excellent therapeutic effects are exhibited in an embodiment where the same proportion is 70% or more, and even more remarkable therapeutic effects can be acquired in an embodiment where the same proportion is 90% or more. Moreover, in taking strong positive correlative tendencies of the same proportion and the therapeutic effects into account, it was considered that the therapeutic effects would be generally maximized when the same proportion is 100%.

2.9.2.5. Time Transitions of Bone Metabolism Markers (Urine NTX (u-NTX), Serum NTX (s-NTX), CTX, OC, and P1NP) when Distinguishing by Specified Value or More/Less than Specified Value of Each of Proportions in Compliance with Administration Intervals:

The time transitions of the bone metabolism markers (urine NTX (u-NTX), serum NTX (s-NTX), CTX, OC, and P1NP) when distinguished by a specified value or more/less than a specified value of each of the proportions in compliance with administration intervals were calculated. The results are shown in the following Tables 2-47 to 2-51.

TABLE 2-47

Median value of change rates (%) in urine NTX (u-NTX) at each time point when distinguished by a specified value or more/less than a specified value of each of the proportions in compliance with the administration of 2-day to 3-day intervals

| Proportion in compliance with administration of 2-day to 3-day intervals | | Week 4 | Week 12 | Week 24 | Week 48 |
|---|---|---|---|---|---|
| 70% | or more | −20.8 | −20.4 | −32.2 | −25.5 |
| | less than | −5.4 | −1.7 | −15.4 | −5.9 |
| 75% | or more | −20.9 | −21.2 | −34.5 | −27.1 |
| | less than | −7.8 | −7.1 | −16.0 | −12.4 |
| 80% | or more | −23.6 | −22.3 | −35.1 | −28.3 |
| | less than | −8.8 | −12.4 | −20.0 | −13.0 |

TABLE 2-47-continued

Median value of change rates (%) in urine NTX (u-NTX) at each time point when distinguished by a specified value or more/less than a specified value of each of the proportions in compliance with the administration of 2-day to 3-day intervals

| Proportion in compliance with administration of 2-day to 3-day intervals | | Week 4 | Week 12 | Week 24 | Week 48 |
|---|---|---|---|---|---|
| 85% | or more | −26.1 | −22.3 | −35.5 | −28.7 |
| | less than | −15.8 | −15.8 | −25.6 | −13.2 |
| 90% | or more | −22.1 | −11.6 | −33.4 | −24.6 |
| | less than | −16.2 | −18.6 | −30.4 | −18.3 |

TABLE 2-48

Median value of change rates (%) in serum NTX (s-NTX) at each time point when distinguished by a specified value or more/less than a specified value of each of the proportions in compliance with the administration of 2-day to 3-day intervals

| Proportion in compliance with administration of 2-day to 3-day intervals | | Week 4 | Week 12 | Week 24 | Week 48 |
|---|---|---|---|---|---|
| 70% | or more | −6.3 | −6.0 | −11.7 | −8.8 |
| | less than | −0.3 | −0.9 | −2.4 | 0.0 |
| 75% | or more | −6.6 | −6.2 | −12.2 | −8.8 |
| | less than | −3.1 | −3.7 | −3.1 | −1.7 |
| 80% | or more | −7.1 | −5.7 | −12.2 | −8.9 |
| | less than | −3.2 | −5.3 | −6.5 | −5.5 |
| 85% | or more | −6.3 | −5.6 | −12.2 | −10.8 |
| | less than | −3.7 | −5.5 | −7.2 | −5.5 |
| 90% | or more | −5.1 | −2.9 | −11.2 | −10.8 |
| | less than | −5.2 | −5.7 | −7.9 | −5.7 |

TABLE 2-49

Median value of change rates (%) in CTX at each time point when distinguished by a specified value or more/less than a specified value of each of the proportions in compliance with the administration of 2-day to 3-day intervals

| Proportion in compliance with administration of 2-day to 3-day intervals | | Week 4 | Week 12 | Week 24 | Week 48 |
|---|---|---|---|---|---|
| 70% | or more | −22.0 | −16.9 | −24.3 | −31.2 |
| | less than | −13.8 | −11.5 | −9.8 | −20.0 |
| 75% | or more | −22.2 | −16.4 | −25.0 | −30.6 |
| | less than | −15.6 | −15.9 | −13.8 | −27.0 |
| 80% | or more | −23.8 | −18.0 | −27.0 | −30.4 |
| | less than | −14.5 | −14.1 | −14.7 | −29.3 |
| 85% | or more | −23.1 | −18.8 | −27.3 | −30.6 |
| | less than | −17.3 | −15.9 | −16.6 | −28.6 |
| 90% | or more | −23.5 | −15.6 | −28.3 | −33.3 |
| | less than | −19.1 | −16.3 | −18.5 | −29.2 |

TABLE 2-50

Median value of change rates (%) in OC at each time point when distinguished by a specified value or more/less than a specified value of each of the proportions in compliance with the administration of 2-day to 3-day intervals

| Proportion in Compliance with Administration of 2-day to 3-Day Intervals | | Week 4 | Week 12 | Week 24 | Week 48 |
|---|---|---|---|---|---|
| 70% | or more | 46.7 | 41.2 | 23.9 | 6.5 |
| | less than | 40.3 | 43.2 | 19.8 | 8.2 |
| 75% | or more | 47.5 | 41.3 | 24.4 | 6.7 |
| | less than | 41.2 | 42.8 | 18.5 | 7.7 |
| 80% | or more | 47.6 | 39.7 | 22.8 | 3.3 |
| | less than | 41.9 | 44.0 | 25.0 | 9.1 |
| 85% | or more | 47.0 | 39.9 | 23.3 | 4.1 |
| | less than | 44.2 | 43.2 | 24.6 | 8.1 |
| 90% | or more | 44.7 | 39.9 | 22.3 | 4.5 |
| | less than | 46.3 | 43.2 | 23.9 | 7.4 |

TABLE 2-51

Median value of change rates (%) in P1NP at each time point when distinguished by a specified value or more/less than a specified value of each of the proportions in compliance with the administration intervals

| Proportion in compliance with administration of 2-day to 3-day intervals | | Week 4 | Week 12 | Week 24 | Week 48 |
|---|---|---|---|---|---|
| 70% | or more | 27.3 | 12.9 | 1.3 | −4.4 |
| | less than | 31.0 | 15.2 | 10.3 | 11.1 |
| 75% | or more | 25.9 | 13.3 | 1.4 | −5.5 |
| | less than | 30.5 | 14.8 | 7.5 | 6.1 |
| 80% | or more | 27.6 | 13.7 | 0.6 | −3.6 |
| | less than | 28.7 | 14.1 | 3.6 | 1.2 |
| 85% | or more | 29.2 | 15.3 | −1.6 | −3.1 |
| | less than | 28.5 | 13.6 | 3.1 | 0.0 |
| 90% | or more | 37.5 | 18.8 | 3.6 | −2.7 |
| | less than | 28.3 | 13.6 | 2.1 | −1.4 |

Figure 27:
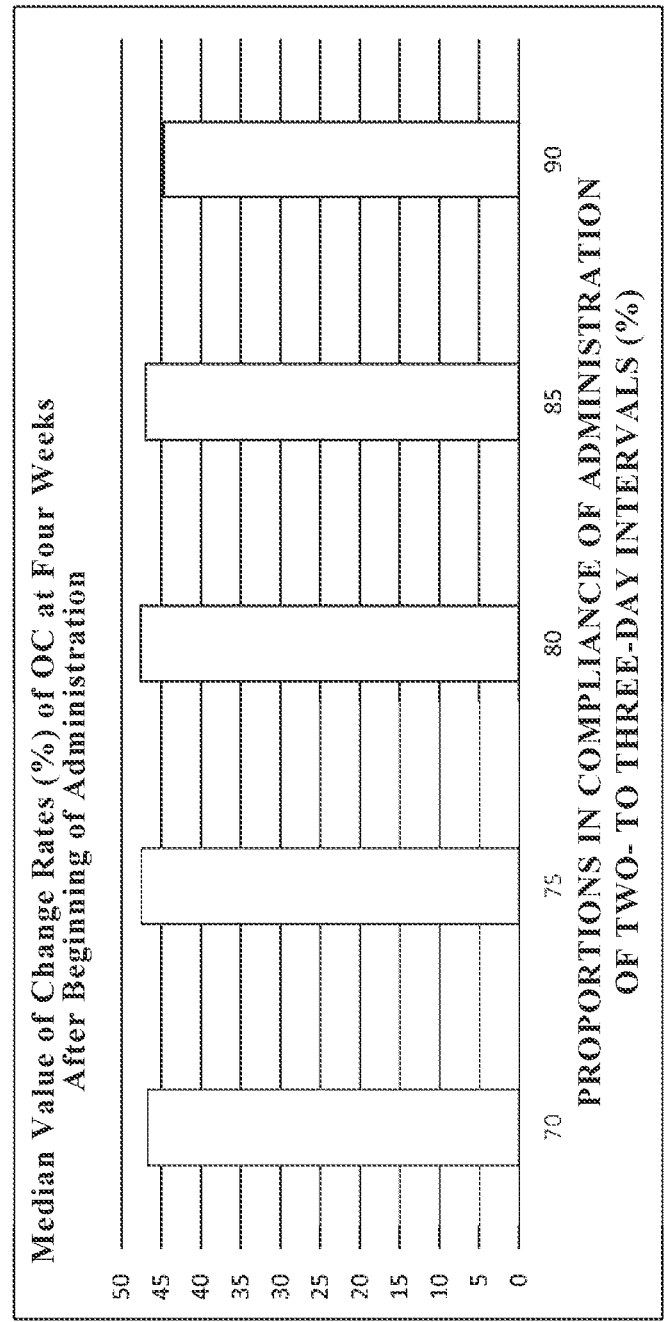

As a bone metabolism marker for observing bone formation action of a daily administered preparation or a once-weekly administered preparation, each containing teriparatide or a salt thereof as an active ingredient, serum osteocalcin (OC) has been widely used (Non-Patent Publication 5 or the like). In addition, in the administration with a test drug in the present invention, the peak of OC elevation is found roughly four weeks after the beginning of administration (FIG. 8). In view of the above, the analysis results on the influences given by fluctuations of a specified value to OC indicated by patients having a proportion in compliance with the administration of 2-day to 3-day intervals of a specified value (%) or more at four weeks after the beginning of administration are shown in FIG. 27.

As to a bone formation marker OC, contrary to the therapeutic effects mentioned above, a distinct correlation with the proportion in compliance with the administration of 2-day to 3-day intervals was not found in the layer in which the proportion was at a level of a specified value or more.

It has been known that a parathyroid hormone drug is a bone formation accelerator (Non-Patent Publication 9), and the dissociation of a bone formation marker and a bone resorption marker is recognized as an efficacy index in the daily osteoporosis treatment using teriparatide (Non-Patent Publication 24). Therefore, with regard to the correlation with the proportion in compliance with the administration of 2-day or 3-day intervals, the present analysis results in which different tendencies were shown between the therapeutic effects and the bone formation marker OC were considered to be highly epoch-making in light of the findings of the conventional teriparatide therapies.

2.9.2.6. Number of Cases of Expression and Expression Ratios (%) of all Side Effects and Nausea (Side Effects) when Distinguished by Specified Value or More/Less than Specified Value of Each of Proportions in Compliance of Administration Intervals:

TABLE 2-52

Number of cases of incidence and expression ratios (%) of all side effects when distinguished by a specified value or more/less than a specified value of each of the proportions in compliance with the administration of 2-day to 3-day intervals

| Proportion in compliance with administration intervals | | No. of subject cases | No. of cases of expression | Expression ratio (%) |
|---|---|---|---|---|
| 70% | or more | 186 | 69 | 37.1 |
|  | less than | 56 | 24 | 42.9 |
| 75% | or more | 165 | 58 | 35.2 |
|  | less than | 77 | 35 | 45.5 |
| 80% | or more | 122 | 39 | 32.0 |
|  | less than | 120 | 54 | 45.0 |
| 85% | or more | 83 | 25 | 30.1 |
|  | less than | 159 | 68 | 42.8 |
| 90% | or more | 43 | 13 | 30.2 |
|  | less than | 199 | 80 | 40.2 |

TABLE 2-53

Number of cases of incidence and expression ratios (%) of nausea (side effects) when distinguished by a specified value or more and less than a specified value of each of the proportions in compliance with the administration of 2-day to 3-day intervals

| Proportion in compliance with administration intervals | | No. of subject cases | No. of cases of expression | Expression ratio (%) |
|---|---|---|---|---|
| 70% | or more | 186 | 32 | 17.2 |
|  | less than | 56 | 12 | 21.4 |
| 75% | or more | 165 | 26 | 15.8 |
|  | less than | 77 | 18 | 23.4 |
| 80% | or more | 122 | 16 | 13.1 |
|  | less than | 120 | 28 | 23.3 |
| 85% | or more | 83 | 11 | 13.3 |
|  | less than | 159 | 33 | 20.8 |
| 90% | or more | 43 | 5 | 11.6 |
|  | less than | 199 | 39 | 19.6 |

Figure 28:
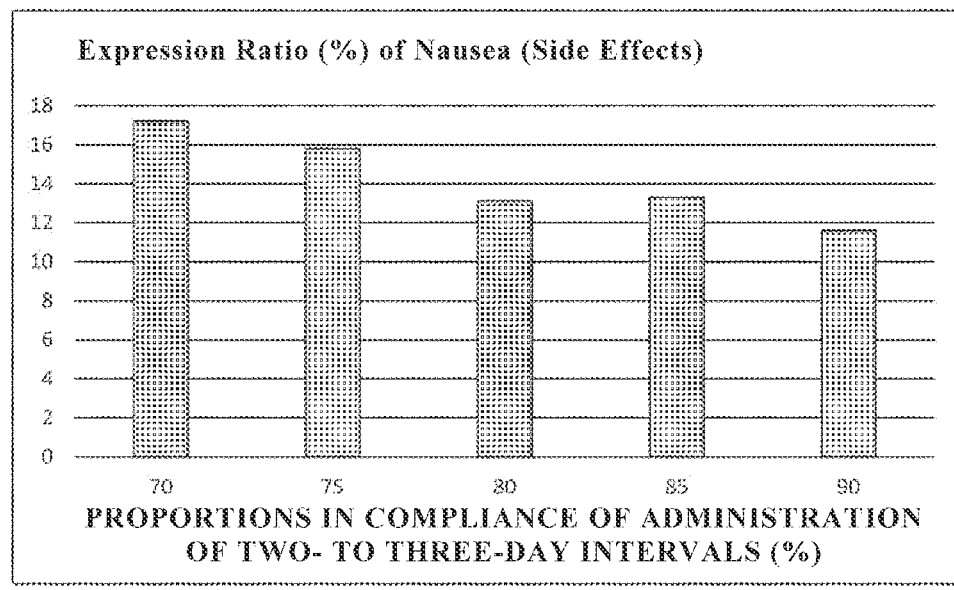

As mentioned in the above 2.8.2, the nausea was a side effect having the highest expression ratio. In view of the above, the analysis results on the influences given by fluctuations of a specified value (%) to the expression ratio (%) of nausea indicated by patients having a proportion in compliance with the administration of 2-day to 3-day intervals of a specified value (%) or more are shown in FIG. 28.

In the group in which the proportion in compliance with the administration intervals is a specified value or more, the larger the proportion in compliance with the administration intervals, the expression ratio of nausea (side effects) tended to be low. Therefore, it was considered that the higher the proportion occupied by the weeks in which the administration intervals in a week (not including the days of administration) are 2-day and 3-day intervals, the therapy has higher safety. More specifically, excellent safety was shown in an embodiment in which the same proportion was 70% or more, and taking the strong positive correlative tendencies between the same proportion and safety into account, it was considered that the safety is generally probably maximized when the same proportion is 100%.

Working Example 2

1. Test Method

To evaluate the influences of the administration frequencies of teriparatide on the bone metabolism and the bone tissue morphology, six-month old female rabbits were subcutaneously administered with an agent in a manner that a weekly dosage of teriparatide was adjusted to 140 µg/kg at a frequency of once a week, twice a week or seven times a week over 4 weeks, or with a control drug without containing teriparatide at a frequency of seven times a week over 4 weeks (Table 2-54). Also, the bone mineral density and the bone strength of the tibiae were measured. The teriparatide solution which was administered was appropriately prepared by dissolving teriparatide acetate in a water for injection, filtering the solution, filling the filtrate in a vial, freeze-drying to give a preparation, and dissolving the preparation in a physiological saline upon use.

TABLE 2-54

Contents of each test group

| Group | Administered drug | Unit dose (µg/kg) (concentration administered (µg/mL/kg)) | No. of administration per week | Total dose per week (µg/kg) |
|---|---|---|---|---|
| Control group | Teriparatide acetate | 0 (0) | 7 | 0 |
| Group administered once a week | Teriparatide acetate | 140 (1400) | 1 | 140 |
| Group administered twice a week | Teriparatide acetate | 70 (700) | 2 | 140 |
| Group administered seven times a week | Teriparatide acetate | 20 (200) | 7 | 140 |

2. Test Results (1) Bone Mineral Densities of Tibiae

The bone mineral densities of the tibiae were analyzed in divided regions. As a result, the administration of teriparatide remarkably increased the bone mineral densities in the proximal part (⅕ site) rich in trabecular bones, as compared to those of the control group, and the bone mineral densities of the group administered twice a week had a higher value than that of the group administered once a week in this site. The present test results agree with the test results for Working Example 1 (Table 2-4) showing that the bone mineral densities of the group administered twice a week had a higher value than that of the group administered once a week in the lumbar vertebrae (second to fourth lumbar vertebrae) rich in trabecular bones in the same manner as the proximal part of the tibiae (the lumbar vertebrae being composed of 60% trabecular bones, and the centrum being composed of 80% trabecular bones; Non-Patent Publication 26).

TABLE 2-55

Influences of administration frequency of teriparatide on bone mineral densities in proximal part (1/5 site) of the tibiae of rabbits

| | Control group | Group administered once a week | Group administered twice a week |
|---|---|---|---|
| Bone mineral densities (mg/cm$^2$) | 254.2 ± 10.9 | 272.5 ± 13.6 | 278.8 ±9.8 |

(2) Bone Strength of Tibiae

Three-point bending strength of the tibiae collected after the end of the administration period was measured. As a result, the maximum load showed higher values in the group administered with the present drug twice a week and the group administered seven times a week, than the control group.

TABLE 2-56

Influences of administration frequency of teriparatide on bone strength of tibiae of rabbits

|  | Control group | Group administered once a week | Group administered twice a week | Group administered seven times a week |
|---|---|---|---|---|
| Maximum load (N) | 578.93 ± 51.42 | 583.81 ± 44.23 | 624.41 ± 45.32 | 656.09 ± 59.86 |

(3) Bone Tissue Morphology of Diaphysis of Tibiae

In the group administered seven times a week, the formation of trabecular bones on the endocortical surfaces, a large number of intracortical voids (increase of cortical porosity), and disorderedness in a lamellar structure were observed, but none of these findings were observed in the group administered once a week and the group administered twice a week.

Non-Patent Publication 14 has reported that the administration of teriparatide at high frequencies enhances the bone turnover, suggesting that the increase in void ratios of the cortical bone with teriparatide is strongly influenced by the administration frequencies. In the present working example, the enhancement in the bone turnover that would increase the void ratio of the cortical bones was not found, in the therapy of administration of twice a week, despite the doubling in the administration frequencies of the therapy of administration of once a week. This matter, in light of Non-Patent Publication 14, was considered to be unexpected and epoch-making results.

In addition, Non-Patent Publication 17 has reported that the daily administration of teriparatide increases a bone resorption marker. Further, it is suggested that in Non-Patent Publication 27, an eroded surface showing bone resorption in a void surface of the cortical bone caused by daily administration of teriparatide has been found (see, FIG. 7 *c* or the like), so that the porosity of the cortical bone has a deep relationship with the enhancement of bone resorption.

In Working Example 1, the time transitions of the bone resorption marker with the treatment of administration of twice a week were of the same level or slightly inhibited, as compared to the time transitions of the bone resorption marker with the treatment of administration of once a week (FIGS. 5 to 7). However, through the mechanisms mentioned above, it can be assumed that the treatment of administration of twice a week is a therapy that does not show the acceleration of the bone turnover that would increase the void ratios of the cortical bones regardless of the doubling of the administration frequency of that of the therapy of once a week. Therefore, the effects of Working Example 1 were supported by the results of the test with rabbits of Working Example 2.

The invention claimed is:

1. A method of therapeutically treating or prophylactically treating osteoporosis in a patient in need thereof which comprises administering to said patient a pharmaceutical agent comprising teriparatide or a salt thereof as an active ingredient, wherein said teriparatide or a salt thereof is administered in a unit dose of 28.2 μg at a frequency of twice a week, wherein when the number of weeks of a period administered at a frequency of twice a week is defined as n, and the number of weeks in which the intervals (not including the days of administration) of administration of twice a week out of the n weeks are a 2-day interval and a 3-day interval is defined as m, (m/n)×100(%) is 70% or more.

2. The method according to claim 1, wherein the pharmaceutical agent is subcutaneously administered.

* * * * *